US012570995B2

(12) United States Patent
Décousset et al.

(10) Patent No.: US 12,570,995 B2
(45) Date of Patent: Mar. 10, 2026

(54) INSECTICIDAL PROTEINS COMPOSITIONS AND METHODS OF USE

(71) Applicant: GENECTIVE SA, Champaign, IL (US)

(72) Inventors: Laurent Décousset, Champaign, IL (US); James Winsor, Champaign, IL (US); Yuanyuan Hu, Champaign, IL (US); Madison Havel, Champaign, IL (US); Christophe Sallaud, Champaign, IL (US); Mickael Bosio, Champaign, IL (US)

(73) Assignee: GENECTIVE SA, Champaign, IL (US)

( * ) Notice: Subject to any disclaimer, the term of this patent is extended or adjusted under 35 U.S.C. 154(b) by 0 days.

(21) Appl. No.: 19/201,636

(22) Filed: May 7, 2025

(65) Prior Publication Data

US 2025/0346916 A1      Nov. 13, 2025

Related U.S. Application Data

(60) Provisional application No. 63/644,183, filed on May 8, 2024.

(51) Int. Cl.
| | |
|---|---|
| *C12N 15/82* | (2006.01) |
| *A01N 37/46* | (2006.01) |
| *A01P 7/04* | (2006.01) |
| *C07K 14/19* | (2006.01) |
| *C07K 14/195* | (2006.01) |

(52) U.S. Cl.
CPC ......... *C12N 15/8286* (2013.01); *A01N 37/46* (2013.01); *A01P 7/04* (2021.08); *C07K 14/195* (2013.01)

(58) Field of Classification Search
CPC ....... C12N 15/8286; A01P 7/04; A01N 37/46; C07K 14/195
See application file for complete search history.

(56) References Cited

U.S. PATENT DOCUMENTS

| | | | |
|---|---|---|---|
| 5,188,960 | A | 2/1993 | Payne et al. |
| 5,605,793 | A | 2/1997 | Stemmer |
| 5,837,458 | A | 11/1998 | Minshull et al. |
| 5,880,275 | A | 3/1999 | Fischhoff et al. |
| 6,033,874 | A | 3/2000 | Baum et al. |
| 6,048,838 | A | 4/2000 | Ensign et al. |
| 6,083,499 | A | 7/2000 | Narva et al. |
| 6,127,180 | A | 10/2000 | Narva et al. |
| 6,218,188 | B1 | 4/2001 | Cardineau et al. |
| 6,248,535 | B1 | 6/2001 | Danenberg et al. |
| 6,326,351 | B1 | 12/2001 | Donovan et al. |
| 6,340,593 | B1 | 1/2002 | Cardineau et al. |
| 6,379,946 | B1 | 4/2002 | Ensign et al. |
| 6,399,330 | B1 | 6/2002 | Donovan et al. |
| 6,501,009 | B1 | 12/2002 | Romano |
| 6,548,291 | B1 | 4/2003 | Narva et al. |
| 6,624,145 | B1 | 9/2003 | Narva et al. |

| | | | |
|---|---|---|---|
| 6,713,063 | B1 | 3/2004 | Malvar et al. |
| 6,949,626 | B2 | 9/2005 | Donovan et al. |
| 6,962,705 | B2 | 11/2005 | Malvar et al. |
| 7,064,249 | B2 | 6/2006 | Corbin et al. |
| 7,070,982 | B2 | 7/2006 | Malvar et al. |
| 7,105,332 | B2 | 9/2006 | Abad et al. |
| 7,208,474 | B2 | 4/2007 | Bermudez et al. |
| 7,329,736 | B2 | 2/2008 | Abad et al. |
| 7,339,092 | B2 | 3/2008 | Abad et al. |
| 7,378,499 | B2 | 5/2008 | Abad et al. |
| 7,385,107 | B2 | 6/2008 | Donovan et al. |
| 7,449,552 | B2 | 11/2008 | Abad et al. |
| 7,462,760 | B2 | 12/2008 | Abad et al. |
| 7,476,781 | B2 | 1/2009 | Abad et al. |
| 7,504,229 | B2 | 3/2009 | Donovan et al. |
| 7,510,878 | B2 | 3/2009 | Abad et al. |
| 7,772,465 | B2 | 8/2010 | Abad et al. |
| 7,803,943 | B2 | 9/2010 | Mao et al. |
| 7,812,129 | B1 | 10/2010 | Abad et al. |
| 7,858,849 | B2 | 12/2010 | Cerf et al. |
| 7,923,602 | B2 | 4/2011 | Carozzi et al. |
| 8,084,416 | B2 | 12/2011 | Sampson et al. |
| 8,236,757 | B2 | 8/2012 | Carozzi et al. |
| 8,252,872 | B2 | 8/2012 | Tournilhac et al. |
| 8,304,604 | B2 | 11/2012 | Lira et al. |
| 8,304,605 | B2 | 11/2012 | Lira et al. |

(Continued)

FOREIGN PATENT DOCUMENTS

| | | |
|---|---|---|
| WO | 2004074462 A2 | 9/2004 |
| WO | 2005021585 A2 | 3/2005 |

(Continued)

OTHER PUBLICATIONS

US 8,476,226 B2, 07/2013, Lira et al. (withdrawn)
NCBI Reference Sequence_WP_143097042_1, NCBI protein database, BCT Jul. 21, 2019 (Year: 2019).*
Locus SET64083 from Myxococcus fulvus in Embl accession FOIB01000002.1, NCBI protein database, BCT Oct. 29, 2016 (Year: 2016).*
Locus GEN05900 Myxococcus fulvus, accession BJXR01000013.1, NCBI protein database, BCT Aug. 23, 2023 (Year: 2023).*
Guo et al. (Published Year: 2004, Journal: Proceedings of the National Academy of Sciences, vol. 101(25), pp. 9205-9210). (Year: 2004).*
Selvapandiyan et al. (Published: 2001, Journal: Applied and Environmental Microbiology, 67(12), 5855-5858). (Year: 2001).*

(Continued)

*Primary Examiner* — David H Kruse
*Assistant Examiner* — Santosh Sharma
(74) *Attorney, Agent, or Firm* — Michael Best & Friedrich LLP

(57)      ABSTRACT

Disclosed herein are transformed plants, plant tissues, plant parts, plant cells, and plant seeds comprising a recombinant nucleic acid molecule encoding a polypeptide having pesticidal activity. Also disclosed herein are methods of protecting or treating a plant from infection by a plant pathogen or pest by transforming plants, plant tissues, plant parts, plant cells, and plant seeds with a recombinant nucleic acid molecule encoding a polypeptide having pesticidal activity.

5 Claims, 12 Drawing Sheets

Specification includes a Sequence Listing.

(56) References Cited

U.S. PATENT DOCUMENTS

| | | | |
|---|---|---|---|
| 8,318,900 | B2 | 11/2012 | Sampson et al. |
| 8,319,019 | B2 | 11/2012 | Abad et al. |
| 8,334,431 | B2 | 12/2012 | Sampson et al. |
| 8,461,415 | B2 | 6/2013 | Sampson et al. |
| 8,461,421 | B2 | 6/2013 | Sampson et al. |
| 8,461,422 | B2 | 6/2013 | Lira et al. |
| 8,513,493 | B2 | 8/2013 | Baum et al. |
| 8,609,936 | B2 | 12/2013 | Baum et al. |
| 8,772,577 | B2 | 7/2014 | Abad et al. |
| 8,802,933 | B2 | 8/2014 | Abad et al. |
| 8,816,157 | B2 | 8/2014 | Schnepf |
| 8,878,007 | B2 | 11/2014 | Abad et al. |
| 8,933,299 | B2 | 1/2015 | Abad et al. |
| 9,000,261 | B2 | 4/2015 | Abad et al. |
| 9,403,881 | B2 | 8/2016 | Abad et al. |
| 9,404,121 | B2 | 8/2016 | Abad et al. |
| 9,475,847 | B2 | 10/2016 | Altier et al. |
| 9,512,187 | B2 | 12/2016 | Je et al. |
| 9,593,345 | B2 | 3/2017 | Yamamoto et al. |
| 9,688,730 | B2 | 6/2017 | Cerf et al. |
| 11,213,028 | B2 | 1/2022 | Barry et al. |
| 11,492,639 | B2 | 11/2022 | Abad et al. |
| 11,739,344 | B2 | 8/2023 | Barry et al. |
| 12,227,544 | B2 | 2/2025 | Gruver et al. |
| 2004/0197916 | A1 | 10/2004 | Carozzi et al. |
| 2004/0197917 | A1 | 10/2004 | Carozzi et al. |
| 2004/0210964 | A1 | 10/2004 | Carozzi et al. |
| 2004/0210965 | A1 | 10/2004 | Carozzi et al. |
| 2004/0216186 | A1 | 10/2004 | Carozzi et al. |
| 2004/0250311 | A1 | 12/2004 | Carozzi et al. |
| 2006/0112447 | A1 | 5/2006 | Bogdanova et al. |
| 2006/0191034 | A1 | 8/2006 | Baum et al. |
| 2008/0172762 | A1 | 7/2008 | Cerf et al. |
| 2008/0295207 | A1 | 11/2008 | Baum et al. |
| 2009/0144852 | A1 | 6/2009 | Tomso et al. |
| 2009/0313721 | A1 | 12/2009 | Abad et al. |
| 2010/0004176 | A1 | 1/2010 | Sampson et al. |
| 2010/0017914 | A1 | 1/2010 | Hart et al. |
| 2010/0077507 | A1 | 3/2010 | Abad et al. |
| 2010/0077508 | A1 | 3/2010 | Abad et al. |
| 2010/0137216 | A1 | 6/2010 | Carozzi et al. |
| 2010/0160231 | A1 | 6/2010 | Sampson et al. |
| 2010/0192256 | A1 | 7/2010 | Abad et al. |
| 2010/0197592 | A1 | 8/2010 | Heinrichs |
| 2010/0269221 | A1 | 10/2010 | Abad et al. |
| 2010/0298211 | A1 | 11/2010 | Carozzi et al. |
| 2010/0317569 | A1 | 12/2010 | Lira et al. |
| 2010/0319092 | A1 | 12/2010 | Lira et al. |
| 2010/0319093 | A1 | 12/2010 | Lira et al. |
| 2011/0023184 | A1 | 1/2011 | Desai et al. |
| 2011/0030096 | A1 | 2/2011 | Sampson et al. |
| 2011/0055968 | A1 | 3/2011 | Cerf et al. |
| 2011/0064710 | A1 | 3/2011 | Benson et al. |
| 2011/0112013 | A1 | 5/2011 | Abad et al. |
| 2011/0154536 | A1 | 6/2011 | Abad et al. |
| 2011/0263488 | A1 | 10/2011 | Carozzi et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0210462 | A1 | 8/2012 | Bermudez et al. |
| 2012/0233726 | A1 | 9/2012 | Abad et al. |
| 2012/0278954 | A1 | 11/2012 | Bowen et al. |
| 2013/0055469 | A1 | 2/2013 | Sampson et al. |
| 2013/0097735 | A1 | 4/2013 | Bowen et al. |
| 2013/0104259 | A1 | 4/2013 | Sampson et al. |
| 2013/0117884 | A1 | 5/2013 | Hargiss et al. |
| 2013/0167264 | A1 | 6/2013 | Sampson et al. |
| 2013/0219570 | A1 | 8/2013 | Lira et al. |
| 2013/0269060 | A1 | 10/2013 | Baum et al. |
| 2013/0303440 | A1 | 11/2013 | Sampson et al. |
| 2013/0310543 | A1 | 11/2013 | Sampson et al. |
| 2014/0007292 | A1 | 1/2014 | Cerf et al. |
| 2014/0033361 | A1 | 1/2014 | Altier et al. |
| 2014/0033363 | A1 | 1/2014 | Sampson |
| 2014/0196175 | A1 | 7/2014 | Sampson et al. |
| 2014/0223598 | A1 | 8/2014 | Sampson et al. |
| 2014/0223599 | A1 | 8/2014 | Sampson et al. |
| 2014/0245491 | A1 | 8/2014 | Sampson et al. |
| 2014/0298538 | A1 | 10/2014 | Heinrichs et al. |
| 2014/0366227 | A1 | 12/2014 | Gatehouse et al. |
| 2014/0373195 | A1 | 12/2014 | Sampson et al. |
| 2016/0150795 | A1 | 6/2016 | Baum et al. |
| 2016/0177332 | A1 | 6/2016 | Thayer et al. |
| 2016/0186204 | A1 | 6/2016 | Liu et al. |
| 2016/0194364 | A1 | 7/2016 | Abad et al. |
| 2016/0347799 | A1 | 12/2016 | Barry et al. |
| 2016/0366891 | A1 | 12/2016 | Diehn et al. |
| 2017/0166921 | A1 | 6/2017 | Barry et al. |
| 2017/0233440 | A1 | 8/2017 | Barry et al. |
| 2017/0233759 | A1 | 8/2017 | Abad et al. |
| 2017/0240603 | A1 | 8/2017 | Abad et al. |
| 2020/0138038 | A1 | 5/2020 | Ashby et al. |

FOREIGN PATENT DOCUMENTS

| | | | |
|---|---|---|---|
| WO | 2005038032 | A1 | 4/2005 |
| WO | 2006083891 | A2 | 8/2006 |
| WO | 2006119457 | A1 | 11/2006 |
| WO | 2007027776 | A2 | 3/2007 |
| WO | 2011103247 | A2 | 8/2011 |
| WO | 2011103248 | A2 | 8/2011 |
| WO | 2012139004 | A2 | 10/2012 |
| WO | 2014008054 | A2 | 1/2014 |
| WO | 2016061197 | A1 | 4/2016 |
| WO | 2016114973 | A1 | 7/2016 |
| WO | 2017023486 | A1 | 2/2017 |
| WO | 2017105987 | A1 | 6/2017 |
| WO | 2017132188 | A1 | 8/2017 |
| WO | 2017192560 | A1 | 11/2017 |
| WO | 2018005411 | A1 | 1/2018 |
| WO | 2018111553 | A1 | 6/2018 |
| WO | 2019169227 | A1 | 9/2019 |

OTHER PUBLICATIONS

Leone et al. (Published: 2015, Journal: The journal of biological chemistry 290 (21): 13191-13201). (Year: 2015).*

Wei et al. (Published 2018, Journal: Plant Biotechnology Journal 16: 649-659). (Year: 2018).*

Han et al. (Published: Apr. 2024, Journal: Front. Microbiol. 15:1378288. doi: 10.3389/fmicb.2024.1378288). (Year: 2024).*

Database UniProt. RecName: Full=Monalysin beta barrel Pore-Forming domain-containing protein {ECO:0000259 | Pfam:PF18063}, retrieved from EBI accession No. UNIPROT:A0A511SCI2. 2019, (1 page).

Mukundan, M. et al. "A Phylogenetic Study of Monalysin Family of Proteobacterial Pore-Forming Toxins." Proceedings of the 2018 5th International Conference on Biomedical and Bioinformatics Engineering. 2018, 11-20.

International Searching Authority. Invitation to Pay Additional Fees for Application No. PCT/US2025/026185. Mailed on Jul. 30, 2025 (14 pages).

Crickmore et al., "Bacillus thuringiensis toxin nomenclature" (2011), version dated Aug. 19, 2020, available online at https://web.archive.org/web/20200819224235/http://www.lifesci.sussex.ac.uk/home/Neil_Crickmore/Bt/ (3 pages).

Hinchliffe, S. J., et al. "Insecticidal toxins from the Photorhabdus and Xenorhabdus bacteria." Open Toxinology Journal 3.2 (2010): 83-100.

Crameri, A., et al. "DNA shuffling of a family of genes from diverse species accelerates directed evolution." Nature 391.6664 (1998): 288-291.

Crameri, A., et al. "Molecular evolution of an arsenate detoxification pathway by DNA shuffling." Nature biotechnology 15.5 (1997): 436-438.

Crickmore, N., et al. "A structure-based nomenclature for Bacillus thuringiensis and other bacteria-derived pesticidal proteins." Journal of invertebrate pathology 186 (2021): 107438.

(56) References Cited

OTHER PUBLICATIONS

De Maagd, R. A., et al. "Domain III substitution in Bacillus thuringiensis delta-endotoxin CrylA (b) results in superior toxicity for Spodoptera exigua and altered membrane protein recognition." Applied and environmental microbiology 62.5 (1996): 1537-1543.

Ge, A. Z., et al. "Functional domains of Bacillus thuringiensis insecticidal crystal proteins. Refinement of Heliothis virescens and Trichoplusia ni specificity domains on CrylA (c)." Journal of Biological Chemistry 266.27 (1991): 17954-17958.

GENBANK. Accession No. EU400157. Pseudomonas protegens strain CHA0 insecticidal toxin gene locus, complete sequence. Sep. 25, 2012. Available online at https://www.ncbi.nlm.nih.gov/nuccore/EU400157 (12 pages).

Huynh, M. P., et al. "Diet improvement for western corn rootworm (Coleoptera: Chrysomelidae) larvae." PloS one 12.11 (2017): e0187997.

Kapila, J., et al. "An Agrobacterium-mediated transient gene intact leaves." Plant Science 122.101 (1997): 101-108.

Li, D., et al. "Agrobacterium-mediated genetic transformation of Elymus breviaristatus with Pseudomonas pseudoalcaligenes insecticidal protein gene." Plant cell, tissue and organ culture 89.2 (2007): 159-168.

Liu, J.-R., et al. "Molecular cloning and characterization of an insecticidal toxin from Pseudomonas taiwanensis." Journal of agricultural and food chemistry 58.23 (2010): 12343-12349.

Ludwick, D. C., et al. "A new artificial diet for western corn rootworm larvae is compatible with and detects resistance to all current Bt toxins." Scientific reports 8.1 (2018): 5379.

Moore, J. C., et al. "Strategies for the in vitro evolution of protein function: enzyme evolution by random recombination of improved sequences." Journal of molecular biology 272.3 (1997): 336-347.

Morgan, J. A. W., et al. "Sequence analysis of insecticidal genes from Xenorhabdus nematophilus PMFI296." Applied and Environmental Microbiology 67.5 (2001): 2062-2069.

Naimov, S., et al. "Bacillus thuringiensis delta-endotoxin Cryl hybrid proteins with increased activity against the Colorado potato beetle." Applied and Environmental Microbiology 67.11 (2001): 5328-5330.

Naimov, S., et al. "Solubilization, activation, and insecticidal activity of Bacillus thuringiensis serovar thompsoni HD542 crystal proteins." Applied and environmental microbiology 74.23 (2008): 7145-7151.

Opota, O., et al. "Monalysin, a novel ß-pore-forming toxin from the Drosophila pathogen Pseudomonas entomophila, contributes to host intestinal damage and lethality." PLoS pathogens 7.9 (2011): e1002259.

Péchy-Tarr, M., et al. "Molecular analysis of a novel gene cluster encoding an insect toxin in plant-associated strains of Pseudomonas fluorescens." Environmental microbiology 10.9 (2008): 2368-2386.

Rang, C., et al. "Interaction between functional domains of Bacillus thuringiensis insecticidal crystal proteins." Applied and Environmental Microbiology 65.7 (1999): 2918-2925.

Schnepf, H. E., et al. "Specificity-determining regions of a lepidopteran-specific insecticidal protein produced by Bacillus thuringiensis." Journal of Biological Chemistry 265.34 (1990): 20923-20930.

Schöb, H., et al. "Silencing of transgenes introduced into leaves by agroinfiltration: a simple, rapid method for investigating sequence requirements for gene silencing." Molecular and General Genetics MGG 256.5 (1997): 581-585.

Stemmer, WPC. "DNA shuffling by random fragmentation and reassembly: in vitro recombination for molecular evolution." Proceedings of the National Academy of Sciences 91.22 (1994): 10747-10751.

Stemmer, WPC. "Rapid evolution of a protein in vitro by DNA shuffling." Nature 370.6488 (1994): 389-391.

Wang, K. et al. "Effective bacterial insecticidal proteins against coleopteran pests: A review." Archives of insect biochemistry and physiology 102.3 (2019): e21558.

Zhang, J., et al. "Cloning of the gene encoding an insecticidal protein in Pseudomonas pseudoalcaligenes." Annals of microbiology 59.1 (2009): 45-50.

Zhang, J.-H et al. "Directed evolution of a fucosidase from a galactosidase by DNA shuffling and screening." Proceedings of the National Academy of Sciences 94.9 (1997): 4504-4509.

International Search Report and Written Opinion for Application No. PCT/US2025/026185 dated Sep. 22, 2025 (19 pages).

* cited by examiner

FIG. 1

| SEQ ID NO | Sequence Name |
|---|---|
| SEQ ID NO: 1 | GUN2873.1.2 |
| SEQ ID NO: 2 | GUN2873.2.1 |
| SEQ ID NO: 3 | GUN2873.3.1 |
| SEQ ID NO: 4 | GUN2873.4.1 |
| SEQ ID NO: 5 | GUN2873.5.1 |
| SEQ ID NO: 6 | GUN2873.6.1 |
| SEQ ID NO: 7 | GUN2873.7.1 |
| SEQ ID NO: 8 | GUN2873.8.1 |
| SEQ ID NO: 9 | GUN2873.9.1 |
| SEQ ID NO: 10 | GUN2873.10.1 |
| SEQ ID NO: 11 | GUN2873.11.1 |
| SEQ ID NO: 12 | GUN2873.12.1 |
| SEQ ID NO: 13 | GUN2873.13.1 |
| SEQ ID NO: 14 | GUN2873.14.1 |
| SEQ ID NO: 15 | GUN2873.15.1 |
| SEQ ID NO: 16 | GUN2873.16.1 |
| SEQ ID NO: 17 | GUN2873.17.1 |
| SEQ ID NO: 18 | GUN2873.18.1 |
| SEQ ID NO: 19 | GUN2873.19.1 |
| SEQ ID NO: 20 | GUN2873.20.1 |
| SEQ ID NO: 21 | GUN2873.21.1 |
| SEQ ID NO: 22 | GUN2873.22.1 |
| SEQ ID NO: 23 | GUN2873.23.1 |
| SEQ ID NO: 24 | GUN2873.24.1 |
| SEQ ID NO: 25 | GUN2873.25.1 |
| SEQ ID NO: 26 | GUN2873.26.1 |
| SEQ ID NO: 27 | GUN2873.27.1 |
| SEQ ID NO: 28 | GUN2873.28.1 |
| SEQ ID NO: 29 | GUN2873.29.1 |
| SEQ ID NO: 30 | GUN2873.30.1 |
| SEQ ID NO: 31 | GUN2873.31.1 |
| SEQ ID NO: 32 | GUN2873.32.1 |
| SEQ ID NO: 33 | GUN2873.33.1 |
| SEQ ID NO: 34 | GUN2873.34.1 |
| SEQ ID NO: 35 | GUN2873.35.1 |
| SEQ ID NO: 36 | GUN2873.36.1 |
| SEQ ID NO: 37 | GUN2873.37.1 |
| SEQ ID NO: 38 | GUN2873.38.1 |
| SEQ ID NO: 39 | GUN2873.39.1 |

FIG. 1 (cont.)

| SEQ ID NO | Sequence Name |
|---|---|
| SEQ ID NO: 40 | GUN2873.40.1 |
| SEQ ID NO: 41 | GUN2873.41.1 |
| SEQ ID NO: 42 | GUN2873.42.1 |
| SEQ ID NO: 43 | GUN2873.43.1 |
| SEQ ID NO: 44 | GUN2873.44.1 |
| SEQ ID NO: 45 | GUN2873.45.1 |
| SEQ ID NO: 46 | GUN2873.46.1 |
| SEQ ID NO: 47 | GUN2873.47.1 |
| SEQ ID NO: 48 | GUN2873.48.1 |
| SEQ ID NO: 49 | GUN2873.49.1 |
| SEQ ID NO: 50 | GUN2873.50.1 |
| SEQ ID NO: 51 | GUN2873.51.1 |
| SEQ ID NO: 52 | GUN2873.52.1 |
| SEQ ID NO: 53 | GUN2873.53.1 |
| SEQ ID NO: 54 | GUN2873.54.1 |
| SEQ ID NO: 55 | GUN2873.55.1 |
| SEQ ID NO: 56 | GUN2873.56.1 |
| SEQ ID NO: 57 | GUN2873.57.1 |
| SEQ ID NO: 58 | GUN2873.58.1 |
| SEQ ID NO: 59 | GUN2873.59.1 |
| SEQ ID NO: 60 | GUN2873.60.1 |
| SEQ ID NO: 61 | GUN2873.61.1 |
| SEQ ID NO: 62 | GUN2873.62.1 |
| SEQ ID NO: 63 | GUN2873.63.1 |
| SEQ ID NO: 64 | GUN2873.64.1 |
| SEQ ID NO: 65 | GUN2873.65.1 |
| SEQ ID NO: 66 | GUN2873.66.1 |
| SEQ ID NO: 67 | GUN2873.67.1 |
| SEQ ID NO: 68 | GUN2873.68.1 |
| SEQ ID NO: 69 | GUN2873.69.1 |
| SEQ ID NO: 70 | GUN2873.70.1 |
| SEQ ID NO: 71 | GUN2873.71.1 |
| SEQ ID NO: 72 | GUN2873.72.1 |
| SEQ ID NO: 73 | GUN2873.73.1 |
| SEQ ID NO: 74 | GUN2873.74.1 |
| SEQ ID NO: 75 | GUN2873.75.1 |
| SEQ ID NO: 76 | GUN2873.76.1 |
| SEQ ID NO: 77 | GUN2873.77.1 |
| SEQ ID NO: 78 | GUN2873.78.1 |

FIG. 1 (cont.)

| SEQ ID NO | Sequence Name |
| --- | --- |
| SEQ ID NO: 79 | GUN2873.79.1 |
| SEQ ID NO: 80 | GUN2873.80.1 |
| SEQ ID NO: 81 | GUN2873.81.1 |
| SEQ ID NO: 82 | GUN2873.82.1 |
| SEQ ID NO: 83 | GUN2873.83.1 |
| SEQ ID NO: 84 | GUN2873.84.1 |
| SEQ ID NO: 85 | GUN2873.85.1 |
| SEQ ID NO: 86 | GUN2873.86.1 |
| SEQ ID NO: 87 | GUN2873.87.1 |
| SEQ ID NO: 88 | GUN2873.88.1 |
| SEQ ID NO: 89 | GUN2873.89.1 |
| SEQ ID NO: 90 | GUN2873.90.1 |
| SEQ ID NO: 91 | GUN2873.91.1 |
| SEQ ID NO: 92 | GUN2873.92.1 |
| SEQ ID NO: 93 | GUN2873.93.1 |
| SEQ ID NO: 94 | GUN2873.94.1 |
| SEQ ID NO: 95 | GUN2873.95.1 |
| SEQ ID NO: 96 | GUN2873.96.1 |
| SEQ ID NO: 97 | GUN2873.97.1 |
| SEQ ID NO: 98 | GUN2873.98.1 |
| SEQ ID NO: 99 | GUN2873.99.1 |
| SEQ ID NO: 100 | GUN2873.100.1 |
| SEQ ID NO: 101 | GUN2873.101.1 |
| SEQ ID NO: 102 | GUN2873.102.1 |
| SEQ ID NO: 103 | GUN2873.103.1 |
| SEQ ID NO: 104 | GUN2873.104.1 |
| SEQ ID NO: 105 | GUN2873.105.1 |
| SEQ ID NO: 106 | GUN2873.106.1 |
| SEQ ID NO: 107 | GUN2873.107.1 |
| SEQ ID NO: 108 | GUN2873.108.1 |
| SEQ ID NO: 109 | GUN2873.109.1 |
| SEQ ID NO: 110 | GUN2873.110.1 |
| SEQ ID NO: 111 | GUN2873.111.1 |
| SEQ ID NO: 112 | GUN2873.112.1 |
| SEQ ID NO: 113 | GUN2873.113.1 |
| SEQ ID NO: 114 | GUN2873.114.1 |
| SEQ ID NO: 115 | GUN2873.115.1 |
| SEQ ID NO: 116 | GUN2873.116.1 |
| SEQ ID NO: 117 | GUN2873.117.1 |

FIG. 1 (cont.)

| SEQ ID NO | Sequence Name |
|---|---|
| SEQ ID NO: 118 | GUN2873.118.1 |
| SEQ ID NO: 119 | GUN2873.119.1 |
| SEQ ID NO: 120 | GUN2873.120.1 |
| SEQ ID NO: 121 | GUN2873.121.1 |
| SEQ ID NO: 122 | GUN2873.122.1 |
| SEQ ID NO: 123 | GUN2873.123.1 |
| SEQ ID NO: 124 | GUN2873.124.1 |
| SEQ ID NO: 125 | GUN2873.125.1 |
| SEQ ID NO: 126 | GUN2873.126.1 |
| SEQ ID NO: 127 | GUN2873.127.1 |
| SEQ ID NO: 128 | GUN2873.128.1 |
| SEQ ID NO: 129 | GUN2873.129.1 |
| SEQ ID NO: 130 | GUN2873.130.1 |
| SEQ ID NO: 131 | GUN2873.131.1 |
| SEQ ID NO: 132 | GUN2873.132.1 |
| SEQ ID NO: 133 | GUN2873.133.1 |
| SEQ ID NO: 134 | GUN2873.134.1 |
| SEQ ID NO: 135 | GUN2873.135.1 |
| SEQ ID NO: 136 | GUN2873.136.1 |
| SEQ ID NO: 137 | GUN2873.137.1 |
| SEQ ID NO: 138 | GUN2873.138.1 |
| SEQ ID NO: 139 | GUN2873.139.1 |
| SEQ ID NO: 140 | GUN2873.140.1 |
| SEQ ID NO: 141 | GUN2873.141.1 |
| SEQ ID NO: 142 | GUN2873.142.1 |
| SEQ ID NO: 143 | GUN2873.143.1 |
| SEQ ID NO: 144 | GUN2873.144.1 |
| SEQ ID NO: 145 | GUN2873.145.1 |
| SEQ ID NO: 146 | GUN2873.146.1 |
| SEQ ID NO: 147 | GUN2873.147.1 |
| SEQ ID NO: 148 | GUN2873.148.1 |
| SEQ ID NO: 149 | GUN2873.149.1 |
| SEQ ID NO: 150 | GUN2873.150.1 |
| SEQ ID NO: 151 | GUN2873.151.1 |
| SEQ ID NO: 152 | GUN2873.152.1 |
| SEQ ID NO: 153 | GUN2873.153.1 |
| SEQ ID NO: 154 | GUN2873.154.1 |
| SEQ ID NO: 155 | GUN2873.155.1 |
| SEQ ID NO: 156 | GUN2873.156.1 |

FIG. 1 (cont.)

| SEQ ID NO | Sequence Name |
|---|---|
| SEQ ID NO: 157 | GUN2873.157.1 |
| SEQ ID NO: 158 | GUN2873.158.1 |
| SEQ ID NO: 159 | GUN2873.159.1 |
| SEQ ID NO: 160 | GUN2873.160.1 |
| SEQ ID NO: 161 | GUN2873.161.1 |
| SEQ ID NO: 162 | GUN2873.162.1 |
| SEQ ID NO: 163 | GUN2873.163.1 |
| SEQ ID NO: 164 | GUN2873.164.1 |
| SEQ ID NO: 165 | GUN2873.165.1 |
| SEQ ID NO: 166 | GUN2873.166.1 |
| SEQ ID NO: 167 | GUN2873.167.1 |
| SEQ ID NO: 168 | GUN2873.168.1 |
| SEQ ID NO: 169 | GUN2873.169.1 |
| SEQ ID NO: 170 | GUN2873.170.1 |
| SEQ ID NO: 171 | GUN2873.171.1 |
| SEQ ID NO: 172 | GUN2873.172.1 |
| SEQ ID NO: 173 | GUN2873.173.1 |
| SEQ ID NO: 174 | GUN2873.174.1 |
| SEQ ID NO: 175 | GUN2873.175.1 |
| SEQ ID NO: 176 | GUN2873.176.1 |
| SEQ ID NO: 177 | GUN2873.177.1 |
| SEQ ID NO: 178 | GUN2873.178.1 |
| SEQ ID NO: 179 | GUN2873.179.1 |
| SEQ ID NO: 180 | GUN2873.180.1 |
| SEQ ID NO: 181 | GUN2873.181.1 |
| SEQ ID NO: 182 | GUN2873.182.1 |
| SEQ ID NO: 183 | GUN2873.183.1 |
| SEQ ID NO: 184 | GUN2873.184.1 |
| SEQ ID NO: 185 | GUN2873.1.2 DNA |
| SEQ ID NO: 186 | GUN2873.2.1 DNA |
| SEQ ID NO: 187 | GUN2873.3.1 DNA |
| SEQ ID NO: 188 | GUN2873.4.1 DNA |
| SEQ ID NO: 189 | GUN2873.5.1 DNA |
| SEQ ID NO: 190 | GUN2873.6.1 DNA |
| SEQ ID NO: 191 | GUN2873.7.1 DNA |
| SEQ ID NO: 192 | GUN2873.8.1 DNA |
| SEQ ID NO: 193 | GUN2873.9.1 DNA |
| SEQ ID NO: 194 | GUN2873.10.1 DNA |
| SEQ ID NO: 195 | GUN2873.11.1 DNA |

FIG. 1 (cont.)

| SEQ ID NO | Sequence Name |
|---|---|
| SEQ ID NO: 196 | GUN2873.12.1 DNA |
| SEQ ID NO: 197 | GUN2873.13.1 DNA |
| SEQ ID NO: 198 | GUN2873.14.1 DNA |
| SEQ ID NO: 199 | GUN2873.15.1 DNA |
| SEQ ID NO: 200 | GUN2873.16.1 DNA |
| SEQ ID NO: 201 | GUN2873.17.1 DNA |
| SEQ ID NO: 202 | GUN2873.18.1 DNA |
| SEQ ID NO: 203 | GUN2873.19.1 DNA |
| SEQ ID NO: 204 | GUN2873.20.1 DNA |
| SEQ ID NO: 205 | GUN2873.21.1 DNA |
| SEQ ID NO: 206 | GUN2873.22.1 DNA |
| SEQ ID NO: 207 | GUN2873.23.1 DNA |
| SEQ ID NO: 208 | GUN2873.24.1 DNA |
| SEQ ID NO: 209 | GUN2873.25.1 DNA |
| SEQ ID NO: 210 | GUN2873.26.1 DNA |
| SEQ ID NO: 211 | GUN2873.27.1 DNA |
| SEQ ID NO: 212 | GUN2873.28.1 DNA |
| SEQ ID NO: 213 | GUN2873.29.1 DNA |
| SEQ ID NO: 214 | GUN2873.30.1 DNA |
| SEQ ID NO: 215 | GUN2873.31.1 DNA |
| SEQ ID NO: 216 | GUN2873.32.1 DNA |
| SEQ ID NO: 217 | GUN2873.33.1 DNA |
| SEQ ID NO: 218 | GUN2873.34.1 DNA |
| SEQ ID NO: 219 | GUN2873.35.1 DNA |
| SEQ ID NO: 220 | GUN2873.36.1 DNA |
| SEQ ID NO: 221 | GUN2873.37.1 DNA |
| SEQ ID NO: 222 | GUN2873.38.1 DNA |
| SEQ ID NO: 223 | GUN2873.39.1 DNA |
| SEQ ID NO: 224 | GUN2873.40.1 DNA |
| SEQ ID NO: 225 | GUN2873.41.1 DNA |
| SEQ ID NO: 226 | GUN2873.42.1 DNA |
| SEQ ID NO: 227 | GUN2873.43.1 DNA |
| SEQ ID NO: 228 | GUN2873.44.1 DNA |
| SEQ ID NO: 229 | GUN2873.45.1 DNA |
| SEQ ID NO: 230 | GUN2873.46.1 DNA |
| SEQ ID NO: 231 | GUN2873.47.1 DNA |
| SEQ ID NO: 232 | GUN2873.48.1 DNA |
| SEQ ID NO: 233 | GUN2873.49.1 DNA |
| SEQ ID NO: 234 | GUN2873.50.1 DNA |

FIG. 1 (cont.)

| SEQ ID NO | Sequence Name |
|---|---|
| SEQ ID NO: 235 | GUN2873.51.1 DNA |
| SEQ ID NO: 236 | GUN2873.52.1 DNA |
| SEQ ID NO: 237 | GUN2873.53.1 DNA |
| SEQ ID NO: 238 | GUN2873.54.1 DNA |
| SEQ ID NO: 239 | GUN2873.55.1 DNA |
| SEQ ID NO: 240 | GUN2873.56.1 DNA |
| SEQ ID NO: 241 | GUN2873.57.1 DNA |
| SEQ ID NO: 242 | GUN2873.58.1 DNA |
| SEQ ID NO: 243 | GUN2873.59.1 DNA |
| SEQ ID NO: 244 | GUN2873.60.1 DNA |
| SEQ ID NO: 245 | GUN2873.61.1 DNA |
| SEQ ID NO: 246 | GUN2873.62.1 DNA |
| SEQ ID NO: 247 | GUN2873.63.1 DNA |
| SEQ ID NO: 248 | GUN2873.64.1 DNA |
| SEQ ID NO: 249 | GUN2873.65.1 DNA |
| SEQ ID NO: 250 | GUN2873.66.1 DNA |
| SEQ ID NO: 251 | GUN2873.67.1 DNA |
| SEQ ID NO: 252 | GUN2873.68.1 DNA |
| SEQ ID NO: 253 | GUN2873.69.1 DNA |
| SEQ ID NO: 254 | GUN2873.70.1 DNA |
| SEQ ID NO: 255 | GUN2873.71.1 DNA |
| SEQ ID NO: 256 | GUN2873.72.1 DNA |
| SEQ ID NO: 257 | GUN2873.73.1 DNA |
| SEQ ID NO: 258 | GUN2873.74.1 DNA |
| SEQ ID NO: 259 | GUN2873.75.1 DNA |
| SEQ ID NO: 260 | GUN2873.76.1 DNA |
| SEQ ID NO: 261 | GUN2873.77.1 DNA |
| SEQ ID NO: 262 | GUN2873.78.1 DNA |
| SEQ ID NO: 263 | GUN2873.79.1 DNA |
| SEQ ID NO: 264 | GUN2873.80.1 DNA |
| SEQ ID NO: 265 | GUN2873.81.1 DNA |
| SEQ ID NO: 266 | GUN2873.82.1 DNA |
| SEQ ID NO: 267 | GUN2873.83.1 DNA |
| SEQ ID NO: 268 | GUN2873.84.1 DNA |
| SEQ ID NO: 269 | GUN2873.85.1 DNA |
| SEQ ID NO: 270 | GUN2873.86.1 DNA |
| SEQ ID NO: 271 | GUN2873.87.1 DNA |
| SEQ ID NO: 272 | GUN2873.88.1 DNA |
| SEQ ID NO: 273 | GUN2873.89.1  DNA |

FIG. 2

```
Consensus   MNNESQAKDSSLRMEPLEKEKGAASQGALSQIPPESYRTKSPAELLGAGKTRADLNFPDV    60
SEQ ID NO:  1    MNNESQAKDSSLRMEPLEKEKGAASQGALSQIPPESYRTKSPAELLGAGKTRADLNFPDV    60
SEQ ID NO:  12   MNNESQAKDSSLRMEPLEKEKGAASQGALSQIPPESYRTKSPAELLGAGKTRADLNFPDV    60
SEQ ID NO:  19   MNNESQAKDSSLRMEPLEKEKGAASQGALSQIPPESYRTKSPAELLGAGKTRADLNFPDV    60
SEQ ID NO:  20   MNNESQAKDSSLRMEPLEKEKGAASQGALSQIPPESYRTKSPAELLGAGKTRADLNFPDV    60
SEQ ID NO:  24   MNNESQAKDSSLRMEPLEKEKGAASQGALSQIPPESYRTKSPAELLGAGKTRADLNFPDV    60
SEQ ID NO:  30   MNNESQAKDSSLRMEPLEKEKGAASQGALSQIPPESYRTKSPAELLGAGKTRADLNFPDV    60
SEQ ID NO:  42   MNNESQAKDSSLRMEPLEKEKGAASQGALSQIPPESYRTKSPAELLGAGKTRADLNFPDV    60
SEQ ID NO:  45   MNNESQAKDSSLRMEPLEKEKGAASQGALSQIPPESYRTKSPAELLGAGKTRADLNFPDV    60
SEQ ID NO:  46   MNNESQAKDSSLRMEPLEKEKGAASQGALSQIPPESYRTKSPAELLGAGKTRADLNFPDV    60
SEQ ID NO:  50   MNNESQAKDSSLRMEPLEKEKGAASQGALSQIPPESYRTKSPAELLGAGKTRADLNFPDV    60
SEQ ID NO:  55   MNNESQAKDSSLRMEPLEKEKGAASQGALSQIPPESYRTKSPAELLGAGKTRADLNFPDV    60
SEQ ID NO:  57   MNNESQAKDSSLRMEPLEKEKGAASQGALSQIPPESYRTKSPAELLGAGKTRADLNFPDV    60

Consensus   KKDYELDNALIGQTVTSHGCVVKAPWVRKDFHTPGYWSEGYIKPCAAYLSYIKKDTPSG    120
SEQ ID NO:  1    KKDYELDNALIGQTVTSHGCVVKAPWVRKDFHTPGYWSEGYIKPCAAYLSYIKKDTPSG    120
SEQ ID NO:  12   KKDYELDNALIGQTVTSHGCVVKAPWVRKDFHTPGYWSEGYIKPCAAYLSYIKKDTPSG    120
SEQ ID NO:  19   KKDYELDNALIGQTVTSHGCVVKAPWVRKDFHTPGYWSEGYIKPCAAYLSYIKKDTPSG    120
SEQ ID NO:  20   KKDYELDNALIGQTVTSHGCVVKAPWVRKDFHTPGYWSEGYIKPCAAYLSYIKKDTPSG    120
SEQ ID NO:  24   KKDYELDNALIGQTVTSHGCVVKAPWVRKDFHTPGYWSEGYIKPCAAYLSYIKKDTPSG    120
SEQ ID NO:  30   KKDYELDNALIGQTVTSHGCVVKAPWVRKDFHTPGYWSEGYIKPCAAYLSYIKKDTPSG    120
SEQ ID NO:  42   KKDYELDNALIGQTVTSHGCVVKAPWVRKDFHTPGYWSEGYIKPCAAYLSYIKKDTPSG    120
SEQ ID NO:  45   KKDYELDNALIGQTVTSHGCVVKAPWVRKDFHTPGYWSEGYIKPCAAYLSYIKKDTPSG    120
SEQ ID NO:  46   KKDYELDNALIGQTVTSHGCVVKAPWVRKDFHTPGYWSEGYIKPCAAYLSYIKKDTPSG    120
SEQ ID NO:  50   KKDYELDNALIGQTVTSHGCVVKAPWVRKDFHTPGYWSEGYIKPCAAYLSYIKKDTPSG    120
SEQ ID NO:  55   KKDYELDNALIGQTVTSHGCVVKAPWVRKDFHTPGYWSEGYIKPCAAYLSYIKKDTPSG    120
SEQ ID NO:  57   KKDYELDNALIGQTVTSHGCVVKAPWVRKDFHTPGYWSEGYIKPCAAYLSYIKKDTPSG    120
```

FIG. 2 (cont.)

```
Consensus       IGYLSLQTVIEYMCNEAWSRW               261
SEQ ID NO: 1    IGYLSLQTVIEYMCNEAWSRW               261
SEQ ID NO: 12   IGYLSLQTVIEYMCNEAWSRW               261
SEQ ID NO: 19   IGYLSLQTVIEYMCNEAWSRW               261
SEQ ID NO: 20   IGYLSLQTVIEYMCNEAWSRW               261
SEQ ID NO: 24   IGYLSLQTVIEYMCNEAWSRW               261
SEQ ID NO: 30   IGYLSLQTVIEYMCNEAWSRW               261
SEQ ID NO: 42   IGYLSLQTVIEYMCNEAWSRW               261
SEQ ID NO: 45   IGYLSLQTVIEYMCNEAWSRW               261
SEQ ID NO: 46   IGYLSLQTVIEYMCNEAWSRW               261
SEQ ID NO: 50   IGYLSLQTVIEYMCNEAWSRW               261
SEQ ID NO: 55   IGYLSLQTVIEYMCNEAWSRW               261
SEQ ID NO: 57   IGYLSLQTVIEYMCNEAWSRW               261
```

FIG. 3A

Amino Acid Identity (Percent Homology)

| | SEQ ID NO: 1 | SEQ ID NO: 12 | SEQ ID NO: 19 | SEQ ID NO: 20 | SEQ ID NO: 24 | SEQ ID NO: 30 | SEQ ID NO: 42 | SEQ ID NO: 45 | SEQ ID NO: 46 | SEQ ID NO: 50 | SEQ ID NO: 55 | SEQ ID NO: 57 |
|---|---|---|---|---|---|---|---|---|---|---|---|---|
| SEQ ID NO: 1 | | 98.47 | 98.85 | 99.23 | 92.34 | 94.25 | 96.93 | 98.08 | 98.08 | 90.42 | 93.1 | 92.72 |
| SEQ ID NO: 12 | 98.47 | | 98.08 | 97.7 | 91.19 | 93.87 | 98.47 | 99.62 | 99.62 | 91.95 | 93.49 | 94.25 |
| SEQ ID NO: 19 | 98.85 | 98.08 | | 98.08 | 91.19 | 93.1 | 96.55 | 97.7 | 97.7 | 91.57 | 94.25 | 93.87 |
| SEQ ID NO: 20 | 99.23 | 97.7 | 98.08 | | 91.57 | 93.49 | 96.17 | 97.32 | 97.32 | 89.66 | 92.34 | 91.95 |
| SEQ ID NO: 24 | 92.34 | 91.19 | 91.19 | 91.57 | | 93.49 | 92.34 | 91.57 | 90.8 | 97.7 | 92.34 | 91.57 |
| SEQ ID NO: 30 | 94.25 | 93.87 | 93.1 | 93.49 | 93.49 | | 95.4 | 94.25 | 94.25 | 91.95 | 98.85 | 98.08 |
| SEQ ID NO: 42 | 96.93 | 98.47 | 96.55 | 96.17 | 92.34 | 95.4 | | 98.08 | 98.08 | 93.1 | 95.02 | 95.79 |
| SEQ ID NO: 45 | 98.08 | 99.62 | 97.7 | 97.32 | 91.57 | 94.25 | 98.08 | | 99.23 | 92.34 | 93.87 | 94.64 |
| SEQ ID NO: 46 | 98.08 | 99.62 | 97.7 | 97.32 | 90.8 | 94.25 | 98.08 | 99.23 | | 91.57 | 93.87 | 94.64 |
| SEQ ID NO: 50 | 90.42 | 91.95 | 91.57 | 89.66 | 97.7 | 91.95 | 93.1 | 92.34 | 91.57 | | 93.1 | 93.87 |
| SEQ ID NO: 55 | 93.1 | 93.49 | 94.25 | 92.34 | 92.34 | 98.85 | 95.02 | 93.87 | 93.87 | 93.1 | | 99.23 |
| SEQ ID NO: 57 | 92.72 | 94.25 | 93.87 | 91.95 | 91.57 | 98.08 | 95.79 | 94.64 | 94.64 | 93.87 | 99.23 | |

FIG. 3B

Amino Acid Identity (Percent Homology)

| | SEQ ID NO: 1 | SEQ ID NO: 174 | SEQ ID NO: 175 | SEQ ID NO: 176 | SEQ ID NO: 177 | SEQ ID NO: 178 | SEQ ID NO: 179 | SEQ ID NO: 180 | SEQ ID NO: 181 | SEQ ID NO: 182 | SEQ ID NO: 183 | SEQ ID NO: 184 |
|---|---|---|---|---|---|---|---|---|---|---|---|---|
| SEQ ID NO: 1 | | 81.609 | 59.779 | 64.945 | 86.26 | 87.405 | 66.667 | 68.635 | 66.544 | 67.279 | 67.528 | 59.63 |
| SEQ ID NO: 174 | 81.609 | | 61.624 | 65.314 | 77.481 | 77.099 | 65.934 | 65.314 | 64.706 | 64.338 | 65.314 | 58.889 |
| SEQ ID NO: 175 | 59.779 | 61.624 | | 59.058 | 59.779 | 60.517 | 60.507 | 60.145 | 61.011 | 60.145 | 60.507 | 73.897 |
| SEQ ID NO: 176 | 64.945 | 65.314 | 59.058 | | 63.1 | 63.469 | 67.033 | 67.037 | 67.897 | 66.421 | 67.037 | 61.091 |
| SEQ ID NO: 177 | 86.26 | 77.481 | 59.779 | 63.1 | | 87.405 | 64.103 | 66.421 | 65.441 | 65.074 | 65.314 | 59.41 |
| SEQ ID NO: 178 | 87.405 | 77.099 | 60.517 | 63.469 | 87.405 | | 65.568 | 66.421 | 65.809 | 65.441 | 64.945 | 61.624 |
| SEQ ID NO: 179 | 66.667 | 65.934 | 60.507 | 67.033 | 64.103 | 65.568 | | 71.324 | 70.696 | 70.849 | 70.588 | 59.273 |
| SEQ ID NO: 180 | 68.635 | 65.314 | 60.145 | 67.037 | 66.421 | 66.421 | 71.324 | | 94.444 | 92.593 | 82.9 | 59.273 |
| SEQ ID NO: 181 | 66.544 | 64.706 | 61.011 | 67.897 | 65.441 | 65.809 | 70.696 | 94.444 | | 89.299 | 80.741 | 60.145 |
| SEQ ID NO: 182 | 67.279 | 64.338 | 60.145 | 66.421 | 65.074 | 65.441 | 70.849 | 92.593 | 89.299 | | 82.222 | 59.273 |
| SEQ ID NO: 183 | 67.528 | 65.314 | 60.507 | 67.037 | 65.314 | 64.945 | 70.588 | 82.9 | 80.741 | 82.222 | | 61.091 |
| SEQ ID NO: 184 | 59.63 | 58.889 | 73.897 | 61.091 | 59.41 | 61.624 | 59.273 | 59.273 | 60.145 | 59.273 | 61.091 | |

SEQUENCE LISTING

```
Sequence total quantity: 273
SEQ ID NO: 1            moltype = AA  length = 261
FEATURE                 Location/Qualifiers
source                  1..261
                        mol_type = protein
                        organism = Myxococcus fulvus
SEQUENCE: 1
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 2            moltype = AA  length = 261
FEATURE                 Location/Qualifiers
REGION                  1..261
                        note = Synthetic
source                  1..261
                        mol_type = protein
                        organism = synthetic construct
SEQUENCE: 2
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEHTLTKK KGFTSRFTAS TEVKVGVSAG IFGCETSLEV TTGFSYSETI NEETTETWKK  180
TVAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 3            moltype = AA  length = 261
FEATURE                 Location/Qualifiers
REGION                  1..261
                        note = Synthetic
source                  1..261
                        mol_type = protein
                        organism = synthetic construct
SEQUENCE: 3
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEHTLTKK KGFTSRFTAS AEVKVGVSAG IFGCEASLEV TTGFSYGQDI NEETTETWKK  180
TVAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 4            moltype = AA  length = 261
FEATURE                 Location/Qualifiers
REGION                  1..261
                        note = Synthetic
source                  1..261
                        mol_type = protein
```

-continued

```
                          organism = synthetic construct
SEQUENCE: 4
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEHTLTKK KGFTSRFTAS TEVKVGASAG VFACETSLEV TTGFSYGQDI NEETTETWKK  180
TVAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 5              moltype = AA  length = 261
FEATURE                   Location/Qualifiers
REGION                    1..261
                          note = Synthetic
source                    1..261
                          mol_type = protein
                          organism = synthetic construct
SEQUENCE: 5
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEHTLTKK KGFTSRFTAS AEVKVGASAG VFACEASLEV TTGFSYGQDI NEETTETWKK  180
TVAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 6              moltype = AA  length = 261
FEATURE                   Location/Qualifiers
REGION                    1..261
                          note = Synthetic
source                    1..261
                          mol_type = protein
                          organism = synthetic construct
SEQUENCE: 6
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEHTLTKK KGFTSRFTVS AEVKAGASAG VFACEASLEV TTGFSYGQDI NEETTETWKK  180
TVAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 7              moltype = AA  length = 261
FEATURE                   Location/Qualifiers
REGION                    1..261
                          note = Synthetic
source                    1..261
                          mol_type = protein
                          organism = synthetic construct
SEQUENCE: 7
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSEEHTLTKK KGFTSRFTVS AEVKAGASAG VFACEASLEV TTGFSYGQDI NEETEETWKK  180
TVAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 8              moltype = AA  length = 261
FEATURE                   Location/Qualifiers
REGION                    1..261
                          note = Synthetic
source                    1..261
                          mol_type = protein
                          organism = synthetic construct
SEQUENCE: 8
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSEEHTLTKK KGFSRQFTVS AEVKAGASAG VFACETSLEV TTGFSYGQDI NEETEETWKK  180
TVTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 9              moltype = AA  length = 261
FEATURE                   Location/Qualifiers
REGION                    1..261
                          note = Synthetic
source                    1..261
                          mol_type = protein
                          organism = synthetic construct
SEQUENCE: 9
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSEEHTLTKK KGFSRQFTVS AEVKAGASAG VFACETSLEV TTGFSYGQDI NEETEETDTT  180
TVTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 10             moltype = AA  length = 261
```

```
FEATURE              Location/Qualifiers
REGION               1..261
                     note = Synthetic
source               1..261
                     mol_type = protein
                     organism = synthetic construct
SEQUENCE: 10
MNNESQAKDS SLRMEPLEKE KGAAGQGALS QIPPESYRTK SPAELLGAGK TRADLNFPDV  60
KNDYALDNYL IGQTVTSNGC VVKAPWVRKD FNTPGYWSEG YIKPCAAYLS YIKKDTIPSG  120
TSEEHTLTKK KGFSRQFTVS AEVKAGASAG VFACETSLEV TTGFSYGQDI NEETEETDTT  180
TVTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 11          moltype = AA  length = 261
FEATURE              Location/Qualifiers
REGION               1..261
                     note = Synthetic
source               1..261
                     mol_type = protein
                     organism = synthetic construct
SEQUENCE: 11
MNNESQAKDS SLRMEPLEKE KGAAGQGALS QIPPESYRTK SPAELLGAGK TRADLNFPDT  60
KNDYALDNYL IGQTVTSNGC VVKAPWVRKD FNTPGYWSEG YIKPCAAYLS YIKKDTIPSG  120
TSEEHTLTKK KGFSRQFTVS AEVKAGASAG VFACETSLEV TTGFSYGQDI NEETEETDTT  180
TVTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 12          moltype = AA  length = 261
FEATURE              Location/Qualifiers
REGION               1..261
                     note = Synthetic
source               1..261
                     mol_type = protein
                     organism = synthetic construct
SEQUENCE: 12
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYSEDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 13          moltype = AA  length = 261
FEATURE              Location/Qualifiers
REGION               1..261
                     note = Synthetic
source               1..261
                     mol_type = protein
                     organism = synthetic construct
SEQUENCE: 13
MNNESQAKDS SLRMEPLEKE KGAAGQGALS QIPPESYRTK SPAELLGAGK TRADLNFPDT  60
KNDYALDNAY IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYSEDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 14          moltype = AA  length = 261
FEATURE              Location/Qualifiers
REGION               1..261
                     note = Synthetic
source               1..261
                     mol_type = protein
                     organism = synthetic construct
SEQUENCE: 14
MNNESQAKDS SLRMEPLEKE KGAAGQGALS QIPPESYRTK SPAELLGAGK TRADLNFPDT  60
KNDYALDNAY IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYSEDI NEETTETDTT  180
TLAGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 15          moltype = AA  length = 261
FEATURE              Location/Qualifiers
REGION               1..261
                     note = Synthetic
source               1..261
                     mol_type = protein
                     organism = synthetic construct
SEQUENCE: 15
MNNESQAKDS SLRMEPLEKE KGAAGQGALS QIPPESYRTK SPAELLGAGK TRADLNFPDT  60
KNDYALDNAY IGQTVTSNGC VVKAPWVRKD FNTPGYWSEG YIKPCAAYLS YIKKDTIPSG  120
```

-continued

```
TSIEYSLTKK KGFSRQFTVS AEVKVGISAG VFGCETSLEV TTGFSYSEDI NEETTETDTT    180
TLAGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 16          moltype = AA   length = 261
FEATURE                Location/Qualifiers
REGION                 1..261
                       note = Synthetic
source                 1..261
                       mol_type = protein
                       organism = synthetic construct
SEQUENCE: 16
MNNESQAKDS SLRMEPLEKE KGAAGQGALS QIPPESYRTK SPAELLGAGK TRADLNFPDT    60
KNDYALDNAY IGQTVTSNGC VVKAPWVRKD FNTPGYWSET YIKPCAAYLS YIKKDTIPSG    120
TSIEYSLTKK KGFSRQFTVS AEVKVGISAG VFGCETSLEV TTGFSYSEDI NEETTETDTT    180
TLAGPQDYWT FQPVLLYAWK VNANALSYMS PKPSLYYTSG KTTYIFSPVF RNSPSTIDKD    240
IGYLSLQRNV LYMCNEAWSR W                                             261

SEQ ID NO: 17          moltype = AA   length = 261
FEATURE                Location/Qualifiers
REGION                 1..261
                       note = Synthetic
source                 1..261
                       mol_type = protein
                       organism = synthetic construct
SEQUENCE: 17
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG    120
TSIEHTLTKK KGFSRQFTAS TEVKVGVSAG IFGCETSLEV TTGFSYSETI NEETTETWKK    180
TLTGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 18          moltype = AA   length = 261
FEATURE                Location/Qualifiers
REGION                 1..261
                       note = Synthetic
source                 1..261
                       mol_type = protein
                       organism = synthetic construct
SEQUENCE: 18
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG    120
TSIEYSLTKK KGFTSRFTAS TEVKVGVSAG IFGCETSLEV TTGFSYSETI NEETTETWKK    180
TLTGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 19          moltype = AA   length = 261
FEATURE                Location/Qualifiers
REGION                 1..261
                       note = Synthetic
source                 1..261
                       mol_type = protein
                       organism = synthetic construct
SEQUENCE: 19
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG    120
TSIEYSLTKK KGFSRQFTAS TEVKVGVSAG IFGCETSLEV TTGFSYGQDI NEETTETWKK    180
TLTGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 20          moltype = AA   length = 261
FEATURE                Location/Qualifiers
REGION                 1..261
                       note = Synthetic
source                 1..261
                       mol_type = protein
                       organism = synthetic construct
SEQUENCE: 20
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG    120
TSIEYSLTKK KGFSRQFTAS TEVKVGVSAG IFGCETSLEV TTGFSYSETI NEETTETWKK    180
TVAGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 21          moltype = AA   length = 261
FEATURE                Location/Qualifiers
REGION                 1..261
                       note = Synthetic
source                 1..261
```

-continued

```
                        mol_type = protein
                        organism = synthetic construct
SEQUENCE: 21
MNNESQAKDS SLRMEPLEKE KGAAGQGALS QIPPESYRTK SPAELLGAGK TRADLNFPDV     60
KNDYELDNAL IGQTVTSNGC VVKAPWVRKD FNTPGYWSEG YIKPCAAYLS YIKKDTIPQN    120
VTTTLSYQLT KGHTRSFETS VNAKYSVGAN IDIVNVGSEI STGFTRSESW STTQSFTDTT    180
EMKGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 22           moltype = AA   length = 261
FEATURE                 Location/Qualifiers
REGION                  1..261
                        note = Synthetic
source                  1..261
                        mol_type = protein
                        organism = synthetic construct
SEQUENCE: 22
MNNESQAKDS SLRMEPLEKE KGAAGQGALS QIPPESYRTK SPAELLGAGK TRADLNFPDV     60
KNDYELDNAL IGQTVTSNGC VVKAPWVRKD FNTPGYWSEG YIKPCAAYLS YIKKDTIPNQ    120
VDLQHQVTQK SGLTSSFTTE VKSSYSVGAK IDIVNVGSSI STGFSQTQSW SQERDESWTT    180
TLHGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 23           moltype = AA   length = 261
FEATURE                 Location/Qualifiers
REGION                  1..261
                        note = Synthetic
source                  1..261
                        mol_type = protein
                        organism = synthetic construct
SEQUENCE: 23
MNNESQAKDS SLRMEPLEKE KGAAGQGALS QIPPESYRTK SPAELLGAGK TRADLNFPDV     60
KNDYELDNAL IGQTVTSNGC VVKAPWVRKD FNTPGYWSEG YIKPCAAYLS YIKKDTYPSG    120
ATQHYTTTQT VGLTETFTKE VKASYSVGAN IDIVNVGSSI ETGFSRSSSW SQQTIQSWTT    180
TLQGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 24           moltype = AA   length = 261
FEATURE                 Location/Qualifiers
REGION                  1..261
                        note = Synthetic
source                  1..261
                        mol_type = protein
                        organism = synthetic construct
SEQUENCE: 24
MNNESQAKDS SLRMEPLEKE KGAAGQGALS QIPPESYRTK SPAELLGAGK TRADLNFPDV     60
KNDYELDNAL IGQTVTSNGC VVKAPWVRKD FNTPGYWSEG YIKPCAAYLS YIKKDTVPSG    120
VQEGYTLRKK KGFSRQFTTS TEVKSSVTAG FLACEATLEV TTSFSYSETI EEEFEETWTK    180
TLTGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 25           moltype = AA   length = 258
FEATURE                 Location/Qualifiers
REGION                  1..258
                        note = Synthetic
source                  1..258
                        mol_type = protein
                        organism = synthetic construct
SEQUENCE: 25
MNNESQAKDS SLRMEPLEKE KGAAGQGALS QIPPESYRTK SPAELLGAGK TRADLNFPDV     60
KNDYELDNAL IGQTVTSNGC VVKAPWVRKD FNTPGYWSEG YIKPCAAYLS YIKKDTIPGD    120
ETHTFRKFKG FTTRFDTSIS ITAGVSGGVF GCNASLEVTT EFSYGQEITE QTEETWTSTI    180
YAQDYWTFQP VLLYAWKVNA NALSYMSPKP SLYYTSGKTT YIFSPVFRNS PSTIDKDIGY    240
LSLQTVIEYM CNEAWSRW                                                 258

SEQ ID NO: 26           moltype = AA   length = 260
FEATURE                 Location/Qualifiers
REGION                  1..260
                        note = Synthetic
source                  1..260
                        mol_type = protein
                        organism = synthetic construct
SEQUENCE: 26
MNNESQAKDS SLRMEPLEKE KGAAGQGALS QIPPESYRTK SPAELLGAGK TRADLNFPDV     60
KNDYELDNAL IGQTVTSNGC VVKAPWVRKD FNTPGYWSEG YIKPCAAYLS YIKKDTVPGT    120
MEKTLEKKNG YSSRFQTSVE IKAGLSAGIF GCNASLEVTT GFTYEQTITS ETTETWKETL    180
TSGPQDYWTF QPVLLYAWKV NANALSYMSP KPSLYYTSGK TTYIFSPVFR NSPSTIDKDI    240
GYLSLQTVIE YMCNEAWSRW                                               260
```

-continued

```
SEQ ID NO: 27          moltype = AA  length = 258
FEATURE                Location/Qualifiers
REGION                 1..258
                       note = Synthetic
source                 1..258
                       mol_type = protein
                       organism = synthetic construct
SEQUENCE: 27
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTLAGT   120
EEHTLRKFKG YTSRFTASVE VKASASAGIF GCEASLEVTT GFSYGEEITE EKEETWKTTV   180
APQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 28          moltype = AA  length = 258
FEATURE                Location/Qualifiers
REGION                 1..258
                       note = Synthetic
source                 1..258
                       mol_type = protein
                       organism = synthetic construct
SEQUENCE: 28
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTLSGT   120
SEHTLRKLKG YTSRFNVSAE LKAGIKAGIF GCEASLEVTT GFSYGEDISQ ETEETWKTTV   180
APQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 29          moltype = AA  length = 261
FEATURE                Location/Qualifiers
REGION                 1..261
                       note = Synthetic
source                 1..261
                       mol_type = protein
                       organism = synthetic construct
SEQUENCE: 29
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPQN   120
ATQHYTTTQT VGLTETFTKE VKASYSVGAN IDIVNVGSSI ETGFSRSSSW SQQTIQSWTT   180
TLQGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 30          moltype = AA  length = 261
FEATURE                Location/Qualifiers
REGION                 1..261
                       note = Synthetic
source                 1..261
                       mol_type = protein
                       organism = synthetic construct
SEQUENCE: 30
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
VQESYSLSKK KGFTRQFTTS ASVTSSVSAG IFGCEASLEV TTGFSYSETI NEETTETWTR   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 31          moltype = AA  length = 261
FEATURE                Location/Qualifiers
REGION                 1..261
                       note = Synthetic
source                 1..261
                       mol_type = protein
                       organism = synthetic construct
SEQUENCE: 31
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPDG   120
TSSSHTFEKK KGYSSETSVS TEVKASVGVN ILGCDASMEV TTGFTYTQGI SSETTESWTD   180
TVTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 32          moltype = AA  length = 258
FEATURE                Location/Qualifiers
REGION                 1..258
                       note = Synthetic
source                 1..258
                       mol_type = protein
                       organism = synthetic construct
SEQUENCE: 32
MNNESQAKDS SLRMEPLEKE KGAAGQGALS QIPPESYRTK SPAELLGAGK TRADLNFPDV    60
```

-continued

```
KNDYELDNAL IGQTVTSNGC VVKAPWVRKD FNTPGYWSEG YIKPCAAYLS YIKKDTLSGT    120
EEHTLRKFKG YTSRFTASVE VKASASAGIF GCETSLEVTT GFSYGQEITD EKEETWKTTV    180
APQDYWTFQP VLLYAWKVNA NALSYMSPKP SLYYTSGKTT YIFSPVFRNS PSTIDKDIGY    240
LSLQTVIEYM CNEAWSRW                                                  258

SEQ ID NO: 33            moltype = AA   length = 261
FEATURE                  Location/Qualifiers
REGION                   1..261
                         note = Synthetic
source                   1..261
                         mol_type = protein
                         organism = synthetic construct
SEQUENCE: 33
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPQQ    120
VTQTRSYQLT KGHTQSFTTS VSAKYSVGAK IDIVNIGSEI STGFSQTESW STTQTFTEST    180
QLTGPQDYWT FQPVLLYAWK VNANALSYMS PKPSLYYTSG KTTYIFSPVF RNSPSTIDKD    240
IGYLSLQTVI EYMCNEAWSR W                                             261

SEQ ID NO: 34            moltype = AA   length = 258
FEATURE                  Location/Qualifiers
REGION                   1..258
                         note = Synthetic
source                   1..258
                         mol_type = protein
                         organism = synthetic construct
SEQUENCE: 34
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTLAGT    120
SEHTLRKLRG YTSRFNVSAE VKAGVKGGIL GCEASLEVTT GFSYGQEITQ EAEETWKTTV    180
SPQDYWTFQP VLLYAWKVNA NALSYMSPKP SLYYTSGKTT YIFSPVFRNS PSTIDKDIGY    240
LSLQTVIEYM CNEAWSRW                                                  258

SEQ ID NO: 35            moltype = AA   length = 258
FEATURE                  Location/Qualifiers
REGION                   1..258
                         note = Synthetic
source                   1..258
                         mol_type = protein
                         organism = synthetic construct
SEQUENCE: 35
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVVGT    120
VEQTMEKKKG FTSRFNASTE IKASASAGFF GCEASLEVTT GFEYEETVTS ETTHTWKQTL    180
TEQDYWTFQP VLLYAWKVNA NALSYMSPKP SLYYTSGKTT YIFSPVFRNS PSTIDKDIGY    240
LSLQTVIEYM CNEAWSRW                                                  258

SEQ ID NO: 36            moltype = AA   length = 257
FEATURE                  Location/Qualifiers
REGION                   1..257
                         note = Synthetic
source                   1..257
                         mol_type = protein
                         organism = synthetic construct
SEQUENCE: 36
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTLGTE    120
EHTLRKFKGF TSRFTASMEV KAGVKAGIFG CEASLEVTTG YSYGEDITEE KEEIWKTTVS    180
PQDYWTFQPV LLYAWKVNAN ALSYMSPKPS LYYTSGKTTY IFSPVFRNSP STIDKDIGYL    240
SLQTVIEYMC NEAWSRW                                                   257

SEQ ID NO: 37            moltype = AA   length = 259
FEATURE                  Location/Qualifiers
REGION                   1..259
                         note = Synthetic
source                   1..259
                         mol_type = protein
                         organism = synthetic construct
SEQUENCE: 37
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVVGT    120
QEHELTKKKG YSTTFTASTS LKSSISGGIG ECEASFEVTT EFSYSQNSYE EKSETWTTTL    180
TGPQDYWTFQ PVLLYAWKVN ANALSYMSPK PSLYYTSGKT TYIFSPVFRN SPSTIDKDIG    240
YLSLQTVIEY MCNEAWSRW                                                 259

SEQ ID NO: 38            moltype = AA   length = 261
FEATURE                  Location/Qualifiers
REGION                   1..261
                         note = Synthetic
```

```
source                     1..261
                           mol_type = protein
                           organism = synthetic construct
SEQUENCE: 38
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTLDVA  120
DTVGQVLNMR KGFSNRFTAS KALKALISEG VAGCDSCHEV TTKFDYILET IKDESKQPFS  180
DPVSVVPSQL CQPVLLYAWK VNANALSYMS PKPSLYYTSG KTTYIFSPVF RNSPSTIDKD  240
IGYLSLQTVI EYMCNEAWSR W                                           261

SEQ ID NO: 39             moltype = AA  length = 261
FEATURE                   Location/Qualifiers
REGION                    1..261
                          note = Synthetic
source                    1..261
                          mol_type = protein
                          organism = synthetic construct
SEQUENCE: 39
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYSEDI NEETTETWKK  180
VATGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 40             moltype = AA  length = 261
FEATURE                   Location/Qualifiers
REGION                    1..261
                          note = Synthetic
source                    1..261
                          mol_type = protein
                          organism = synthetic construct
SEQUENCE: 40
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYGQDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 41             moltype = AA  length = 261
FEATURE                   Location/Qualifiers
REGION                    1..261
                          note = Synthetic
source                    1..261
                          mol_type = protein
                          organism = synthetic construct
SEQUENCE: 41
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYGQDI NEETTETWKK  180
VATGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 42             moltype = AA  length = 261
FEATURE                   Location/Qualifiers
REGION                    1..261
                          note = Synthetic
source                    1..261
                          mol_type = protein
                          organism = synthetic construct
SEQUENCE: 42
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
VQESYSLTKK KGFSRQFTVS AEVKVGVSAG IFGCETSLEV TTGFSYSEDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 43             moltype = AA  length = 261
FEATURE                   Location/Qualifiers
REGION                    1..261
                          note = Synthetic
source                    1..261
                          mol_type = protein
                          organism = synthetic construct
SEQUENCE: 43
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AESKVGVSAG IFGCETSLEV TTGFSYSEDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261
```

-continued

```
SEQ ID NO: 44              moltype = AA   length = 261
FEATURE                    Location/Qualifiers
REGION                     1..261
                           note = Synthetic
source                     1..261
                           mol_type = protein
                           organism = synthetic construct
SEQUENCE: 44
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVTVGVSAG IFGCETSLEV TTGFSYSEDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 45              moltype = AA   length = 261
FEATURE                    Location/Qualifiers
REGION                     1..261
                           note = Synthetic
source                     1..261
                           mol_type = protein
                           organism = synthetic construct
SEQUENCE: 45
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCEASLEV TTGFSYSEDI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 46              moltype = AA   length = 261
FEATURE                    Location/Qualifiers
REGION                     1..261
                           note = Synthetic
source                     1..261
                           mol_type = protein
                           organism = synthetic construct
SEQUENCE: 46
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYSEDI NEETTETWKR  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 47              moltype = AA   length = 261
FEATURE                    Location/Qualifiers
REGION                     1..261
                           note = Synthetic
source                     1..261
                           mol_type = protein
                           organism = synthetic construct
SEQUENCE: 47
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
VQEGYTLRKK KGFSRQFTVS AEVKSSVTAG FLACEATLEV TTSFSYSEDI EEEFEETWTK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 48              moltype = AA   length = 261
FEATURE                    Location/Qualifiers
REGION                     1..261
                           note = Synthetic
source                     1..261
                           mol_type = protein
                           organism = synthetic construct
SEQUENCE: 48
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
VQEGYTLRKK KGFSRQFTTS TEVKSSVTAG FLACEATLEV TTSFSYGQDI EEEFEETWTK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 49              moltype = AA   length = 261
FEATURE                    Location/Qualifiers
REGION                     1..261
                           note = Synthetic
source                     1..261
                           mol_type = protein
                           organism = synthetic construct
SEQUENCE: 49
```

```
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
VQEGYTLRKK KGFSRQFTTS TEVKSSVTAG FLACEATLEV TTSFSYSETI EEEFEETWTK   180
TVAGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 50            moltype = AA   length = 261
FEATURE                  Location/Qualifiers
REGION                   1..261
                         note = Synthetic
source                   1..261
                         mol_type = protein
                         organism = synthetic construct
SEQUENCE: 50
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQEGYTLRKK KGFSRQFTVS AEVKSSVTAG FLACEATLEV TTSFSYGQDI EEEFEETWTK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 51            moltype = AA   length = 261
FEATURE                  Location/Qualifiers
REGION                   1..261
                         note = Synthetic
source                   1..261
                         mol_type = protein
                         organism = synthetic construct
SEQUENCE: 51
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQEGYTLRKK KGFSRQFTVS AEVKSSVTAG FLACEATLEV TTSFSYSEDI EEEFEETWTK   180
TVAGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 52            moltype = AA   length = 261
FEATURE                  Location/Qualifiers
REGION                   1..261
                         note = Synthetic
source                   1..261
                         mol_type = protein
                         organism = synthetic construct
SEQUENCE: 52
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
VQEGYTLRKK KGFSRQFTTS TEVKSSVTAG FLACEATLEV TTSFSYGQDI EEEFEETWTK   180
TVAGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 53            moltype = AA   length = 261
FEATURE                  Location/Qualifiers
REGION                   1..261
                         note = Synthetic
source                   1..261
                         mol_type = protein
                         organism = synthetic construct
SEQUENCE: 53
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQEGYTLRKK KGFSRQFTVS AEVKSSVTAG FLACEATLEV TTSFSYGQDI EEEFEETWTK   180
TVAGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 54            moltype = AA   length = 261
FEATURE                  Location/Qualifiers
REGION                   1..261
                         note = Synthetic
source                   1..261
                         mol_type = protein
                         organism = synthetic construct
SEQUENCE: 54
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQESYSLSKK KGFTRQFTVS ASVTSSVSAG IFGCEASLEV TTGFSYSEDI NEETTETWTR   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 55            moltype = AA   length = 261
FEATURE                  Location/Qualifiers
REGION                   1..261
```

-continued

```
                               note = Synthetic
source                         1..261
                               mol_type = protein
                               organism = synthetic construct
SEQUENCE: 55
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
VQESYSLSKK KGFTRQFTTS ASVTSSVSAG IFGCEASLEV TTGFSYGQDI NEETTETWTR   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 56              moltype = AA  length = 261
FEATURE                    Location/Qualifiers
REGION                     1..261
                           note = Synthetic
source                     1..261
                           mol_type = protein
                           organism = synthetic construct
SEQUENCE: 56
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
VQESYSLSKK KGFTRQFTTS ASVTSSVSAG IFGCEASLEV TTGFSYSETI NEETTETWTR   180
VATGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 57              moltype = AA  length = 261
FEATURE                    Location/Qualifiers
REGION                     1..261
                           note = Synthetic
source                     1..261
                           mol_type = protein
                           organism = synthetic construct
SEQUENCE: 57
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQESYSLSKK KGFTRQFTVS ASVTSSVSAG IFGCEASLEV TTGFSYGQDI NEETTETWTR   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 58              moltype = AA  length = 261
FEATURE                    Location/Qualifiers
REGION                     1..261
                           note = Synthetic
source                     1..261
                           mol_type = protein
                           organism = synthetic construct
SEQUENCE: 58
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQESYSLSKK KGFTRQFTVS ASVTSSVSAG IFGCEASLEV TTGFSYSEDI NEETTETWTR   180
TVAGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 59              moltype = AA  length = 261
FEATURE                    Location/Qualifiers
REGION                     1..261
                           note = Synthetic
source                     1..261
                           mol_type = protein
                           organism = synthetic construct
SEQUENCE: 59
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
VQESYSLSKK KGFTRQFTTS ASVTSSVSAG IFGCEASLEV TTGFSYGQDI NEETTETWTR   180
TVAGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 60              moltype = AA  length = 261
FEATURE                    Location/Qualifiers
REGION                     1..261
                           note = Synthetic
source                     1..261
                           mol_type = protein
                           organism = synthetic construct
SEQUENCE: 60
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPSG   120
VQESYSLSKK KGFTRQFTVS ASVTSSVSAG IFGCEASLEV TTGFSYGQDI NEETTETWTR   180
TVAGPQDYWT FQPVLLYAWK VNANALSYMS PKPSLYYTSG KTTYIFSPVF RNSPSTIDKD   240
```

-continued

```
IGYLSLQTVI EYMCNEAWSR W                                                                   261

SEQ ID NO: 61              moltype = AA   length = 261
FEATURE                    Location/Qualifiers
REGION                     1..261
                           note = Synthetic
source                     1..261
                           mol_type = protein
                           organism = synthetic construct
SEQUENCE: 61
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIEHTLTKK KGFTSQFTAS TEVKVGVSAG IFGCETSLEV TTGFSYSETI NEETTETWKK   180
TVAGPQDYWT FQPVLLYAWK VNANALSYMS PKPSLYYTSG KTTYIFSPVF RNSPSTIDKD   240
IGYLSLQTVI EYMCNEAWSR W                                                                   261

SEQ ID NO: 62              moltype = AA   length = 261
FEATURE                    Location/Qualifiers
REGION                     1..261
                           note = Synthetic
source                     1..261
                           mol_type = protein
                           organism = synthetic construct
SEQUENCE: 62
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIEHTLTKK KGFTSQFTAS AEVKVGVSAG IFGCEASLEV TTGFSYGQDI NEETTETWKK   180
TVAGPQDYWT FQPVLLYAWK VNANALSYMS PKPSLYYTSG KTTYIFSPVF RNSPSTIDKD   240
IGYLSLQTVI EYMCNEAWSR W                                                                   261

SEQ ID NO: 63              moltype = AA   length = 261
FEATURE                    Location/Qualifiers
REGION                     1..261
                           note = Synthetic
source                     1..261
                           mol_type = protein
                           organism = synthetic construct
SEQUENCE: 63
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIEHTLTKK KGFTSQFTAS AEVKVGASAG VFACEASLEV TTGFSYGQDI NEETTETWKK   180
TVAGPQDYWT FQPVLLYAWK VNANALSYMS PKPSLYYTSG KTTYIFSPVF RNSPSTIDKD   240
IGYLSLQTVI EYMCNEAWSR W                                                                   261

SEQ ID NO: 64              moltype = AA   length = 261
FEATURE                    Location/Qualifiers
REGION                     1..261
                           note = Synthetic
source                     1..261
                           mol_type = protein
                           organism = synthetic construct
SEQUENCE: 64
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG   120
TSIEHTLTKK KGFTSQFTVS AEVKAGASAG VFACEASLEV TTGFSYGQDI NEETTETWKK   180
TVAGPQDYWT FQPVLLYAWK VNANALSYMS PKPSLYYTSG KTTYIFSPVF RNSPSTIDKD   240
IGYLSLQTVI EYMCNEAWSR W                                                                   261

SEQ ID NO: 65              moltype = AA   length = 261
FEATURE                    Location/Qualifiers
REGION                     1..261
                           note = Synthetic
source                     1..261
                           mol_type = protein
                           organism = synthetic construct
SEQUENCE: 65
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG   120
TSEEHTLTKK KGFTSQFTVS AEVKAGASAG VFACEASLEV TTGFSYGQDI NEETEETWKK   180
TVAGPQDYWT FQPVLLYAWK VNANALSYMS PKPSLYYTSG KTTYIFSPVF RNSPSTIDKD   240
IGYLSLQTVI EYMCNEAWSR W                                                                   261

SEQ ID NO: 66              moltype = AA   length = 261
FEATURE                    Location/Qualifiers
REGION                     1..261
                           note = Synthetic
source                     1..261
                           mol_type = protein
                           organism = synthetic construct
```

-continued

```
SEQUENCE: 66
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSEEHTLTKK KGFSRQFTVS AEVKAGASAG VFACETSLEV TTGFSYGQDI NEETEETDTK  180
TVTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 67             moltype = AA  length = 261
FEATURE                   Location/Qualifiers
REGION                    1..261
                          note = Synthetic
source                    1..261
                          mol_type = protein
                          organism = synthetic construct
SEQUENCE: 67
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGVSAG IFGCETSLEV TTGFSYSEDI NEETETDTK   180
TLAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 68             moltype = AA  length = 261
FEATURE                   Location/Qualifiers
REGION                    1..261
                          note = Synthetic
source                    1..261
                          mol_type = protein
                          organism = synthetic construct
SEQUENCE: 68
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPSG  120
TSIEYSLTKK KGFSRQFTVS AEVKVGISAG VFGCETSLEV TTGFSYSEDI NEETETDTK   180
TLAGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 69             moltype = AA  length = 261
FEATURE                   Location/Qualifiers
REGION                    1..261
                          note = Synthetic
source                    1..261
                          mol_type = protein
                          organism = synthetic construct
SEQUENCE: 69
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPQN  120
VTTTLSYQKT KGHTRQFTTS VNAKYSVGAN IDIVNVGSEI TTGFTRSESW STTQSFTDTK  180
EMKGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 70             moltype = AA  length = 261
FEATURE                   Location/Qualifiers
REGION                    1..261
                          note = Synthetic
source                    1..261
                          mol_type = protein
                          organism = synthetic construct
SEQUENCE: 70
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPNQ  120
VDLQHQVTKK SGLTSQFTTE VKSSYSVGAK IDIVNVGSEI TTGFSQTQSW SQERDESWTK  180
TLHGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 71             moltype = AA  length = 261
FEATURE                   Location/Qualifiers
REGION                    1..261
                          note = Synthetic
source                    1..261
                          mol_type = protein
                          organism = synthetic construct
SEQUENCE: 71
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTYPSG  120
ATQHYTTTKT VGLTEQFTKE VKASYSVGAN IDIVNVGSEI TTGFSRSSSW SQQTIQSWTK  180
TLQGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 72             moltype = AA  length = 258
FEATURE                   Location/Qualifiers
```

```
REGION                      1..258
                            note = Synthetic
source                      1..258
                            mol_type = protein
                            organism = synthetic construct
SEQUENCE: 72
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPGD   120
ETHTFRKFKG FTTQFTTSIS ITAGVSGGVF GCNASLEVTT EFSYGQEITE QTEETWTKTI   180
YAQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 73               moltype = AA   length = 260
FEATURE                     Location/Qualifiers
REGION                      1..260
                            note = Synthetic
source                      1..260
                            mol_type = protein
                            organism = synthetic construct
SEQUENCE: 73
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPGT   120
MEKTLEKKNG YSSQFTTSVE IKAGLSAGIF GCNASLEVTT GFTYEQTITS ETTETWKKTL   180
TSGPQDYWTF QPVLLYAWKV NANALSYMSP KPSLYYTSGK TTYIFSPVFR NSPSTIDKDI   240
GYLSLQTVIE YMCNEAWSRW                                               260

SEQ ID NO: 74               moltype = AA   length = 258
FEATURE                     Location/Qualifiers
REGION                      1..258
                            note = Synthetic
source                      1..258
                            mol_type = protein
                            organism = synthetic construct
SEQUENCE: 74
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTLAGT   120
EEHTLRKFKG YTSQFTASVE VKASASAGIF GCEASLEVTT GFSYGEEITE EKEETWKKTV   180
APQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 75               moltype = AA   length = 258
FEATURE                     Location/Qualifiers
REGION                      1..258
                            note = Synthetic
source                      1..258
                            mol_type = protein
                            organism = synthetic construct
SEQUENCE: 75
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTLSGT   120
SEHTLRKLKG YTSRFTVSAE LKAGIKAGIF GCEASLEVTT GFSYGEDISQ ETEETWKKTV   180
APQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 76               moltype = AA   length = 261
FEATURE                     Location/Qualifiers
REGION                      1..261
                            note = Synthetic
source                      1..261
                            mol_type = protein
                            organism = synthetic construct
SEQUENCE: 76
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPQN   120
ATQHYTTTKT VGLTEQFTKE VKASYSVGAN IDIVNVGSEI TTGFSRSSSW SQQTIQSWTK   180
TLQGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 77               moltype = AA   length = 261
FEATURE                     Location/Qualifiers
REGION                      1..261
                            note = Synthetic
source                      1..261
                            mol_type = protein
                            organism = synthetic construct
SEQUENCE: 77
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTIPDG   120
TSSSHTFEKK KGYSSQTTVS TEVKASVGVN ILGCDASMEV TTGFTYTQGI SSETTESWTK   180
```

-continued

```
TVTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 78              moltype = AA   length = 258
FEATURE                    Location/Qualifiers
REGION                     1..258
                           note = Synthetic
source                     1..258
                           mol_type = protein
                           organism = synthetic construct
SEQUENCE: 78
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTLSGT   120
EEHTLRKFKG YTSQFTASVE VKASASAGIF GCETSLEVTT GFSYGQEITD EKEETWKKTV   180
APQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 79              moltype = AA   length = 261
FEATURE                    Location/Qualifiers
REGION                     1..261
                           note = Synthetic
source                     1..261
                           mol_type = protein
                           organism = synthetic construct
SEQUENCE: 79
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPQQ   120
VTQTRSYQKT KGHTQQFTTS VSAKYSVGAK IDIVNIGSEI TTGFSQTESW STTQTFTESK   180
QLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 80              moltype = AA   length = 258
FEATURE                    Location/Qualifiers
REGION                     1..258
                           note = Synthetic
source                     1..258
                           mol_type = protein
                           organism = synthetic construct
SEQUENCE: 80
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTLAGT   120
SEHTLRKLRG YTSQFNVSAE VKAGVKGGIL GCEASLEVTT GFSYGQEITQ EAEETWKKTV   180
SPQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 81              moltype = AA   length = 258
FEATURE                    Location/Qualifiers
REGION                     1..258
                           note = Synthetic
source                     1..258
                           mol_type = protein
                           organism = synthetic construct
SEQUENCE: 81
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVVGT   120
VEQTMEKKKG FTSQFTASTE IKASASAGFF GCEASLEVTT GFEYEETVTS ETTHTWKKTL   180
TEQDYWTFQP VLLYAWKVNA NALSYMSPKP SLYYTSGKTT YIFSPVFRNS PSTIDKDIGY   240
LSLQTVIEYM CNEAWSRW                                                 258

SEQ ID NO: 82              moltype = AA   length = 257
FEATURE                    Location/Qualifiers
REGION                     1..257
                           note = Synthetic
source                     1..257
                           mol_type = protein
                           organism = synthetic construct
SEQUENCE: 82
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTLGTE   120
EHTLRKFKGF TSQFTASMEV KAGVKAGIFG CEASLEVTTG YSYGEDITEE KEEIWKKTVS   180
PQDYWTFQPV LLYAWKVNAN ALSYMSPKPS LYYTSGKTTY IFSPVFRNSP STIDKDIGYL   240
SLQTVIEYMC NEAWSRW                                                  257

SEQ ID NO: 83              moltype = AA   length = 259
FEATURE                    Location/Qualifiers
REGION                     1..259
                           note = Synthetic
source                     1..259
                           mol_type = protein
```

-continued

```
                        organism = synthetic construct
SEQUENCE: 83
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVVGT  120
QEHELTKKKG YSTQFTASTS LKSSISGGIG ECEASFEVTT EFSYSQNSYE EKSETWTKTL  180
TGPQDYWTFQ PVLLYAWKVN ANALSYMSPK PSLYYTSGKT TYIFSPVFRN SPSTIDKDIG  240
YLSLQTVIEY MCNEAWSRW                                               259

SEQ ID NO: 84           moltype = AA   length = 267
FEATURE                 Location/Qualifiers
REGION                  1..267
                        note = Synthetic
source                  1..267
                        mol_type = protein
                        organism = synthetic construct
SEQUENCE: 84
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTLDVA  120
DTVGQVLNKR KGFSNQFTAS KALKALISEG VAGCDSCHEV TTKFDYILET IKDESKQPFS  180
KPVSVVPSQL CQDYWTFQPV LLYAWKVNAN ALSYMSPKPS LYYTSGKTTY IFSPVFRNSP  240
STIDKDIGYL SLQTVIEYMC NEAWSRW                                      267

SEQ ID NO: 85           moltype = AA   length = 261
FEATURE                 Location/Qualifiers
REGION                  1..261
                        note = Synthetic
source                  1..261
                        mol_type = protein
                        organism = synthetic construct
SEQUENCE: 85
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTAK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 86           moltype = AA   length = 261
FEATURE                 Location/Qualifiers
REGION                  1..261
                        note = Synthetic
source                  1..261
                        mol_type = protein
                        organism = synthetic construct
SEQUENCE: 86
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRAFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 87           moltype = AA   length = 261
FEATURE                 Location/Qualifiers
REGION                  1..261
                        note = Synthetic
source                  1..261
                        mol_type = protein
                        organism = synthetic construct
SEQUENCE: 87
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFAAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 88           moltype = AA   length = 261
FEATURE                 Location/Qualifiers
REGION                  1..261
                        note = Synthetic
source                  1..261
                        mol_type = protein
                        organism = synthetic construct
SEQUENCE: 88
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLAV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 89           moltype = AA   length = 261
```

```
FEATURE                Location/Qualifiers
REGION                 1..261
                       note = Synthetic
source                 1..261
                       mol_type = protein
                       organism = synthetic construct
SEQUENCE: 89
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV ATGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 90          moltype = AA  length = 261
FEATURE                Location/Qualifiers
REGION                 1..261
                       note = Synthetic
source                 1..261
                       mol_type = protein
                       organism = synthetic construct
SEQUENCE: 90
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKA   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 91          moltype = AA  length = 261
FEATURE                Location/Qualifiers
REGION                 1..261
                       note = Synthetic
source                 1..261
                       mol_type = protein
                       organism = synthetic construct
SEQUENCE: 91
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTAPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 92          moltype = AA  length = 261
FEATURE                Location/Qualifiers
REGION                 1..261
                       note = Synthetic
source                 1..261
                       mol_type = protein
                       organism = synthetic construct
SEQUENCE: 92
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 93          moltype = AA  length = 261
FEATURE                Location/Qualifiers
REGION                 1..261
                       note = Synthetic
source                 1..261
                       mol_type = protein
                       organism = synthetic construct
SEQUENCE: 93
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPAG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 94          moltype = AA  length = 261
FEATURE                Location/Qualifiers
REGION                 1..261
                       note = Synthetic
source                 1..261
                       mol_type = protein
                       organism = synthetic construct
SEQUENCE: 94
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSA   120
```

```
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 95            moltype = AA   length = 261
FEATURE                  Location/Qualifiers
REGION                   1..261
                         note = Synthetic
source                   1..261
                         mol_type = protein
                         organism = synthetic construct
SEQUENCE: 95
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
ASIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 96            moltype = AA   length = 261
FEATURE                  Location/Qualifiers
REGION                   1..261
                         note = Synthetic
source                   1..261
                         mol_type = protein
                         organism = synthetic construct
SEQUENCE: 96
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TAIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 97            moltype = AA   length = 261
FEATURE                  Location/Qualifiers
REGION                   1..261
                         note = Synthetic
source                   1..261
                         mol_type = protein
                         organism = synthetic construct
SEQUENCE: 97
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSAEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 98            moltype = AA   length = 261
FEATURE                  Location/Qualifiers
REGION                   1..261
                         note = Synthetic
source                   1..261
                         mol_type = protein
                         organism = synthetic construct
SEQUENCE: 98
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIAYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 99            moltype = AA   length = 261
FEATURE                  Location/Qualifiers
REGION                   1..261
                         note = Synthetic
source                   1..261
                         mol_type = protein
                         organism = synthetic construct
SEQUENCE: 99
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIEASLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 100           moltype = AA   length = 261
FEATURE                  Location/Qualifiers
REGION                   1..261
                         note = Synthetic
source                   1..261
```

```
                              mol_type = protein
                              organism = synthetic construct
SEQUENCE: 100
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYALTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 101           moltype = AA   length = 261
FEATURE                  Location/Qualifiers
REGION                   1..261
                         note = Synthetic
source                   1..261
                         mol_type = protein
                         organism = synthetic construct
SEQUENCE: 101
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSATKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 102           moltype = AA   length = 261
FEATURE                  Location/Qualifiers
REGION                   1..261
                         note = Synthetic
source                   1..261
                         mol_type = protein
                         organism = synthetic construct
SEQUENCE: 102
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLAKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 103           moltype = AA   length = 261
FEATURE                  Location/Qualifiers
REGION                   1..261
                         note = Synthetic
source                   1..261
                         mol_type = protein
                         organism = synthetic construct
SEQUENCE: 103
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKA KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 104           moltype = AA   length = 261
FEATURE                  Location/Qualifiers
REGION                   1..261
                         note = Synthetic
source                   1..261
                         mol_type = protein
                         organism = synthetic construct
SEQUENCE: 104
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK AGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 105           moltype = AA   length = 261
FEATURE                  Location/Qualifiers
REGION                   1..261
                         note = Synthetic
source                   1..261
                         mol_type = protein
                         organism = synthetic construct
SEQUENCE: 105
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KAFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261
```

-continued

```
SEQ ID NO: 106          moltype = AA  length = 261
FEATURE                 Location/Qualifiers
REGION                  1..261
                        note = Synthetic
source                  1..261
                        mol_type = protein
                        organism = synthetic construct
SEQUENCE: 106
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGASRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 107          moltype = AA  length = 261
FEATURE                 Location/Qualifiers
REGION                  1..261
                        note = Synthetic
source                  1..261
                        mol_type = protein
                        organism = synthetic construct
SEQUENCE: 107
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFARQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 108          moltype = AA  length = 261
FEATURE                 Location/Qualifiers
REGION                  1..261
                        note = Synthetic
source                  1..261
                        mol_type = protein
                        organism = synthetic construct
SEQUENCE: 108
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSAQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 109          moltype = AA  length = 261
FEATURE                 Location/Qualifiers
REGION                  1..261
                        note = Synthetic
source                  1..261
                        mol_type = protein
                        organism = synthetic construct
SEQUENCE: 109
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQATAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 110          moltype = AA  length = 261
FEATURE                 Location/Qualifiers
REGION                  1..261
                        note = Synthetic
source                  1..261
                        mol_type = protein
                        organism = synthetic construct
SEQUENCE: 110
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAA TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 111          moltype = AA  length = 261
FEATURE                 Location/Qualifiers
REGION                  1..261
                        note = Synthetic
source                  1..261
                        mol_type = protein
                        organism = synthetic construct
SEQUENCE: 111
MNNESQAKDS SLRMEPLEKE KGAAGQGALS QIPPESYRTK SPAELLGAGK TRADLNFPDV   60
```

-continued

```
KNDYELDNAL IGQTVTSNGC VVKAPWVRKD FNTPGYWSEG YIKPCAAYLS YIKKDTVPSG 120
TSIEYSLTKK KGFSRQFTAS AEVKVGVSAG IFGCETSLEV TTGFSYSETI NEETTETWKK 180
TLTGPQDYWT FQPVLLYAWK VNANALSYMS PKPSLYYTSG KTTYIFSPVF RNSPSTIDKD 240
IGYLSLQTVI EYMCNEAWSR W                                          261

SEQ ID NO: 112          moltype = AA   length = 261
FEATURE                 Location/Qualifiers
REGION                  1..261
                        note = Synthetic
source                  1..261
                        mol_type = protein
                        organism = synthetic construct
SEQUENCE: 112
MNNESQAKDS SLRMEPLEKE KGAAGQGALS QIPPESYRTK SPAELLGAGK TRADLNFPDV 60
KNDYELDNAL IGQTVTSNGC VVKAPWVRKD FNTPGYWSEG YIKPCAAYLS YIKKDTVPSG 120
TSIEYSLTKK KGFSRQFTAS TAVKVGVSAG IFGCETSLEV TTGFSYSETI NEETTETWKK 180
TLTGPQDYWT FQPVLLYAWK VNANALSYMS PKPSLYYTSG KTTYIFSPVF RNSPSTIDKD 240
IGYLSLQTVI EYMCNEAWSR W                                          261

SEQ ID NO: 113          moltype = AA   length = 261
FEATURE                 Location/Qualifiers
REGION                  1..261
                        note = Synthetic
source                  1..261
                        mol_type = protein
                        organism = synthetic construct
SEQUENCE: 113
MNNESQAKDS SLRMEPLEKE KGAAGQGALS QIPPESYRTK SPAELLGAGK TRADLNFPDV 60
KNDYELDNAL IGQTVTSNGC VVKAPWVRKD FNTPGYWSEG YIKPCAAYLS YIKKDTVPSG 120
TSIEYSLTKK KGFSRQFTAS TEAKVGVSAG IFGCETSLEV TTGFSYSETI NEETTETWKK 180
TLTGPQDYWT FQPVLLYAWK VNANALSYMS PKPSLYYTSG KTTYIFSPVF RNSPSTIDKD 240
IGYLSLQTVI EYMCNEAWSR W                                          261

SEQ ID NO: 114          moltype = AA   length = 261
FEATURE                 Location/Qualifiers
REGION                  1..261
                        note = Synthetic
source                  1..261
                        mol_type = protein
                        organism = synthetic construct
SEQUENCE: 114
MNNESQAKDS SLRMEPLEKE KGAAGQGALS QIPPESYRTK SPAELLGAGK TRADLNFPDV 60
KNDYELDNAL IGQTVTSNGC VVKAPWVRKD FNTPGYWSEG YIKPCAAYLS YIKKDTVPSG 120
TSIEYSLTKK KGFSRQFTAS TEVAVGVSAG IFGCETSLEV TTGFSYSETI NEETTETWKK 180
TLTGPQDYWT FQPVLLYAWK VNANALSYMS PKPSLYYTSG KTTYIFSPVF RNSPSTIDKD 240
IGYLSLQTVI EYMCNEAWSR W                                          261

SEQ ID NO: 115          moltype = AA   length = 261
FEATURE                 Location/Qualifiers
REGION                  1..261
                        note = Synthetic
source                  1..261
                        mol_type = protein
                        organism = synthetic construct
SEQUENCE: 115
MNNESQAKDS SLRMEPLEKE KGAAGQGALS QIPPESYRTK SPAELLGAGK TRADLNFPDV 60
KNDYELDNAL IGQTVTSNGC VVKAPWVRKD FNTPGYWSEG YIKPCAAYLS YIKKDTVPSG 120
TSIEYSLTKK KGFSRQFTAS TEVKAGVSAG IFGCETSLEV TTGFSYSETI NEETTETWKK 180
TLTGPQDYWT FQPVLLYAWK VNANALSYMS PKPSLYYTSG KTTYIFSPVF RNSPSTIDKD 240
IGYLSLQTVI EYMCNEAWSR W                                          261

SEQ ID NO: 116          moltype = AA   length = 261
FEATURE                 Location/Qualifiers
REGION                  1..261
                        note = Synthetic
source                  1..261
                        mol_type = protein
                        organism = synthetic construct
SEQUENCE: 116
MNNESQAKDS SLRMEPLEKE KGAAGQGALS QIPPESYRTK SPAELLGAGK TRADLNFPDV 60
KNDYELDNAL IGQTVTSNGC VVKAPWVRKD FNTPGYWSEG YIKPCAAYLS YIKKDTVPSG 120
TSIEYSLTKK KGFSRQFTAS TEVKVAVSAG IFGCETSLEV TTGFSYSETI NEETTETWKK 180
TLTGPQDYWT FQPVLLYAWK VNANALSYMS PKPSLYYTSG KTTYIFSPVF RNSPSTIDKD 240
IGYLSLQTVI EYMCNEAWSR W                                          261

SEQ ID NO: 117          moltype = AA   length = 261
FEATURE                 Location/Qualifiers
REGION                  1..261
                        note = Synthetic
```

-continued

```
source                  1..261
                        mol_type = protein
                        organism = synthetic construct
SEQUENCE: 117
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGASAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 118          moltype = AA  length = 261
FEATURE                 Location/Qualifiers
REGION                  1..261
                        note = Synthetic
source                  1..261
                        mol_type = protein
                        organism = synthetic construct
SEQUENCE: 118
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVAAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 119          moltype = AA  length = 261
FEATURE                 Location/Qualifiers
REGION                  1..261
                        note = Synthetic
source                  1..261
                        mol_type = protein
                        organism = synthetic construct
SEQUENCE: 119
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAA IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 120          moltype = AA  length = 261
FEATURE                 Location/Qualifiers
REGION                  1..261
                        note = Synthetic
source                  1..261
                        mol_type = protein
                        organism = synthetic construct
SEQUENCE: 120
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG AFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 121          moltype = AA  length = 261
FEATURE                 Location/Qualifiers
REGION                  1..261
                        note = Synthetic
source                  1..261
                        mol_type = protein
                        organism = synthetic construct
SEQUENCE: 121
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IAGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 122          moltype = AA  length = 261
FEATURE                 Location/Qualifiers
REGION                  1..261
                        note = Synthetic
source                  1..261
                        mol_type = protein
                        organism = synthetic construct
SEQUENCE: 122
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFACETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261
```

-continued

```
SEQ ID NO: 123          moltype = AA  length = 261
FEATURE                 Location/Qualifiers
REGION                  1..261
                        note = Synthetic
source                  1..261
                        mol_type = protein
                        organism = synthetic construct
SEQUENCE: 123
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGAETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 124          moltype = AA  length = 261
FEATURE                 Location/Qualifiers
REGION                  1..261
                        note = Synthetic
source                  1..261
                        mol_type = protein
                        organism = synthetic construct
SEQUENCE: 124
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCATSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 125          moltype = AA  length = 261
FEATURE                 Location/Qualifiers
REGION                  1..261
                        note = Synthetic
source                  1..261
                        mol_type = protein
                        organism = synthetic construct
SEQUENCE: 125
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCEASLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 126          moltype = AA  length = 261
FEATURE                 Location/Qualifiers
REGION                  1..261
                        note = Synthetic
source                  1..261
                        mol_type = protein
                        organism = synthetic construct
SEQUENCE: 126
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETALEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 127          moltype = AA  length = 261
FEATURE                 Location/Qualifiers
REGION                  1..261
                        note = Synthetic
source                  1..261
                        mol_type = protein
                        organism = synthetic construct
SEQUENCE: 127
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSAEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 128          moltype = AA  length = 261
FEATURE                 Location/Qualifiers
REGION                  1..261
                        note = Synthetic
source                  1..261
                        mol_type = protein
                        organism = synthetic construct
SEQUENCE: 128
```

```
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEA TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                          261

SEQ ID NO: 129           moltype = AA  length = 261
FEATURE                  Location/Qualifiers
REGION                   1..261
                         note = Synthetic
source                   1..261
                         mol_type = protein
                         organism = synthetic construct
SEQUENCE: 129
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TAGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                          261

SEQ ID NO: 130           moltype = AA  length = 261
FEATURE                  Location/Qualifiers
REGION                   1..261
                         note = Synthetic
source                   1..261
                         mol_type = protein
                         organism = synthetic construct
SEQUENCE: 130
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTAFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                          261

SEQ ID NO: 131           moltype = AA  length = 261
FEATURE                  Location/Qualifiers
REGION                   1..261
                         note = Synthetic
source                   1..261
                         mol_type = protein
                         organism = synthetic construct
SEQUENCE: 131
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGASYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                          261

SEQ ID NO: 132           moltype = AA  length = 261
FEATURE                  Location/Qualifiers
REGION                   1..261
                         note = Synthetic
source                   1..261
                         mol_type = protein
                         organism = synthetic construct
SEQUENCE: 132
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFAYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                          261

SEQ ID NO: 133           moltype = AA  length = 261
FEATURE                  Location/Qualifiers
REGION                   1..261
                         note = Synthetic
source                   1..261
                         mol_type = protein
                         organism = synthetic construct
SEQUENCE: 133
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSASETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                          261

SEQ ID NO: 134           moltype = AA  length = 261
FEATURE                  Location/Qualifiers
REGION                   1..261
```

-continued

```
                                note = Synthetic
source                          1..261
                                mol_type = protein
                                organism = synthetic construct
SEQUENCE: 134
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYAETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 135           moltype = AA  length = 261
FEATURE                  Location/Qualifiers
REGION                   1..261
                         note = Synthetic
source                   1..261
                         mol_type = protein
                         organism = synthetic construct
SEQUENCE: 135
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSATI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 136           moltype = AA  length = 261
FEATURE                  Location/Qualifiers
REGION                   1..261
                         note = Synthetic
source                   1..261
                         mol_type = protein
                         organism = synthetic construct
SEQUENCE: 136
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSEAI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 137           moltype = AA  length = 261
FEATURE                  Location/Qualifiers
REGION                   1..261
                         note = Synthetic
source                   1..261
                         mol_type = protein
                         organism = synthetic construct
SEQUENCE: 137
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETA NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 138           moltype = AA  length = 261
FEATURE                  Location/Qualifiers
REGION                   1..261
                         note = Synthetic
source                   1..261
                         mol_type = protein
                         organism = synthetic construct
SEQUENCE: 138
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI AEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                           261

SEQ ID NO: 139           moltype = AA  length = 261
FEATURE                  Location/Qualifiers
REGION                   1..261
                         note = Synthetic
source                   1..261
                         mol_type = protein
                         organism = synthetic construct
SEQUENCE: 139
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NAETTETWKK  180
TLTGPQDYWT FQPVLLYAWK VNANALSYMS PKPSLYYTSG KTTYIFSPVF RNSPSTIDKD  240
```

-continued

```
IGYLSLQTVI EYMCNEAWSR W                                                   261

SEQ ID NO: 140          moltype = AA  length = 261
FEATURE                 Location/Qualifiers
REGION                  1..261
                        note = Synthetic
source                  1..261
                        mol_type = protein
                        organism = synthetic construct
SEQUENCE: 140
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEATTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                                   261

SEQ ID NO: 141          moltype = AA  length = 261
FEATURE                 Location/Qualifiers
REGION                  1..261
                        note = Synthetic
source                  1..261
                        mol_type = protein
                        organism = synthetic construct
SEQUENCE: 141
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEEATETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                                   261

SEQ ID NO: 142          moltype = AA  length = 261
FEATURE                 Location/Qualifiers
REGION                  1..261
                        note = Synthetic
source                  1..261
                        mol_type = protein
                        organism = synthetic construct
SEQUENCE: 142
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETAETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                                   261

SEQ ID NO: 143          moltype = AA  length = 261
FEATURE                 Location/Qualifiers
REGION                  1..261
                        note = Synthetic
source                  1..261
                        mol_type = protein
                        organism = synthetic construct
SEQUENCE: 143
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTATWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                                   261

SEQ ID NO: 144          moltype = AA  length = 261
FEATURE                 Location/Qualifiers
REGION                  1..261
                        note = Synthetic
source                  1..261
                        mol_type = protein
                        organism = synthetic construct
SEQUENCE: 144
MNNESQAKDS SLRMEPLEKE KGAAGQGALS QIPPESYRTK SPAELLGAGK TRADLNFPDV  60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTEAWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                                   261

SEQ ID NO: 145          moltype = AA  length = 261
FEATURE                 Location/Qualifiers
REGION                  1..261
                        note = Synthetic
source                  1..261
                        mol_type = protein
                        organism = synthetic construct
```

```
SEQUENCE: 145
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETAKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 146            moltype = AA  length = 261
FEATURE                   Location/Qualifiers
REGION                    1..261
                          note = Synthetic
source                    1..261
                          mol_type = protein
                          organism = synthetic construct
SEQUENCE: 146
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 147            moltype = AA  length = 261
FEATURE                   Location/Qualifiers
REGION                    1..261
                          note = Synthetic
source                    1..261
                          mol_type = protein
                          organism = synthetic construct
SEQUENCE: 147
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
ALTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 148            moltype = AA  length = 261
FEATURE                   Location/Qualifiers
REGION                    1..261
                          note = Synthetic
source                    1..261
                          mol_type = protein
                          organism = synthetic construct
SEQUENCE: 148
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TATGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 149            moltype = AA  length = 261
FEATURE                   Location/Qualifiers
REGION                    1..261
                          note = Synthetic
source                    1..261
                          mol_type = protein
                          organism = synthetic construct
SEQUENCE: 149
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLAGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 150            moltype = AA  length = 261
FEATURE                   Location/Qualifiers
REGION                    1..261
                          note = Synthetic
source                    1..261
                          mol_type = protein
                          organism = synthetic construct
SEQUENCE: 150
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTAPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 151            moltype = AA  length = 261
FEATURE                   Location/Qualifiers
```

-continued

```
REGION                  1..261
                        note = Synthetic
source                  1..261
                        mol_type = protein
                        organism = synthetic construct
SEQUENCE: 151
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGAQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 152          moltype = AA   length = 261
FEATURE                 Location/Qualifiers
REGION                  1..261
                        note = Synthetic
source                  1..261
                        mol_type = protein
                        organism = synthetic construct
SEQUENCE: 152
MNNESQAKDS SLRMEPLEKE KGAAGQGALS QIPPESYRTK SPAELLGAGK TRADLNFPDV    60
KNDYELDNAL IGQTVTSNGC VVKAPWVAKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 153          moltype = AA   length = 261
FEATURE                 Location/Qualifiers
REGION                  1..261
                        note = Synthetic
source                  1..261
                        mol_type = protein
                        organism = synthetic construct
SEQUENCE: 153
MNNESQAKDS SLRMEPLEKE KGAAGQGALS QIPPESYRTK SPAELLGAGK TRADLNFPDV    60
KNDYELDNAL IGQTVTSNGC VVKAPWVRKD FATPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 154          moltype = AA   length = 261
FEATURE                 Location/Qualifiers
REGION                  1..261
                        note = Synthetic
source                  1..261
                        mol_type = protein
                        organism = synthetic construct
SEQUENCE: 154
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNAPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 155          moltype = AA   length = 261
FEATURE                 Location/Qualifiers
REGION                  1..261
                        note = Synthetic
source                  1..261
                        mol_type = protein
                        organism = synthetic construct
SEQUENCE: 155
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTAGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                            261

SEQ ID NO: 156          moltype = AA   length = 261
FEATURE                 Location/Qualifiers
REGION                  1..261
                        note = Synthetic
source                  1..261
                        mol_type = protein
                        organism = synthetic construct
SEQUENCE: 156
MNNESQAKDS SLRMEPLEKE KGAAGQGALS QIPPESYRTK SPAELLGAGK TRADLNFPDV    60
KNDYELDNAL IGQTVTSNGC VVKAPWVRKD FNTPAYWSEG YIKPCAAYLS YIKKDTVPSG   120
TSIEYSLTKK KGFSRQFTAS TEVKVGVSAG IFGCETSLEV TTGFSYSETI NEETTETWKK   180
```

-continued

```
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 157            moltype = AA  length = 261
FEATURE                   Location/Qualifiers
REGION                    1..261
                          note = Synthetic
source                    1..261
                          mol_type = protein
                          organism = synthetic construct
SEQUENCE: 157
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG AIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDKD   240
IGYLSLQTVI EYMCNEAWSR W                                             261

SEQ ID NO: 158            moltype = AA  length = 261
FEATURE                   Location/Qualifiers
REGION                    1..261
                          note = Synthetic
source                    1..261
                          mol_type = protein
                          organism = synthetic construct
SEQUENCE: 158
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNAAALSYMS PKPSLYYTSG KTTYIFSPVF RNSPSTIDKD   240
IGYLSLQTVI EYMCNEAWSR W                                             261

SEQ ID NO: 159            moltype = AA  length = 261
FEATURE                   Location/Qualifiers
REGION                    1..261
                          note = Synthetic
source                    1..261
                          mol_type = protein
                          organism = synthetic construct
SEQUENCE: 159
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALAYMS PKPSLYYTSG KTTYIFSPVF RNSPSTIDKD   240
IGYLSLQTVI EYMCNEAWSR W                                             261

SEQ ID NO: 160            moltype = AA  length = 261
FEATURE                   Location/Qualifiers
REGION                    1..261
                          note = Synthetic
source                    1..261
                          mol_type = protein
                          organism = synthetic construct
SEQUENCE: 160
MNNDSQARES SLKMDPLDRD RGAAGQGALS QIPPDSYKTR SPADLLGAGR TKAELNFPEV   60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDRE   240
IGYLSLQTVI DYMCNDAWSK W                                             261

SEQ ID NO: 161            moltype = AA  length = 261
FEATURE                   Location/Qualifiers
REGION                    1..261
                          note = Synthetic
source                    1..261
                          mol_type = protein
                          organism = synthetic construct
SEQUENCE: 161
MQQDTNGRET TLKMDGLDRD RAGGANAGLS QIPPDSYKTR SPADLLGAGR TKAELNFPEV   60
KNDYELDNAL IGQTVTSNGC VVKAPWVRKD FNTPGYWSEG YIKPCAAYLS YIKKDTVPSG   120
TSIEYSLTKK KGFSRQFTAS TEVKVGVSAG IFGCETSLEV TTGFSYSETI NEETTETWKK   180
TLTGPQDYWT FQPVLLYAWK VNANALSYMS PKPSLYYTSG KTTYIFSPVF RNSPSTIDRE   240
IGYLSLQTVI DYMCNDAWSK W                                             261

SEQ ID NO: 162            moltype = AA  length = 261
FEATURE                   Location/Qualifiers
REGION                    1..261
                          note = Synthetic
source                    1..261
                          mol_type = protein
```

```
                        organism = synthetic construct
SEQUENCE: 162
MNNDSQAKES SLRMDPLDKD KGAAGQGALS QIPPDSYRTK SPADLLGAGK TRAELNFPEV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKE  240
IGYLSLQTVI DYMCNDAWSR W                                            261

SEQ ID NO: 163          moltype = AA  length = 261
FEATURE                 Location/Qualifiers
REGION                  1..261
                        note = Synthetic
source                  1..261
                        mol_type = protein
                        organism = synthetic construct
SEQUENCE: 163
MQQDTNGRET TLKMDGLDRD RAGGANAGLT NIPPDTYKSR TPADLLGAGR SKAELQFPEV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 164          moltype = AA  length = 261
FEATURE                 Location/Qualifiers
REGION                  1..261
                        note = Synthetic
source                  1..261
                        mol_type = protein
                        organism = synthetic construct
SEQUENCE: 164
MQQDTNGRET TLKMDGLDRD RAGGANAGLT NIPPDTYKSR TPADLLGAGR SKAELQFPEV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDRE  240
IGYLTLNTVI DYMCQDAWTK W                                            261

SEQ ID NO: 165          moltype = AA  length = 261
FEATURE                 Location/Qualifiers
REGION                  1..261
                        note = Synthetic
source                  1..261
                        mol_type = protein
                        organism = synthetic construct
SEQUENCE: 165
MQQDTNGRET TLKMDGLDRD RAGGANAGLS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDRE  240
IGYLTLNTVI DYMCQDAWTK W                                            261

SEQ ID NO: 166          moltype = AA  length = 261
FEATURE                 Location/Qualifiers
REGION                  1..261
                        note = Synthetic
source                  1..261
                        mol_type = protein
                        organism = synthetic construct
SEQUENCE: 166
MQQDTNGRET TLKMDGLDRD RAGGANAGLS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 167          moltype = AA  length = 261
FEATURE                 Location/Qualifiers
REGION                  1..261
                        note = Synthetic
source                  1..261
                        mol_type = protein
                        organism = synthetic construct
SEQUENCE: 167
MNNESQARDS SLKMEPLERE RGAAGQGALS QIPPESYKTR SPAELLGAGR TKADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDRD  240
IGYLSLQTVI EYMCNEAWSK W                                            261

SEQ ID NO: 168          moltype = AA  length = 261
```

-continued

```
FEATURE                 Location/Qualifiers
REGION                  1..261
                        note = Synthetic
source                  1..261
                        mol_type = protein
                        organism = synthetic construct
SEQUENCE: 168
MNNESQAKDS SLRMEPLEKE KGAAGQGALS QIPPESYRTK SPAELLGAGK TRADLNFPDV   60
KNDYELDNAL IGQTVTSNGC VVKAPWVRAD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG KTTYIFSPVF RNSPSTIDKD  240
IGYLSLQTVI EYMCNEAWSR W                                            261

SEQ ID NO: 169          moltype = AA  length = 261
FEATURE                 Location/Qualifiers
REGION                  1..261
                        note = Synthetic
source                  1..261
                        mol_type = protein
                        organism = synthetic construct
SEQUENCE: 169
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWA VNANALSYMS PKPSLYYTSG KTTYIFSPVF RNSPSTIDKD  240
IGYLSLQTVI EYMCNEAWSR W                                            261

SEQ ID NO: 170          moltype = AA  length = 261
FEATURE                 Location/Qualifiers
REGION                  1..261
                        note = Synthetic
source                  1..261
                        mol_type = protein
                        organism = synthetic construct
SEQUENCE: 170
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VAANALSYMS PKPSLYYTSG KTTYIFSPVF RNSPSTIDKD  240
IGYLSLQTVI EYMCNEAWSR W                                            261

SEQ ID NO: 171          moltype = AA  length = 261
FEATURE                 Location/Qualifiers
REGION                  1..261
                        note = Synthetic
source                  1..261
                        mol_type = protein
                        organism = synthetic construct
SEQUENCE: 171
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNAAALSYMS PKPSLYYTSG KTTYIFSPVF RNSPSTIDKD  240
IGYLSLQTVI EYMCNEAWSR W                                            261

SEQ ID NO: 172          moltype = AA  length = 261
FEATURE                 Location/Qualifiers
REGION                  1..261
                        note = Synthetic
source                  1..261
                        mol_type = protein
                        organism = synthetic construct
SEQUENCE: 172
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
TSIEYSLTKK KGFSRQFTAS TEVKVGVSAG IFGCETSLEV TTGFSYSETI NEETTETWKK  180
TLTGPQDYWT FQPVLLYAWK VNANALAYMS PKPSLYYTSG KTTYIFSPVF RNSPSTIDKD  240
IGYLSLQTVI EYMCNEAWSR W                                            261

SEQ ID NO: 173          moltype = AA  length = 261
FEATURE                 Location/Qualifiers
REGION                  1..261
                        note = Synthetic
source                  1..261
                        mol_type = protein
                        organism = synthetic construct
SEQUENCE: 173
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTVPSG  120
```

-continued

```
TSIEYSLTKK KGFSRQFTAS TEVKVGVSAG IFGCETSLEV TTGFSYSETI NEETTETWKK  180
TLTGPQDYWT FQPVLLYAWK VNANALSYMS PKPSLYYTSG ATTYIFSPVF RNSPSTIDKD  240
IGYLSLQTVI EYMCNEAWSR W                                            261

SEQ ID NO: 174          moltype = AA  length = 261
FEATURE                 Location/Qualifiers
REGION                  1..261
                        note = Synthetic
source                  1..261
                        mol_type = protein
                        organism = synthetic construct
SEQUENCE: 174
MNNESQAKDS SLRMEPLEKE KGAAGQGALS QIPPESYRTK SPAELLGAGK TRADLNFPDV   60
KNDYELDNAL IGQTVTSNGC VVKAPWVRKD FNTPGYWSEG YIKPCAAYLS YIKKDTIPDG  120
TSISHTFEKK KGYSSEFSVS TEVKASVGVN ILGCDASMEV TTGFTYTQGI SSETTESWTD  180
TVTGPQDYWT FQPVLLYAWK VNANALSYMS PKPSLYYTSG KTTYIFSPVF KDSPETLDED  240
IQYVNEQDFN EYLLNAGWGR W                                            261

SEQ ID NO: 175          moltype = AA  length = 270
FEATURE                 Location/Qualifiers
REGION                  1..270
                        note = Synthetic
source                  1..270
                        mol_type = protein
                        organism = synthetic construct
SEQUENCE: 175
MNNESQAKDS SLRMEPLEKE KGAAGQGALS QIPLKRMKDF IAHERSAIVP AGTNRSNLVA   60
ASYPWATGDF GIDNYLKTQN PSQAGCVVKA PWVRKDFNTP GYWSEGYIKP CAAYLSYIKK  120
DTIPNGVDIQ HQVTKKKGFT SSFTTETKSS YSVGAKIDIC NVGSSITTGF SQTQSWSQER  180
DESWTTTLHG PQDYWTFQPV LLYAWKVNAN ALSYMSPKPS LYYTSGKTTY IFSPVFRDDC  240
FTKLYKEDDY SYVSFDEVSN YLTTDGVNRW                                   270

SEQ ID NO: 176          moltype = AA  length = 268
FEATURE                 Location/Qualifiers
REGION                  1..268
                        note = Synthetic
source                  1..268
                        mol_type = protein
                        organism = synthetic construct
SEQUENCE: 176
MNNESQAKDS SLRMEPLEKE KGAAGQGALS QIPTNTTVNA QITDAVDGAS SSITDLKWNI   60
PKSSTVKTNF QIDNHLKLQT NPDSMGCVVK APWVRKDFNT PGYWSEGYIK PCAAYLSYIK  120
KDTVVGTQIY EFSKKKGYSS TFSVSTSVKA SVGGSIGACE TSFEVTTEFG YSSTSYSETT  180
TTWTETLTAQ DYWTFQPVLL YAWKVNANAL SYMSPKPSLY YTSGKTTYIF SPVFRNSPFT  240
IEFSNDDYDY IDEDDLIDYL MKDGYSKW                                     268

SEQ ID NO: 177          moltype = AA  length = 262
FEATURE                 Location/Qualifiers
REGION                  1..262
                        note = Synthetic
source                  1..262
                        mol_type = protein
                        organism = synthetic construct
SEQUENCE: 177
MNNESQAKDS SLRMEPLEKE KGAAGQGALS QIPPETYPVK SVEELLGQGK TRADLVFPDV   60
RNDYELDNAL IGQTVNNNGG CVVKAPWVRK DFNTPGYWSE GYIKPCAAYL SYIKKDTVPS  120
GVQIGYTLRK KKGFSRQFTT STEVKSSVTA GILACEATLE VTTSFSYSET IEEEFEETWT  180
KTLTGPQDYW TFQPVLLYAW KVNANALSYM SPKPSLYYTS GKTTYIFSPV FRNSPSTLDR  240
EIGYLSLQTV AEYLQNEAWG RW                                           262

SEQ ID NO: 178          moltype = AA  length = 262
FEATURE                 Location/Qualifiers
REGION                  1..262
                        note = Synthetic
source                  1..262
                        mol_type = protein
                        organism = synthetic construct
SEQUENCE: 178
MNNESQAKDS SLRMEPLEKE KGAAGQGALS QIPAENYPTR SIAELLGPGK TRANLNFPDV   60
RNDYELDNAL VGQTVTTNGG CVVKAPWVRK DFNTPGYWSE GYIKPCAAYL SYIKKDTVPS  120
GVQISYSLSK KKGFTRQFTT STSVTSSVSA GIFGCEASLE VTTGFSYSET INEETTETWT  180
RTLTGPQDYW TFQPVLLYAW KVNANALSYM SPKPSLYYTS GKTTYIFSPV FRNTPSTIDR  240
EIGYLSLNDV VEYLSNEAWG RW                                           262

SEQ ID NO: 179          moltype = AA  length = 270
FEATURE                 Location/Qualifiers
REGION                  1..270
                        note = Synthetic
source                  1..270
```

-continued

```
                              mol_type = protein
                              organism = synthetic construct
SEQUENCE: 179
MNNESQAKDS SLRMEPLEKE KGAAGQGALS QIPADPESAK KIGVPRALVS KAASSSNFDP    60
AKSQTCTSNF QIDNAIKLQT PPDSMGCVVK APWVRKDFNT PGYWSEGYIK PCAAYLSYIK   120
KDTVPGGMEI TLEKKKGYSS RFQTSTEIKA GLSAGIFGCN ASLEVTTGFT YEQTITSETT   180
ETWKETLTGS QDYWTFQPVL LYAWKVNANA LSYMSPKPSL YYTSGKTTYI FSPVFRNDPF   240
TLKYSDADYD YVPYDDIIEY VTNSGWNRCH                                    270

SEQ ID NO: 180          moltype = AA   length = 269
FEATURE                 Location/Qualifiers
REGION                  1..269
                        note = Synthetic
source                  1..269
                        mol_type = protein
                        organism = synthetic construct
SEQUENCE: 180
MNNESQAKDS SLRMEPLEKE KGAAGQGALS QIPVERIPEQ LESVVAHAIA KSQPRAKFDL    60
NRCAIVESNF QLDNALSLQN PPDAAGCVVK APWVRKDFNT PGYWSEGYIK PCAAYLSYIK   120
KDTLAGTEIH TLRKKKGYTS RFTASTEVKA SASAGIFGCE ASLEVTTGFS YGEEITEEKE   180
ETWKTTVAGP QDYWTFQPVL LYAWKVNANA LSYMSPKPSL YYTSGKTTYI FSPVFRNSPF   240
TIPYNDGDVD YVGYDTLIDH LVNSGFSKW                                     269

SEQ ID NO: 181          moltype = AA   length = 270
FEATURE                 Location/Qualifiers
REGION                  1..270
                        note = Synthetic
source                  1..270
                        mol_type = protein
                        organism = synthetic construct
SEQUENCE: 181
MNNESQAKDS SLRMEPLEKE KGAAGQGALS QIPVERIPEQ LESVVAHAIA KSQPRAKFDL    60
NRCAIVESNF QLDNALSLQN PPDAAGCVVK APWVRKDFNT PGYWSEGYIK PCAAYLSYIK   120
KDTLAGTEIH TLRKKKGYTS RFTASTEVKA SASAGIFGCE ASLEVTTGFS YGEEITEEKE   180
ETWKTTVAGP QDYWTFQPVL LYAWKVNANA LSYMSPKPSL YYTSGKTTYI FSPVFRNSPF   240
TVKFENDDYD YVPYDRLVDY LVSDEGFAKW                                    270

SEQ ID NO: 182          moltype = AA   length = 269
FEATURE                 Location/Qualifiers
REGION                  1..269
                        note = Synthetic
source                  1..269
                        mol_type = protein
                        organism = synthetic construct
SEQUENCE: 182
MNNESQAKDS SLRMEPLEKE KGAAGQGALS QIPEHIPKQL ESAVAHAPAN KAQPRGKFDL    60
NRCAIVESNF QLDNAISLQN PPDAAGCVVK APWVRKDFNT PGYWSEGYIK PCAAYLSYIK   120
KDTLSGTEIH TLRKKKGYTS RFTASTEVKA SASAGIFGCE TSLEVTTGFS YGQEITDEKE   180
ETWKTTVAGP QDYWTFQPVL LYAWKVNANA LSYMSPKPSL YYTSGKTTYI FSPVFRNSPF   240
TIPYNDDLVD YVGYDTLVEH LMENGFSKW                                     269

SEQ ID NO: 183          moltype = AA   length = 269
FEATURE                 Location/Qualifiers
REGION                  1..269
                        note = Synthetic
source                  1..269
                        mol_type = protein
                        organism = synthetic construct
SEQUENCE: 183
MNNESQAKDS SLRMEPLEKE KGAAGQGALS QIPMSIDVQH AESEAAQQVA KTKPHIKFDL    60
SRASVVTSNF QLDNAISLQH PPDAAGCVVK APWVRKDFNT PGYWSEGYIK PCAAYLSYIK   120
KDTLSGTSIH TLRKKKGYTS RFNVSTELKA GIKAGIFGCE ASLEVTTGFS YGEDISQETE   180
ETWKTTVAGP QDYWTFQPVL LYAWKVNANA LSYMSPKPSL YYTSGKTTYI FSPVFRNSPF   240
TIPYSDNDVD YIAFDTLTDY LMGDGFSKW                                     269

SEQ ID NO: 184          moltype = AA   length = 270
FEATURE                 Location/Qualifiers
REGION                  1..270
                        note = Synthetic
source                  1..270
                        mol_type = protein
                        organism = synthetic construct
SEQUENCE: 184
MNNESQAKDS SLRMEPLEKE KGAAGQGALS QIPRNVSDFL RHQKSAVAAP NIVTGQSNSA    60
SYPWAVGGDF GIDNCLKNQD PPPGGCVVKA PWVRKDFNTP GYWSEGYIKP CAAYLSYIKK   120
DTVPSGATIH YTTTKKKGFT ETFTKETKAS YSVGANIDIC NVGSSITTGF SRSSSWSQQT   180
IQSWTTTLQG PQDYWTFQPV LLYAWKVNAN ALSYMSPKPS LYYTSGKTTY IFSPVFRSDS   240
FTSRYDSSDY SYISFNDAVN YLMKDGAKRW                                    270
```

```
SEQ ID NO: 185          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 185
atgaataacg agtctcaggc taaagactct tcactgcgca tggaaccact ggaaaaagag   60
aaaggagccg ccggccaggg tgccttatcc cagatccccc cggaatccta tcgcaccaaa  120
tcgccggctg aattacttgg cgcgggaaaa acacgtgccg acctcaactt cccagatgtt  180
aagaacgact atgagttgga taatgcactg ataggtcaga cggtcacgtc aaacggatgt  240
gtcgtcaaag cgccatgggt gcgcaaagat tttaatactc ctggctactg gagcgaaggt  300
tacataaaac cctgcgcagc ttatctcagc tatataaaaa aggacacagt gccatctggc  360
acatcaatag aatattcatt gacgaaaaaa aaaggttttt cacgccaatt tacagcctcg  420
acagaggtca aggtaggtgt atcggcggga atttttggtt gtgagacgtc attggaggtg  480
acaacggggt tctcctattc tgaaacgatt aacgaagaaa ctaccgagac ctggaaaaaa  540
acgttgaccg gtccccagga ttactggacg tttcaaccag tcttattata cgcctggaaa  600
gtaaatgcta acgccctctc ctacatgtca ccgaaaccgt cactgtatta cacgagcggc  660
aagaccacat acatattcag tccggttttt cgcaactctc catccaccat tgataaagac  720
attgggtatc tgtccttgca gactgttatc gaatatatgt gtaacgaggc gtggagtaga  780
tggtaa                                                            786

SEQ ID NO: 186          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 186
atgaacaacg agagtcaagc taaggattcc agtttacgga tggaaccact cgaaaaagaa   60
aaaggcgccg cgggtcaggg cgcgctctct cagatcccgc cagaatcata ccgaactaag  120
agcccggcgg agctcctggg tgctggcaag actcgtgctg atctgaattt ccccgatgtg  180
aaaaatgatt atgaactcga taatgctctg attggtcaga cggtgaccag caacggctgt  240
gtagtcaaag cgccgtgggt tcggaaagat tttaacaccc ccggttattg gagtgaaggg  300
tatatcaaac cttgtgcagc ctatctgagc tatattaaaa aggataccgt tccttctgga  360
acatcaatcg aacatacatt aaccaaaaaa aaaggattca ccagccgctt taccgcaagc  420
actgaagtta aagttggtgt gtcagccggg attttggtt gcgaaacatc cttggaagta  480
acgacaggtt tctcttattc tgaaaccata aatgaagaaa ctactgaaac ctggaagaag  540
acagtggcgg ggccacaaga ctactggacg tttcaaccag tactgctcta cgcttggaaa  600
gtgaacgcaa atgcgctgag ttatatgtcg cctaaaccat ctctctatta taccagcggc  660
aaaaccacgt acatattctc cccggtgttt cggaacagcc aagcacaat tgataaagat  720
attggttacc tgtcacttca gacagtaatc gaatacatgt gcaatgaagc atggagtcgc  780
tggtaa                                                            786

SEQ ID NO: 187          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 187
atgaataatg aaagccaggc caaagattca tcgctgcgca tggaaccact ggaaaaagaa   60
aaaggcgcgg ctgggcaggg tgcgctgagc cagattccgc ccgaaagtta cagaaccaaa  120
tccccggctg agctgctggg tgcaggtaaa acgagagcgg atttaaactt tccagacgtg  180
aaaaatgatt atgagctgga caacgcgctt attggtcaga ccgtgacgtc caatggctgc  240
gtcgtcaaag cccccttgggt tcgtaaagac tttaatacce caggatattg gagtgagggc  300
tatattaaac catgtgcagc atatctctct tatattaaaa aggataccgt cccagtgga  360
actagtattg aacatacgct tacgaagaaa aaagggttta cgtcgcgatt tactgccagc  420
gccgaagtta aagttggtgt tagtgcagga attttcggct gcgaggcgag tcttgaggtc  480
acaacgggct tcagctacgg ccaagatatc aatgaagaaa ctacggaaac ctggaaaaaa  540
acggtagcag gccccagga ttactggacg tttcagccag tgcttctgta cgcgtggaaa  600
gtaaatgcta acgccttatc atacatgtcg ccgaaaccca gtctttatta tacatcgggc  660
aaaactactt atatattttc tccagttttt cgtaactccc caagtacaat cgacaaagac  720
atcggctacc tgtccttgca gacagtgatt gaatatatgt gtaacgaggc atggtcacgg  780
tggtga                                                            786

SEQ ID NO: 188          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 188
atgaacaacg aatcgcaggc caaagacagt tcattgcgca tggagccatt agaaaaggag   60
aagggggcag caggtcaggg cgcacttagt cagataccac ccgaatctta ccgcacgaaa  120
```

```
tctcccgcag aactgctcgg tgcgggtaag acgcgtgcgg atctcaattt tcctgacgtg   180
aagaatgact atgaactgga taatgcctta ataggccaga ccgttacctc taatggttgt   240
gttgtgaaag cgccatgggt tcgtaaggac ttcaatacgc caggatattg gtccgaggga   300
tatatcaaac cgtgtgccgc ttatctttcc tatatcaaaa aagatacagt cccaagtggt   360
acttcgatcg aacatacact gacaaagaaa aaaggtttta caagccgatt cactgcgtca   420
accgaagtga aagttggtgc ttcagcaggg gtattcgcct gtgaaacaag cctggaagtg   480
accacagggt tctcctacgg ccaagacatt aacgaagaga ccacagagac atggaaaaaa   540
acagttgccg ggccacagga ttattggaca tttcagcctg ttctcctta cgcgtggaag    600
gtcaatgcga atgcactttc ttatatgtca cctaaaccat cactgtatta tacttcgggc   660
aagacaactt acatcttttc accggtattt cgcaactcac cctctactat cgataaagac   720
atcggatatt tatctttaca aactgttatc gaatacatgt gcaacgaagc ttggagccgg   780
tggtaa                                                              786
```

SEQ ID NO: 189          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 189
```
atgaacaatg agtcgcaagc taaagattcg tcactgagaa tggaacccctt ggaaaaagag   60
aaaggagcag ccggccaggg cgcgctgtca cagatacctc ctgagtcgta tcggacaaaa   120
tcccctgcag aacttctggg cgcaggaaag acccgtgcag acctcaattt ccctgacgta   180
aaaaacgatt atgaattaga taatgcgctg ataggtcaga ccgttacttc taacgggtgc   240
gtggttaaag ccccttgggt ccggaaggat tttaatacgc cggggtattg gtctgagggg   300
tacataaaac catgtgccgc atatttgtca tatataaaaa aagatacagt tccgtcaggt   360
actagtatcg aacatacatt aaccaaaaag aaaggtttca ccagtcgttt caccgcatct   420
gcagaggtga aagtcggcgc gagtgctggt gtgtttgcgt gcgaggcctc cctggaggtg   480
acaaccggtt ttagttacgg ccaggatatt aatgaggaga caactgaaac gtggaaaaaa   540
accgttgccg gcccgcagga ctattggacg ttccaacctg ttctcctgta tgcttggaaa   600
gttaacgcta atgcactttc gtatatgagc ccaaagcctt ctctttacta tacctctgga   660
aaaacgacat atattttttc tcctgtctttt cgtaattcac catcgacgat cgataaagat   720
ataggtatc tgagcctcca gaccgtgata gagtacatgt gcaatgaggc ttggtctcgc    780
tggtaa                                                              786
```

SEQ ID NO: 190          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 190
```
atgaataatg aatcccaggc gaaagattca tcgctgcgca tggaaccgct tgaaaaagag   60
aaaggagccg ctggtcaggg tgcgttgtct caaatccccc ccgagtcgta tcgaactaag   120
tctccggcag aactttttagg tgcgggcaaa acacgcgcg acctcaattt cccagatgtt   180
aagaatgatt atgagcttga taatgctctg ataggtcaga ccgtcacttc aaatgggtgc   240
gttgtgaaag caccgtgggt tcgcaaagat tttaatacgc ctggttactg gagcgagggc   300
tatatcaaac cttgcgcggc ttatctctct tatataaaga aagatacaat cccaagcggt   360
acttcaattg agcatacact gacgaaaaaa aaaggtttta cttcccgttt taccgtctcg   420
gcagaagtca aagctggagc tagtgccggt gtgtttgcat gtgaagcgag tttagaggtt   480
acaaccggtt tctcgtatgg acaggatatt aatgaggaga ccactgagac ctggaagaaa   540
accgtagcgg gaccgcaaga ctattggacg ttccagcccg ttctgctgta tgcctggaag   600
gtcaatgcca atgcgctgtc ctatatgagc ccgaaaccaa gtttatatta tacgagtggc   660
aaaaccacct acattttcag tccggttttt cgaaactcgc cttctacaat agataaggac   720
attggatatc tgtcattaca gaccgtgatt gagtatatgt gtaatgaagc ttggtctcgt   780
tggtga                                                              786
```

SEQ ID NO: 191          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 191
```
atgaataatg agtcccaagc caaggactca agtcttcgta tggaacccct ggaaaaagag   60
aagggcgccg cgggacaggg tgcgttaagc cagattcccc cggagtcgta ccgtaccaaa   120
tcgcctgctg aactcctcgg agcagggaaa acccgggcag atctcaattt cccggatgtt   180
aaaaacgatt acgaattgga taatgcactg attggtcaga ctgtaacaag taatggttgc   240
gtcgtcaaag ctccgtgggt ccggaaagat ttcaataccc ccggttactg gagtgaaggt   300
tatattaaac catgtgcagc gtatctgtct tacattaaaa aagataccat tccgtctgga   360
accgccgagg aacatacttt gacgaagaaa aagggtttca ctagtcgctt cacagtaagt   420
gcagaagtta aagcaggcgc cagtgccggc gtctttgcct gtgaagcatc acttgaagtt   480
actaccggct tctcgtatgg ccaagacatt aatgaagaaa ctgaagaaac atggaagaaa   540
actgtcgcgg gcccgcagga ttattggacc tttcaaccgg tattgctcta tgcatggaaa   600
gtgaacgcaa atgcttatc gtacatgtcg ccgaaaccga tctctacta tacaagtggg    660
aaaactactt atatctttttc gcctgtgttt cgcaactccc gtctaccat tgataaagac    720
```

```
attggttatt tgagtctcca gaccgttatc gaatatatgt gtaatgaagc atggtcacgc   780
tggtga                                                              786

SEQ ID NO: 192           moltype = DNA  length = 786
FEATURE                  Location/Qualifiers
misc_feature             1..786
                         note = Synthetic
source                   1..786
                         mol_type = other DNA
                         organism = synthetic construct
SEQUENCE: 192
atgaacaatg aatcgcaggc caaagatagt agtctgcgta tggaacctct ggagaaagag   60
aaaggagccg ccggacaagg cgcactgtcg cagattccac ctgaatctta tcggaccaaa   120
tcgcctgccg aattgctggg ggctggaaag acgcgtgcag atctcaattt tccggacgtt   180
aaaaatgatt acgagctgga caacgcgctt attggccaga cagtgacaag taacggatgt   240
gtggtaaaag ccccgtgggt acgtaaagat tttaatactc cgggctactg gtccgagggc   300
tatattaagc cgtgcgcggc atatctgtcc tacatcaaga aagacacgat accatccggg   360
actagtgaag aacacacatt aaccaagaag aaaggcttct ctcgccagtt cactgtcagt   420
gcagaagtta aagcgggtgc cagtgcagga gtattcgcat gcgagactag tctggaggta   480
acgacaggtt tcagttacgg acaggatatt aatgaagaaa ccgaagaaac ctggaagaaa   540
accgtaacag gaccacagga ctattggaca ttccagcccg ttttgttata tgcttggaaa   600
gttaatgcaa atgcactgag ttacatgagt cctaaaccta gtttgtacta taccagcggg   660
aagacgacct atattttctc acctgtgttt cgcaactctc cttccacaat agacaaagat   720
atcggatatc tgtcactgca gacggttatc gagtatatgt gtaatgaagc gtggagtcga   780
tggtaa                                                              786

SEQ ID NO: 193           moltype = DNA  length = 786
FEATURE                  Location/Qualifiers
misc_feature             1..786
                         note = Synthetic
source                   1..786
                         mol_type = other DNA
                         organism = synthetic construct
SEQUENCE: 193
atgaacaacg aaagtcaagc caaggattcg tctctgcgca tggaaccctt agaaaaagaa   60
aaggggcag caggccaggg agccctgtcg cagattcccc cagagtctta ccgtactaaa   120
agtcctgcgg aattattagg agccggcaag acacgtgcag atctgaattt cccagatgtc   180
aaaaatgact atgagctgga taatgcgctc attggacaga ccgttacatc aaacggttgc   240
gtcgtaaaag ctccgtgggt tcgcaaagat tttaatacac gggggtattg gtcagaggga   300
tacattaaac catgtgccgc ctacttatcc tacattaaga aggatacaat cccatctggg   360
acgtccgaag aacatactct gacgaaaaaa aaaggcttta gccgtcaatt taccgtgtcg   420
gcagaggtga aagcaggcgc ttctgctggt gttttttgcct gtgaaacatc gcttgaagtt   480
acgactggat tttcttacgg ccaggatatt aacgaggaaa cgaagaaac cgatacaaca   540
acagtgacag gtcctcaaga ctactggact ttccaacccg tgctcttgta tgcgtggaaa   600
gttaacgcca atgcgctgag ctatatgtcg ccgaaaccct cactgtatta tacctccggg   660
aaaactacct acatattctc cccagtgttt cgtaatagcc catcaacaat tgataaggat   720
ataggatact tgtctctgca gacagttatt gaatacatgt gcaacgaagc atggagtcgc   780
tggtga                                                              786

SEQ ID NO: 194           moltype = DNA  length = 786
FEATURE                  Location/Qualifiers
misc_feature             1..786
                         note = Synthetic
source                   1..786
                         mol_type = other DNA
                         organism = synthetic construct
SEQUENCE: 194
atgaataatg aaagccaagc caaggattcg tcattacgta tggaaccctt ggaaaaggaa   60
aaggggcgg caggtcaggg cgccctgtct cagatccctc cggagagcta tcgtacgaaa   120
agtcccgccg agctgctggg ggctggtaag acacgagcgg atttgaattt tccggatgta   180
aaaaacgatt acgcactgga caactatctg ataggacaaa ccgtaacgag caatggttgt   240
gtcgtaaagg ccccttgggt ccgtaaagat ttcaatacac ctggttattg gtctgaaggt   300
tacattaagc cgtgtgcagc gtatttaagc tatattaaaa aggacacaat acctagcggc   360
acaacgcgag aacacactct gacgaaaaaa aaagggttct ctagacagtt tacggttagt   420
gcggaagtta aagccggagc ctctgcgggt gtatttgctt gcgagacgac tctggaggtg   480
accactggat tttcctacgg tcaggatatt aatgaagaaa cagaagagac cgatacgacc   540
accgtcacgg gccctcagga ttactggacc tttcagccgg ttctgctgta cgcgtggaaa   600
gtgaatgcta atgcattatc ttatatgagc cccaagccct cctttatta tacttctggc   660
aaaacaacct atatattttc tccggtgttc cgtaacagcc cctccacaat cgataaggac   720
attggttacc tctcattgca gaccgttatt gaatacatgt gtaacgaagc atggtctcgc   780
tggtaa                                                              786

SEQ ID NO: 195           moltype = DNA  length = 786
FEATURE                  Location/Qualifiers
misc_feature             1..786
                         note = Synthetic
source                   1..786
                         mol_type = other DNA
                         organism = synthetic construct
```

-continued

```
SEQUENCE: 195
atgaataatg aatcccaggc gaaagacagc agtctgcgaa tggaaccact cgagaaagag   60
aaaggtgcag ctggtcaggg agctctgtcg cagattcctc cagaatcata tcgtacaaag  120
tccccagcag agcttctcgg tgctggcaaa acgagagcag atttaaactt cccggacaca  180
aaaaatgact atgctttgga caattatctg ataggacaaa ccgtaacatc taacggctgt  240
gttgtcaaag cgccgtgggg gcggaaagac tttaatactc ccgggtattg gagtgaaggt  300
tatattaagc catgcgcagc gtacctttcg tatatcaaga aagacacgat accatcgggt  360
acctctgaag aacataccct gactaaaaaa aaaggctttt ctcgtcaatt cacggtgtct  420
gcagaagtga aagcaggcgc ctcggctggg gtatttgctt gtgagaccag tcttgaagtg  480
accacaggct tcagttatgg tcaggatatt aatgaggaaa ccgaagagac ggacacaacg  540
acagttactg gaccccagga ttattggaca ttccagcctg tcctgctgta cgcgtggaaa  600
gtgaacgcca atgctctgtc ttacatgagt ccgaaaccga gcttgtatta cacctcaggt  660
aaaaccacgt atatcttctc tccagtattt agaaattctc cctcgactat tgacaaagac  720
attgggtatc ttagcctcca gacagtgatt gagtatatgt gcaatgaagc atggtcgcgt  780
tggtaa                                                                786

SEQ ID NO: 196          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 196
atgaacaatg aatcccaagc gaaagattca tcacttcgca tggaacctct ggagaaagag   60
aaaggcgccg cggggcaagg ggcgttgagc cagattccgc cggaatctta tcgtacaaaa  120
agtcctgcag aactgttggg cgcagggaaa acacgcgctg accttaactt tcccgacgtt  180
aaaaacgatt atgagctgga taacgctctg attgggcaga cggttacatc taacggttgt  240
gtcgtgaaag ccccgtgggt cagaaaagat tttaatacgc caggctattg gtcagaagga  300
tatatcaaac cgtgcgcggc ctacctgtca tacattaaaa aagatactat tccttctggc  360
acttcaatcg aatattctct gacaaaaaaa aaaggcttca gccgtcagtt caccgtttca  420
gcggaggtaa aagttggtgt ctcagccggc atatttgggt gcgagacgag ccttgaagtt  480
acaacagggt tttcgtatag cgaagatatt aacgaagaga ccacggaaac atggaaaaaa  540
acgcttaccg gacctcaaga ctactggacc tttcaacctg ttctgctgta tgcctggaag  600
gtgaacgcca acgctttaag ttacatgtca ccgaaaccgt cactgtacta tacaagcggt  660
aaaactacct atatttttag tccagtgttt cgtaattccc catctaccat cgacaaagac  720
attggttatt tatcgttaca aactgtgata gaatacatgt gcaacgaagc atggagccgt  780
tggtaa                                                                786

SEQ ID NO: 197          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 197
atgaataatg aaagtcaagc caaagacagc agtttgcgta tggaaccgtt agaaaaagag   60
aaaggtgctg caggtcaggg tgccttaagc cagatccctc cagaaagcta tcgcactaaa  120
tcaccggcag agcttctggg cgcaggtaag acccgagctg atttgaattt tccagatact  180
aaaaatgact acgctttaga taatgcatac atcggtcaga ccgtgacttc taatggctgt  240
gttgtgaagg ccccctgggg acgcaaagat tttaatacgc ccgggtactg gtcagaaggt  300
tatattaaac cgtgtgcggc gtatttgtca tacatcaaaa aagacacaat accgtctggc  360
acgagtatcg agtatagtct gacaaaaaaa aaaggcttta gtcgtcagtt cactgttagc  420
gcagaggtca aagtaggcgt gtcagctggg attttggat gcgagacatc actggaagta  480
acgacggggt ttagttatag cgaagatatt aatgaagaaa caactgaaac ttggaaaaaa  540
acgttaaccg gcccgcaaga ttattggaca ttccagccag tgctgttata cgcatggaaa  600
gtaaacgcaa acgccctgtc ctatatgtcc ccaaaaccca gcttatatta caccagtgga  660
aaaaccacct atattttcag tcccgtcttt cggaatagcc ctagcactat agataaagat  720
attggttatc tgtctttgca aactgtgatc gagtacatgt gcaatgaagc gtggagtcgc  780
tggtaa                                                                786

SEQ ID NO: 198          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 198
atgaataacg aaagccaggc aaaagactca tctttacgca tggaacccct ggaaaaagaa   60
aaaggtgcgg caggtcaggg agctttgtca cagattccac ccgaatcgta ccgtacgaag  120
tcgcctgcgg agtacttggt ggccgggaaa acccgtgcag atctgaactt tccagacaca  180
aaaaatgact atgcgcttga taacgcatat attggtcaaa ccgtgactag taatggctga  240
gtagtgaaag ctccctgggg gcgaaaagac tttaatactc ctggatactg gagcgaaggt  300
tacattaaac cgtgtgcggc ttatttatca tatatcaaaa aagacacaat cccgtccgga  360
accagtatcg aatactcact taccaaaaaa aaaggttttt cacgtcagtt taccgtctca  420
gcagaggtta aggttggggt aagtgcaggg attttcggct gtgaaccag tctggaagtt  480
acaacgggct ctcatattc cgaggacatc aatgaagaga ctaccgagac tgacacaaca  540
```

-continued

```
acgctggcag gccctcagga ctactggacc ttccaacccg ttttactgta cgcctggaaa    600
gttaatgcta acgcactcag ttacatgtca cccaaaccca gcctgtatta cacctccggt    660
aagactacat atattttcag ccctgttttt cggaattcgc cgtcaactat tgataaggac    720
attggctatc tgtccttaca aacggtaatc gaatatatgt gcaacgaagc atggtcacgg    780
tggtaa                                                                786

SEQ ID NO: 199          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 199
atgaataatg aatctcaggc caaagatagc tctctgcgga tggaacctt agaaaaagaa      60
aaaggtgccg ccggtcaggg cgcactgtca caaattccgc ccgagagcta ccgtaccaaa    120
agcccagctg agttattagg ggctggtaaa acccgagccg acttaaactt ccccgataca    180
aagaatgatt acgcactgga taatgcgtac atcggacaga ccgtcacaag taatggatgc    240
gtagttaaag ctccgtgggt acggaaggac tttaacactc ccggctactg gagcgaaggg    300
tacatcaagc catgtgccgc ttacctgagc tatattaaaa aagatactat cccgagtggc    360
acatctattg agtatagtct cacaaaaaag aaaggatttt cacgtcagtt taccgtctcc    420
gctgaagtca aagttggaat tagtgcaggt gtctttggtt gcgaaacatc actggaagtt    480
accacgggat tctcctactc agaggatatc aatgaagaga caacagagac cgacacaacg    540
acgctggccg tccacagga ctactggact ttccagcctg tattattgta tgcctggaaa     600
gttaatgcta acgcgctgag ttatatgtca cccaaaccct cgctttacta caccagcggg    660
aaaacgacct atattttag tccggtgttc cgcaattccc caagcaccat tgacaaagat      720
attgggtacc tttcacttca gaccgtaatt gaatacatgt gcaatgaagc ttggtcacgt    780
tggtag                                                                786

SEQ ID NO: 200          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 200
atgaacaacg agagccaggc gaaagattca tctctgcgca tggagccgct tgaaaaagag      60
aaaggtgcag ctggtcaggg cgctcttagc cagataccac ctgagtcata tcgcacgaaa    120
agcccggcag aattacttgg tgccggaaag acccgggcag acctgaactt tcccgatacg    180
aaaaatgact acgcactcga taacgcttac atcgggcaga ctgttacgag taatggttgt    240
gttgtaaaag cgccatgggt gcgtaaagac ttcaataccc cgggttactg gtcagagacc    300
tatattaaac cttgcgcagc gtatttatcc tatattaaga aggataccat accttcaggt    360
acttcaatag aatattcttt aaccaaaaag aagggatttt ctcggcagtt tacagttagt    420
gcggaggtga aggtaggtat ttcggccggc gtgtttgggt gcgagactag tctggaagtt    480
acaaccgggt tttcatactc tgaagatatt aacgaagaaa caactgagac ggataccacc    540
acgttggcgg gaccgcagga ctattggacc tttcaaccgg tactttttgta tgcctggaag    600
gtgaacgcca atgcactttc ttatatgtcg ccgaaaccga gtctttatta taccagcgga    660
aaaacaactt atatttttc gccagtgttc cgcaacagtc cgagtaccat tgacaaggac    720
attgggtatt taagtctgca gcgtaatgta ctgtacatgt gcaatgaagc ctggtctcgt    780
tggtaa                                                                786

SEQ ID NO: 201          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 201
atgaataatg agagtcaagc aaaagattca tctctgcgta tggagccgct tgaaaaagaa      60
aaaggcgccg cagggcaagg cgcactgtcc cagattcctc ctgaaagcta tcggaccaaa    120
tctcccgccg aattattggg ggccggcaaa acacgcgcag atttgaattt tccagatgtc    180
aagaatgact acgaactgga caatgcatta attggacaga ccgttaccag taacgggtgt    240
gtggtaaagg caccgtgggt tcgcaaagat ttcaataccc caggttactg gagcgaaggt    300
tacattaagc catgcgcggc gtatctgagc tatataaaaa aagataccgt tccaagtgga    360
acgtcgatag aacatacttt aaccaaaaaa aaagggtttt cacgccaatt taccgcctct    420
accgaagtta aggtcggcgt ttcggcgggt attttcggct gtgaaacatc attagaagtc    480
accacaggct tctcttacag cgaaactatt aatgaagaaa caaccgaaac gtggaaaaag    540
acactcacag gtccgcagga ctattggacg tttcaaccag tgttactgta cgcgtggaaa    600
gttaacgcaa atgccctgtc ttatatgtcc cctaagccga gcttatatta tacgagcggc    660
aagaccacat atatttttctc tcccgtattt cgtaacagcc cgtctaccat cgataaagac    720
attggatact tgtcgttaca gactgtgatc gagtacatgt gtaatgaggc ttggagccgg    780
tggtaa                                                                786

SEQ ID NO: 202          moltype = DNA   length = 786
FEATURE                 Location/Qualifiers
misc_feature            1..786
                        note = Synthetic
```

-continued

```
source                   1..786
                         mol_type = other DNA
                         organism = synthetic construct
SEQUENCE: 202
atgaacaacg aatcgcaggc caaagattca agcctccgta tggagccgct ggaaaaagag    60
aaaggtgcgg caggtcaggg ggccttatcc caaattcctc cggaaagtta tcgcacgaaa   120
agcccggcgg agcttcttgg ggctggtaaa acgcgtgccg acctgaactt tccggacgta   180
aaaaacgact atgagctgga caatgccctg atcggtcaga ccgttactag caacggttgc   240
gttgttaaag caccgtgggt tcgtaaggat ttcaacactc caggttactg gtctgaagga   300
tacattaagc cgtgtgcggc atatctgtct tatattaaaa aagacactgt accttcagct   360
acctccattg aatactcgct caccaaaaaa aaaggcttta cgtctcgatt cacggcgagc   420
acggaagtta aagtaggtgt ttccgccggc atcttcggat gtgaaacaag tctgaaggtc   480
acgacgggat ttagctacag tgagacaatc aacgaagaga cgacagagac gtggaagaaa   540
accctcacgg gtccgcaaga ttattggacc ttccaacccg tattattata tgcgtggaaa   600
gtaaatgcga acgcccttc ctatatgtcc cccaaaccgt ctctctatta tactagcggc    660
aaaacaacct acattttcag cccagtattc cgaaattccc caagcacaat agataaagat   720
attgggtact tatctcttca gaccgtcatt gagtatatgt gtaacgaagc gtggagtcgc   780
tggtaa                                                              786

SEQ ID NO: 203          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 203
atgaataacg aaagccaggc gaaggactct agcctgcgca tggaaccccct ggaaaaggag   60
aaaggagctg cggggcaggg agccttatct caaattccac ctgaatcata ccgcaccaag   120
tcacctgcag agctgctggg tgcaggcaaa acccgtgcag atttaaactt tccggacgtt   180
aagaatgatt atgaactgga caatgctttg ataggacaga ccgtcacttc aaatggatgc   240
gtagttaaag ccccgtgggt gcggaaagac ttcaatactc ccggatattg gagtgaaggt   300
tacattaagc cctgcgccgc atatctgtca tacattaaaa aagataccgt tccatccggc   360
acctccatcg aatattccct cacaaagaag aagggggttct cgcgtcagtt cacggcaagt   420
accgaagtta aggtaggagt cagtgctgga atttttgggt gcgagaccag ccttgaggtg   480
actacaggct tttcctacgg acaagatatt aacgaggaga cgacagaaac atggaaaaag   540
acgcttaccg gacctcaaga ttactggacc tttcagccgg ttctgttgta cgcatggaaa   600
gttaatgcca atgctttatc gtacatgagc ccgaaaccct ctctgtatta tacttcagga   660
aaaacgacat atattttttc gcctgttttt cgcaattccc cgtcaaccat tgacaaagat   720
atagggtatt taagcctcca gactgtaata gagtatatgt gtaatgaggc ttggagccgt   780
tggtaa                                                             786

SEQ ID NO: 204          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 204
atgaacaacg aatctcaagc aaaagactcc tctttgcgaa tggagccact tgagaaagaa    60
aaggggggctg ctgggcaggg cgccctctct cagatacctc cggaatctta ccggaccaag   120
agccccgcgg aattgctggg tgcaggcaaa acgcgtgccg atttgaattt tccggacgtt   180
aagaacgatt acgaattaga taatgcgctc attgggcaga ctgtcactag caatgggtgt   240
gttgtgaaag caccgtgggt gcgcaaagat tttaataccc cgggctattg gagtgaaggg   300
tatatcaagc cttgcgctgc ttatctgagc tacataaaga aagatacagt ccccttccgg   360
acgagcatcg aatattcttt gacaaagaaa aaagggtttt ctcggcagtt tacggcctct   420
acggaagtga aggtaggtgt cagcgccgga atttttggct gcgaaactag tctggaagtc   480
accactggct tttcttattc agaaactatc aatgaagaga ccacggaaac atggaaaaag   540
actgtgctg gccccaggga ttattggact tttcagcctg tgttattgta tgcatggaaa    600
gttaatgcca atgcacttag ttatatgtcc ccgaagccgt ctttgtatta tacatctgga   660
aagacaacct atatcttttc accagtgttt agaaattcac cctcaacgat cgataaggat   720
atcgggtatc ttagcttgca gaccgttatc gaatatatgt gtaatgaggc gtggtcccgg   780
tggtaa                                                             786

SEQ ID NO: 205          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 205
atgaacaatg agtcgcaggc taaagattct tccttacgta tggagcctct ggagaaagaa    60
aagggtgccg caggccaggg cgctcttagt cagataccac ccgagtccta tcggacaaaa   120
agcccggccg aattgttagg tgctgggaaa acacgagccg acttaaactt cccggacgtc   180
aaaaacgatt atgaactgga taatgcactg atcggccaga cggtaactag caacggttgc   240
gtggtgaaag ccccgtgggt tcggaaagat tttaacacgc ccgggtattg gtctgagggg   300
tatattaaac cgtgtgcggc gtatctgtct tacattaaaa aagacacgat tccgcagaat   360
```

```
gtgacaacca cgttatccta tcaacttacg aaaggccata cccgctcatt tgaaacaagc    420
gtaaatgcca aatattctgt cggtgcgaat atcgacatag tgaacgtggg ttctgaaatc    480
tctactggtt ttacccgaag tgagtcttgg tcgacaacgc agtcattcac ggacactacg    540
gagatgaagg gaccgcagga ttactggaca ttccagccgg tgttattgta tgcgtggaaa    600
gttaatgcca atgccctgtc ttatatgtct cctaaaccga gctatatta tacaagtggt    660
aaaaccactt atatttttc gccggtttt cgcaattctc cgtcaacaat cgataaggat    720
atcgggtatc tcagtctgca aaccgtcata gaatacatgt gcaatgaagc gtggtctcgt    780
tggtaa                                                                786

SEQ ID NO: 206          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 206
atgaacaacg aatcccaagc gaaagattct tccttacgaa tggaaccatt agaaaaagaa    60
aaaggtgccg ccggacaggg cgcgctttct caaatcccgc ctgaatctta tcgtaccaag    120
tcaccagcgg aattattagg agctggaaaa acccgtgcag acctgaattt ccctgatgtt    180
aaaaatgact atgaattgga taatgcactt ataggcaga cagtgacgag caacggttgc    240
gtggtcaagg ccccttgggt aagaaaagac tttaacactc gggatactg gagcgaggga    300
tatataaaac cttgcgcagc ttatttatcc tatataaaa aagatacgat cccgaaccaa    360
gtagacttac agcaccaggt aacgcagaaa tcgggtttga cttccagctt caccaccgag    420
gtaaaaagtt cttactctgt gggcgctaaa atcgacatcg tgaatgttgg ctcttccatt    480
tcaacgggct tcagccagac acagtcttgg tcacaggagc gtgacgaatc ctggactacc    540
accctgcatg ggccacagga ttattggacc tttcaacccg tgctgttgta tgcatggaaa    600
gtaaatgcta atgccctgag ctatatgtct ccgaagccga gcctgtatta tacgtcaggt    660
aaaacgactt atatcttcag tcctgtcttt cgcaatagcc catcaaccat tgataaggac    720
attgggtact taagtcttca gactgtcata gaatatatgt gtaatgaagc ctggtcacgg    780
tggtag                                                                786

SEQ ID NO: 207          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 207
atgaataatg aatcacaggc aaaagattct agtctgagaa tggaacctct ggagaaggaa    60
aaaggcgctg caggacaggg tgcgctcagt caaatcccgc ccgaatccta cagaaccaaa    120
tctcctgccg aattattggg tgcggggaaa actcgtgcag atctgaattt ccggatgtc    180
aaaaatgatt atgagctcga taatgcatta ataggccaaa ctgtaacctc aaacggttgt    240
gtggtcaaag caccatgggt gcgcaaggat tttaatacc ccggatattg gtccgagggt    300
tatatcaagc catgcgcagc gtaccttagc tatattaaaa aagatacgta tccgtcaggt    360
gcgaccagc attacaccac aacccagacc gtgggactga cagaaacctt tacgaaagag    420
gtgaaagctt cctattccgt tggcgctaac atcgatattg ttaacgtggg ctcatcaata    480
gagaccggct ttagccggtc ttccagttgg agccagcaaa ctattcaatc atggacaaca    540
acgttgcagg gtccacagga ttactggaca ttccagccgg tcttactgta tgcctggaag    600
gtgaacgcaa acgctctgtc ttatatgtcg cctaaaccga gtttatatta tacctctggt    660
aagacgacct atatttttc accagtattt cgcaattccc cctcaaccat tgataaggat    720
atagggtatc tgtcgttgca aacagtaatt gaatatatgt gcaacgaagc ctggtctcgt    780
tggtga                                                                786

SEQ ID NO: 208          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 208
atgaataacg agagccaggc aaaagatagc tcactccgta tggaacctt agaaaaagaa    60
aaaggtgcgg cgggacaggg cgcactgtca cagatcccgc cagaatcgta ccgtacaaaa    120
tctcctgcag aactgttggg tgctggaaaa acccgggcag atctgaattt ccctgacgta    180
aaaaatgatt atgagcttga caacgcactt ataggccaga cagtaacctc taacggctgc    240
gttgtgaaag caccttgggt gcggaaagat tttaatactc caggctactg gtccgagggc    300
tacatcaagc cttgtgcagc atatttgagc tatattaaga aagacacggt ccgtcgggc    360
gttcaggagg gttatacatt acgtaagaag aaaggctttt cgcgccagtt tactacctcc    420
acggaagtaa agagctcagt aaccgctggt tttttggctt gtgaagccac actggaagtc    480
accactagtt ttagttattc tgagaccatc gaagaagagt cgaagagac ctggaccaaa    540
acactcacag gaccacaaga ttattggaca tttcaaccgg ttttgctgta tgcctggaag    600
gtgaacgcca acgcgctgag ttacatgtcc cctaaaccga gtcttatta cacctcaggc    660
aaaacgacat atattttcag cccggtttt cggaattctc ctagcacaat tgataaagat    720
ataggttacc tgagcttgca aacagtgatc gaatatatgt gcaatgaggc gtggagtcgt    780
tggtaa                                                                786

SEQ ID NO: 209          moltype = DNA   length = 777
```

```
FEATURE              Location/Qualifiers
misc_feature         1..777
                     note = Synthetic
source               1..777
                     mol_type = other DNA
                     organism = synthetic construct
SEQUENCE: 209
atgaataacg aatcgcaggc caaagatagt tcattgcgca tggaaccact tgaaaaagaa    60
aaaggcgctg cagggcaggg ggcattgtca cagatcccgc cggaatcata tcgcaccaaa   120
tcaccggcag agttgttggg cgcaggcaag acacgggctg accttaactt tccagatgtg   180
aagaatgact acgaactgga taatgccctc atcggacaga ccgtaacatc gaatggttgt   240
gtggtgaagg cgccatgggt gcgtaaggat tttaacacgc cgggctactg gtcagaaggg   300
tacataaaac cttgtgctgc gtacttgagc tacattaaga aggacaccat tccgggagat   360
gaaacgcaca cgttccgtaa gtttaaaggt tttaccacgc ggtttgatac gtccatttcc   420
attacggccg gtgtgtccgg aggtgttttt ggttgtaatg cgtccctgga ggttactacc   480
gaattttcgt atggtcaaga aataaccgaa caaacagaag aaacgtggac gtcgactata   540
tacgctcaag attactggac cttccagccc gttctcctgt atgcatggaa agtgaacgcg   600
aatgcgctga gttatatgag tcccaaaccg tctctgtatt ataccTctgg aaaaacgact   660
tacatatttt cgccagtttt tcgtaattct ccttcgacga tcgataaaga tataggatat   720
ctgagcttac agactgtcat cgagtacatg tgcaacgaag catggagccg gtggtga      777

SEQ ID NO: 210          moltype = DNA  length = 783
FEATURE              Location/Qualifiers
misc_feature         1..783
                     note = Synthetic
source               1..783
                     mol_type = other DNA
                     organism = synthetic construct
SEQUENCE: 210
atgaacaatg agagccaggc gaaagattca tcacttcgca tggaaccctt agaaaaagag    60
aaaggtgctg cagggcaggg ggcgttgagt caaataccCC ctgaatcata ccgcacgaaa   120
agccccgcag aattgttagg agccggcaag actcgggctg atcttaattt tcccgacgtg   180
aagaatgatt atgaattaga caacgcactg attggccaga cggtgactag caacggctgc   240
gtcgtcaaag caccatgggt gcgtaaagac ttcaatacgc ccggctactg gtctgagggt   300
tacattaaac catgcgccgc atacctgtct tatattaaaa aagatacggt cccgggtacc   360
atggagaaaa cccttgagaa aaagaacggt tacagttccc gctttcaaac aagcgtggag   420
ataaaagctg gtctgtctgc cggtattttt ggctgcaatg cttctctgga agtaaccacg   480
gggtttacat atgagcagac catcacatct gaaacaaccg aaacgtggaa agaaacccTt   540
acaagcggtc ctcaagatta ctggacattt caaccagtac tgctgtatgc atggaaagtc   600
aatgctaatg cactttctta catgtcacct aaaccttctt tgtattatac cagcggtaaa   660
actacctaca tctTttcacc cgtatttcgt aattcgccat ctactataga taaggacatt   720
gggtacctta gcttacagac tgtaattgaa tacatgtgca atgaagcatg gtcgcgctgg   780
tga                                                                 783

SEQ ID NO: 211          moltype = DNA  length = 777
FEATURE              Location/Qualifiers
misc_feature         1..777
                     note = Synthetic
source               1..777
                     mol_type = other DNA
                     organism = synthetic construct
SEQUENCE: 211
atgaataatg aatcccaggc gaaggatagc agtttacgca tggaaccgct ggaaaaagag    60
aaaggcgcag ccgggcaggg cgccctgtcc caaatccccc cggagagtta tcggacaaaa   120
agtcccgccg aactgctggg tgccgggaaa actcgtgcag acctcaactt tccggacgtt   180
aaaaatgact atgagctgga taatgccctg attggtcaaa cagttacgtc gaatggttgc   240
gtagtcaaag cccctTgggt gcgcaaagac tttaatactc ccgggtattg gtccgaaggc   300
tatatcaaac catgtgctgc ctatcttTca tatattaaga aagatacgct tgccggcaca   360
gaagagcaca ccttgcggaa atttaaagga tacacctcac gattcacggc aagcgttgaa   420
gtcaaagctt ccgcgtcagc tggcatcttt gggtgcgaag cgtccctgga ggtaactacg   480
ggcttttctt acggagagga gattacgagg gaaaaagaag agacctggaa aaccactgtg   540
gcgccgcagg attactggac ttttcagccc gttttacttt atgcttggaa agtgaacgca   600
aacgctctgt cgtacatgtc tccgaaacct agcctgtatt acacgagcgg aaaaaccacc   660
tatatcttca gtcctgtgtt ccgtaactca ccgagtacaa tcgataaaga cattggctac   720
ctttccttgc agacggttat cgagtatatg tgtaacgagg cgtggagccg atggtaa      777

SEQ ID NO: 212          moltype = DNA  length = 777
FEATURE              Location/Qualifiers
misc_feature         1..777
                     note = Synthetic
source               1..777
                     mol_type = other DNA
                     organism = synthetic construct
SEQUENCE: 212
atgaataatg aatcgcaagc caaagatagc tcactcagaa tggaaccgtt agaaaaagag    60
aaaggagcgg ccggtcaagg ggccttatca cagataccgc cggaatccta tcggacaaaa   120
agtcctgcgg agttattggg cgccggaaag actagagcag acttgaactt ccctgatgtg   180
aaaaacgact atgagttgga taatgcttta atcggacaaa ccgtcaccag taacggatgc   240
gtagtgaaag ctccgtgggt gcgcaaggat tttaatacgc caggctactg gagcgaagga   300
```

-continued

```
tatatcaaac catgtgcggc gtacctgagt tatattaaaa aggataccct gtcaggaacc    360
tcagaacaca ccctgcgcaa acttaaaggc tatacatctc ggtttaatgt gtctgcggaa    420
ctgaaagcgg gtattaaagc aggaatattt ggttgtgagg ctagtctcga agttacgact    480
ggctttagtt atggtgagga tataagccaa gaaacagaag aaacgtggaa gaccactgta    540
gcgccccagg attattggac tttccagcct gtgttattgt atgcatggaa agttaatgct    600
aatgcactga gttacatgtc cccgaaaccc tcactgtact atacctctgg gaaaacgaca    660
tatatattca gtcccgtttt tcgaaattct ccgagtacaa tcgataaaga tatcggttat    720
ttatcgttgc agacggtgat agagtatatg tgtaacgaag cttggagccg ctggtaa       777

SEQ ID NO: 213            moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 213
atgaataatg agtctcaagc taaggatagc agtctgcgca tggaaccact ggagaaagaa    60
aagggcgctg cggggcaggg agcgttatct cagattccac cggaatcgta ccgtaccaaa    120
tctcctgcgg aactgttagg tgccgggaaa acgcgggctg acctgaactt ccccgacgtg    180
aaaaatgatt acgaattaga taatgccctg attggccaaa ctgttacgtc taatggttgt    240
gtagttaagg caccgtgggt acgaaaggat tttaatacac caggctattg gagcgaaggt    300
tacattaaac cttgtgcagc gtatctgtct tacatcaaaa aagatactat tccgcagaat    360
gccactcagc attatacgac tactcagacc gttgggctga cagagacttt tacgaaggaa    420
gtgaaagcat cctatagcgt tggcgcgaac atcgatatag ttaatgtcgg ttcctcgatt    480
gaaacaggtt tttcacgttc cagcgactgg tctcagcaga cgattcagag ttggaccaca    540
actctgcagg gtcctcagga ttattggact tttcagccgg tactgttata cgcttggaaa    600
gttaatgcca acgcgctctc atatatgagt cctaaaccaa gcttatacta cacatctgga    660
aagacaacct atatttttc gccggttttt cgcaattcgc cttctaccat cgataaggat     720
attggttatc tgagcctcca gacagttatc gaatacatgt gcaatgaggc gtggagtaga    780
tggtaa                                                               786

SEQ ID NO: 214            moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 214
atgaataatg aaagccaagc aaaggattcc agtctgcgca tggagccttt agaaaaagaa    60
aaaggagcgg ccgccagggg ggcacttagt cagattccgc ccgagagtta tcgaacaaaa    120
agccccgcag aactgctggg cgcgggaaaa acccgggcgg atttaaattt ccctgacgtt    180
aagaacgatt atgaactgga taatgcctta atcggtcaga ccgtgacctc taatggttgc    240
gtcgtaaaag ctccgtgggt tcgcaaggat tttaatacac ctggttactg gtcggaaggt    300
tatataaaac cgtgtgctgc ttatctttca tacatcaaaa aagacacagt tccttctggt    360
gttcaggaaa gttacagtct ttcgaaaaaa aaaggattta cgcggcagtt cacgacatcc    420
gccagtgtta cctccagcgt ttcagcgggt atcttcggat gtgaagcaag tttagaagtt    480
acaacagggt ttagttatag tgaaaccatt aacgaggaaa cgaccgaaac atggacgcgc    540
acattgaccg gcccccaaga ttattggacc tttcagccgg ttctgctgta tgcctggaaa    600
gtgaatgcga acgctttgtc atacatgtct ccaaaaccat ctctgtacta tactagcggt    660
aaaactacgt atatttcag cccggttttt cggaactcgc cgagcacaat agataaagac     720
attggttatc tgtccttaca gaccgttatt gaatatatgt gtaacgaggc ttggtcacgt    780
tggtaa                                                               786

SEQ ID NO: 215            moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 215
atgaacaatg agtcacaggc aaaggattca tctttacgta tggaaccccct ggaaaaggag   60
aaaggcgcag ccggtcaggg cgcgctctct cagatcccgc cggaatcata ccgtactaag    120
agtcctgcgg agttgttagg tgctggtaaa acgcgtgcag atcttaactt ccgcgacgtg    180
aagaatgatt acgaattaga taacgcccctt atcgggcaga ccgtgacgtc gaatgggtgc    240
gttgtgaagg cgccatgggt gcgaaaagac tttaatactc cgggggtattg gtccgaaggt   300
tacataaaac cctgtgcggc ctacctgtct tatattaaga aagataccat cccggatggg    360
acatcgagca gtcatacgtt tgaaaaaaaa aaagggtatt cgtccgaaac ctcagtttca    420
acagaggtaa aagcctcggt tggtgtcaat atattaggat gcgacgcgag catggaagtt    480
actacaggtt ttacttatac ccagggaatc tcttcagaaa caacggagtc atggacggac    540
actgtgacgg gaccgcagga ctactggacg ttccagccgg tgctgctgta tgcctggaag    600
gttaacgcta atgcctttgt atacatgtcc ccaaaaccat cactgtacta tacatcagga    660
aaaaccacct attttttc ccccgtattc cgtaattcac cctctacgat tgataaagat      720
ataggttatc tgtcgctcca gacagttatt gaatacatgt gcaatgaggc ttggagccgg    780
tggtaa                                                               786

SEQ ID NO: 216            moltype = DNA   length = 777
```

-continued

```
FEATURE             Location/Qualifiers
misc_feature        1..777
                    note = Synthetic
source              1..777
                    mol_type = other DNA
                    organism = synthetic construct
SEQUENCE: 216
atgaacaacg aatcacaggc aaaagacagc agcctgagaa tggaaccact tgaaaaggaa   60
aaaggggccg ccggtcaagg tgcgctcagt caaattccac cggaaagtta ccgtacgaaa  120
agcccggccg agctgcttgg tgctgggaaa actcgcgctg atctgaattt tcctgatgtt  180
aagaatgatt atgaactgga taacgcactg atcggccaga cggtcacctc aaacggctgt  240
gttgtaaagc ctccttgggt ccgcaaagat ttcaacacac cgggttactg gtccgagggt  300
tatattaagc cgtgtgccgc ttatttatca tacattaaaa aggatactct gagtggaacg  360
gaagaacaca cattgagaaa attcaaaggt tacacctcac ggttcacagc tagcgttgaa  420
gtcaaagcct cggcttcagc aggtattttt ggttgtgaga cgtctttaga ggtaacgact  480
ggattctcct atgccaaga gatcactgat gagaaagaag aaacttggaa aacaacagtg  540
gctccgcaag actattggac ttttcagccg gtactcctct acgcatggaa agtaaacgct  600
aacgcactgt cttacatgag tcccaaaccc tctctctact atacatcggg taaaactact  660
tatatctta gccccgtttt tcgcaacagc ccaagtacaa ttgacaaaga cattggatat  720
ctgagtctgc agacggtcat tgaatatatg tgtaatgagg cgtggtctcg ttggtaa     777

SEQ ID NO: 217          moltype = DNA  length = 786
FEATURE             Location/Qualifiers
misc_feature        1..786
                    note = Synthetic
source              1..786
                    mol_type = other DNA
                    organism = synthetic construct
SEQUENCE: 217
atgaacaacg aatcccaggc caaagacagt agccttcgta tggagccgtt agagaaagag   60
aaaggtgcgg ctgggcaggg cgcacttagt cagatcccac cggagagtta tcgtaccaaa  120
agccccgccg agctcttagg agcaggtaag acccgcgcgg atcttaactt tccggatgta  180
aaaaatgatt atgagttgga caatgcctta attggtcaga cggttactag caacggatgc  240
gtggtcaaag cgccgtgggt acgtaaagat tttaataccc ctggttattg gagcgaagga  300
tacataaaac catgcgccgc atatttgtca tatattaaga aggacaccat tccgcagcag  360
gtgactcaga cccgttctta tcagctgact aaagggcata ctcagagttt tacgaccagt  420
gtcagccgca aatacagcgt aggtgcaaaa attgatattg tgaacatcgg ttctgaaata  480
tccaccgggt tttcacaaac tgagtcttgg agtaccaccc agacatttac agaatccact  540
caattgaccg gaccccaaga ttattggacc tttcagccag ttctgttata tgcgtggaaa  600
gtcaacgcta acgcactgtc ttatatgtcc cctaaaccat cgctgtacta cacttctggg  660
aaaaccacct acatctttag cccggttttt cgtaacagcc cctcaaccat agataaagac  720
atcggctacc tttctctgca aacagtgatt gagtatatgt gtaatgaagc ctggtctcgc  780
tggtaa                                                              786

SEQ ID NO: 218          moltype = DNA  length = 777
FEATURE             Location/Qualifiers
misc_feature        1..777
                    note = Synthetic
source              1..777
                    mol_type = other DNA
                    organism = synthetic construct
SEQUENCE: 218
atgaataatg aaagtcaggc aaaagacagc tcactgcgta tggaaccact tgaaaaagag   60
aaaggtgctg ctggccaggg tgctttaagt cagatacctc cagaaagcta tcggacaaaa  120
tcgcctgcgg aattgttagg tgcaggcaaa acccgcgcag atctgaattt cccggatgtt  180
aaaaatgatt atgagttgga taatgcgctc ataggccaga cagttactag taatgggtgt  240
gttgttaaag cgccgtgggt ccggaaggac ttcaataccc cgggatattg gtctgagggt  300
tacatcaagc cgtgtgcggc gtatcttagc tatattaaaa aagatacgtt ggcaggaact  360
tcggaacata cgcttcgtaa actccgtggt tacactagcc gcttcaatgt cagcgcagag  420
gtaaaggctg gagttaaagg aggtattctt ggctgcgaag cgtcgcttga ggtgactact  480
ggtttctctt acggtcaaga aatcacgcag gaagcagagg aaacctggaa gactactgtg  540
tcgccccagg attattggac gtttcagcct gttctgctgt atgcatggaa agtgaacgcc  600
aacgctctgt cgtatatgtc cccaaaaccc tcactgtact acactagcgg aaaaacgaca  660
tatttttta gcccagtttt cagaaattca cctagcacca tagataaaga catcggctac  720
ctgagccttc agacagtaat cgaatacatg tgtaacgaag cctggtctcg ctggtaa     777

SEQ ID NO: 219          moltype = DNA  length = 777
FEATURE             Location/Qualifiers
misc_feature        1..777
                    note = Synthetic
source              1..777
                    mol_type = other DNA
                    organism = synthetic construct
SEQUENCE: 219
atgaataatg aatcgcaggc gaaagattcc agtctccgta tggaaccgtt agaaaaagaa   60
aaaggtgctg ccggacaggg tgcactgagc cagattccgc ctgaatcata ccgcacgaaa  120
tcgccagcag agttactcgg cgccggaaaa acacgggctg acttaaactt cccagatgta  180
aaaaatgact atgaattaga taatgcactc attggtcaaa cagtgacctc caatggctgt  240
gtagttaagg caccttgggt acggaaagac tttaacactc cggggtattg gagtgaagga  300
```

```
tatatcaagc cctgtgcagc atacttatcc tacatcaaaa aagatacagt agtgggcact   360
gtggagcaga ctatggagaa aaagaaaggt tttacaagtc gctttaatgc tagtacggaa   420
ataaaagcgt cagcctccgc tgggtttttt gggtgtgaag cgtctctgga agtaacgact   480
ggctttgagt atgaggagac agtgacatcg gaaacaactc atacttggaa acaaaccctg   540
acagaacagg actactggac gtttcagcca gtattactgt atgcatggaa agttaacgcg   600
aatgcgctta gttatatgtc cccgaaacca tcattgtact atactagtgg taagaccacg   660
tatatattct cacccgtctt tcgaaatagt ccatctacaa tagacaaaga tattggctac   720
ctgagcttac agaccgttat tgaatatatg tgtaatgaag cctggagtag atggtaa     777
```

```
SEQ ID NO: 220          moltype = DNA   length = 774
FEATURE                 Location/Qualifiers
misc_feature            1..774
                        note = Synthetic
source                  1..774
                        mol_type = other DNA
                        organism = synthetic construct
SEQUENCE: 220
atgaataatg aaagtcaggc gaaggacagt agtctcagaa tggaaccact cgagaaagaa   60
aagggtgcgg ctggtcaggg tgctttatcc cagataccac ctgagtctta tcggacgaaa   120
tcgccagctg aattattagg ggcaggaaaa acgcgcgccg acctgaattt cccgatgtg    180
aaaaatgact atgaactcga taacgccctc attgggcaaa ccgtcacttc aaatggctgt   240
gtagtaaaag ctccatgggt acgtaaagat tttaataccc cgggatattg gtcagaagga   300
tacattaagc cgtgcgccgc ttatctgagt tatattaaaa aagatacact tggtacggaa   360
gaacacacgc tccggaaatt caaagggttt acgagccgct tcacagctag catggaagta   420
aaagcagggg taaaggccgg tatttttggt tgcgaggcgt cgcttgaagt taccacgggt   480
tatagttacg gggaagacat taccgaagaa aaagagagaaa tttggaagac cacggttagc   540
ccgcaggact actggacttt tcagccagtt ctgctgtacg cgtggaaagt caacgcgaac   600
gccctgagct atatgtcacc aaaaaccttcg ctttattata ctagtggtaa aactacgtac   660
attttttcgc ctgtctttcg caactcccca agcaccattg acaaggatat tggctacctt   720
tctcttcaga cagtaattga gtacatgtgt aacgaagctc ggagtcgctg gtaa          774
```

```
SEQ ID NO: 221          moltype = DNA   length = 780
FEATURE                 Location/Qualifiers
misc_feature            1..780
                        note = Synthetic
source                  1..780
                        mol_type = other DNA
                        organism = synthetic construct
SEQUENCE: 221
atgaataacg agagtcaggc taaagatagt tcactgcgca tggaaccact cgaaaaagaa   60
aaaggtgctg ctggccaagg tgccttaagt cagataccc cagagagcta tagaaccaag   120
tcgccggcgg agctttagg cgcgggcaag actcgggctg atctgaactt tcctgacgta   180
aagaatgatt atgagttgga taatgctctt attggacaaa ctgtaacctc taatggttgt   240
gtggttaaag cgccatgggt cagaaaaagat tttaatacgc cgggttactg gtccgaaggt   300
tacattaaac cgtgtgcagc ttatctgtca tacatcaaaa aagatactgt cgtgggtaca   360
caagaacacg aactcactaa aaagaaaggt tattctacaa cttttcactgc gagcacatcg   420
cttaaatctt ctatatcggg tggtatcggt gagtgcgagg cgagctttga ggtgactact   480
gaatttttcct actcacagaa ctcttacgaa gagaaatctg agacctggac cacaacctg   540
acgggtccac aggattattg gacgtttcaa cctgtacttt tgtatgcgtg gaaagtgaat   600
gcaaacgcac tgtcatacat gagtccaaag ccatcattat attatactc aggtaagacg   660
acctatattt tctcaccggt cttcagaaat agcccatcta ccattgataa agacattgga   720
tacctgtctc tgcagactgt gattgaatac atgtgcaatg aagcctggtc tcggtggtaa   780
```

```
SEQ ID NO: 222          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 222
atgaataatg agtcccaagc aaaggatagc agcttgcgga tggagccact cgaaaaagag   60
aaaggagcag ctggtcaagg tgcactgagc cagattcctc cggagtcata ccgcaccaaa   120
tcacctgcgg aattgctggg agcgggggaag acacgggccg atttaaattt tcccgatgtc   180
aaaaacgact atgaactgga caatgcttta ataggccaaa cagtaacctc aaatggttgt   240
gttgtgaaag caccttgggt tcggaaagat tttaatacac cggggtattg gagtgaaggc   300
tacattaaac cgtgtgcagc ctatctgtcg tacataaaaa aggatacact ggatgtcgcc   360
gacacagtgg gccaggtgct caacatgcgt aaaggttttt caaatcgctt taccgcttct   420
aaagcgttaa aagcacttat tagtgaggga gttgcaggct gcgatacgtg ccacgaggtt   480
acaaccaaat ttgactatat actggagacg ataaaagacg agtcgaaaca accgttttcc   540
gatcctgtgt ctgttgttcc gagtcagctg tgccagccgg ttctgctgta cgcatggaag   600
gtcaatgcga atgctcttag ttatatgagc ccaaagcctt cgctgtatta tacaagcggc   660
aaaacgacgt atattttcag ccctgttttt cggaactcgc cgagcacaat agacaaggat   720
atcggctacc tgagcctgca gacagtcata gagtacatgt gcaatgaagc atggtctaga   780
tggtag                                                              786
```

```
SEQ ID NO: 223          moltype = DNA   length = 786
FEATURE                 Location/Qualifiers
misc_feature            1..786
```

-continued

```
                        note = Synthetic
source                  1..786
                        mol_type = other DNA
                        organism = synthetic construct
SEQUENCE: 223
atgaataatg aaagtcaggc caaagattca agtctgcgaa tggagccgtt ggaaaaagaa  60
aaagggggcgg caggacaggg ggccctgtcc cagattcccc ctgaaagcta ccgaaccaaa  120
tctcctgcgg agctgcttgg cgcgggcaaa accagagccg atctcaattt tccagatgtg  180
aaaaatgatt acgaacttga caacgcttta ataggtcaaa cagttacttc caatgggtgc  240
gtggttaaag ccccatgggg ccgcaaagac tttaatactc caggttattg gtctgaaggt  300
tatattaaac catgcgccgc atatctgtcg tacatcaaga aagataccat accaagcggc  360
acctccatcg agtacagcct gacgaaaaaa aaaggttttt cacggcagtt caccgtaagt  420
gcggaagtca aggttggcgt ttctgcgggg atctttggtt gtgaaacgtc cttagaggtt  480
actacaggct tttcctattc tgaagatatc aacgaagaaa ctactgaaac atggaaaaaa  540
gttgccacgg gtccacagga ttactggacg tttcaaccgg tactgctgta cgcgtgtgaaa  600
gtcaacgcta acgcgttgtc ctatatgagc ccgaaaccta gtctgtacta cacttcagga  660
aaaacaacgt acatttttag ccctgttttc cggaacagtc cgtcaacaat tgataaagat  720
atcgggtatc tgagtttaca gaccgttata gaatatatgt gcaatgaggc ctggagccga  780
tggtga                                                             786

SEQ ID NO: 224            moltype = DNA   length = 786
FEATURE                   Location/Qualifiers
misc_feature             1..786
                         note = Synthetic
source                   1..786
                         mol_type = other DNA
                         organism = synthetic construct
SEQUENCE: 224
atgaataatg agtcgcaagc aaaagatagc agtttgcgga tggagccgct ggagaaagag  60
aagggtgctg cggggcaggg tgccctttct cagattcccc ctgaaagcta tagaacgaaa  120
agcccggcgg aattactcgg cgcgggcaaa acacgcgccg atcttaattt tccagacgtg  180
aaaaacgatt acgagctgga taacgcactg atcggccaaa ccgttaccag caatggttgt  240
gtggtgaagg ctccctgggt ccggaaggat ttcaatacgc ctggttactg gagcgaaggt  300
tatattaaac cgtgtgcagc ttatttatcc tacatcaaga aggacaccat tccatctggt  360
acaagcatcg aatacagctt gacaaagaag aagggcttct cccgccaatt caccgtcagc  420
gcggaagtaa aggttggcgt ttccgctggt attttcggtt gcgaaactag ccttgaagtg  480
actaccggtt tcagttatgg tcaggatatc aatgaggaga cgacagagac atggaaaaaa  540
acgctcaccg ggccacagga ctattggaca tttcaaccgg ttttgctcta cgcctggaag  600
gtgaatgcga acgcccttag ttacatgagc ccaaagccaa gtctgtacta tacatccggt  660
aaaaccacct atatcttcag tccagttttc cgcaattctc ctagcaccat cgataaagat  720
atcggatatt tatcattaca gacagtaatt gagtacatgt gtaatgaagc ttggtcacgt  780
tggtag                                                             786

SEQ ID NO: 225            moltype = DNA   length = 786
FEATURE                   Location/Qualifiers
misc_feature             1..786
                         note = Synthetic
source                   1..786
                         mol_type = other DNA
                         organism = synthetic construct
SEQUENCE: 225
atgaacaacg agagccaagc taaagactct agcttgagaa tggaaccact tgaaaaagag  60
aaaggcgccg ccggtcaggg ggccctgagt cagataccac cagaatcata ccggacgaaa  120
agcccggcgg agcttttggg tgcgggaaag accagagccg accttaattt tcccgatgtt  180
aaaaatgatt atgagctgga taatgccctg attggtcaga cggtgacttc caatggatgc  240
gttgttaagg ccccttgggt acgcaaggat tttaacaccc cgggctattg gtcagaagga  300
tatatcaaac cgtgcgctgc gtacttgagt tacattaaaa aggacactat tccatcaggg  360
acaagcatcg aatattcttt gactaaaaag aaggggttta gtcggcaatt cacagtgtct  420
gcagaggtaa aagtcggcgt atcggcgggt atctttggtt gtgagacatc attagaggtt  480
acgaccgggt tttcctacgg ccaggatatc aatgaggaaa caaccgagac gtggaaaaag  540
gttgcgaccg gtcctcaaga ctattggacc tttcaaccgg tcctgttata tgcctggaaa  600
gtgaatgcaa atgcactgtc ttacatgtca ccaaaaccct ctttatatta tacgtctgga  660
aaaacaactt atattttctc ccccgttttt agaaattcac catcaactat tgataaggat  720
ataggctatt tatcgctgca gacggtaatc gagtatatgt gcaatgaagc atggagtcga  780
tggtga                                                             786

SEQ ID NO: 226            moltype = DNA   length = 786
FEATURE                   Location/Qualifiers
misc_feature             1..786
                         note = Synthetic
source                   1..786
                         mol_type = other DNA
                         organism = synthetic construct
SEQUENCE: 226
atgaataacg aaagccaagc caaagatagt agcttacgta tggaaccttt ggagaaagag  60
aaaggtgcgg cagggcaagg tgcgctgagt cagatcccgc ctgagagcta tcgtacgaaa  120
agtccggcgg agctgttggg agcgggtaag acgcgcgcgg acttaaactt tcctgacgtg  180
aagaatgatt acgaattaga taacgctctt atcggacaaa ccgtcacttc gaatgggtgc  240
gttgtgaaag ctccgtgggt gcggaaagac tttaatacgc cgggttattg gagcgaaggt  300
```

-continued

```
tatataaaac cgtgtgcagc atacctgagt tatataaaaa aagacaccat accgtctggc   360
gtacaggagt cgtattctct gacaaagaaa aagggtttta gcagacagtt tacagtttct   420
gctgaagtta aggttggggt ttccgcgggt atctttggat gcgagaccag cctggaagtg   480
accacgggtt ttagttacag tgaagatata aatgaggaaa ccacagagac ctggaaaaaa   540
acactgacag gcccacagga ctattggacg tttcagccgg ttttgctcta tgcttggaag   600
gtgaatgcaa atgcattatc ctacatgtca cctaaaccca gcctgtacta tacatccggt   660
aaaaccactt atatcttttc tccggtattc cgcaatagcc ctagcaccat tgataaagac   720
atcggatatc tgtcgctgca gaccgtaatt gaatatatgt gcaatgaagc ttggagccgg   780
tggtaa                                                              786
```

SEQ ID NO: 227          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 227
```
atgaataatg aaagtcaggc caaggattct tctctgcgga tggaacctct ggaaaaagag   60
aaaggggcgg cgggccaggg agcattatct cagattcctc ctgagagcta tcgtacgaaa   120
tccccggcgg aattactggg tgcggggaaa acgcgcgcag acttgaattt tccggatgta   180
aaaaatgact atgaactcga taacgcactg atttgggcaga cggtgacgag taatgggtgc   240
gtggtgaaag ccccatgggt ccgtaaagat ttcaataccc caggctactg gtcggaggga   300
tatatcaaac cttgcgcagc gtatctgagc tacattaaaa aagacactat tccttccgga   360
acttctattg agtattcgct tacaaaaaaa aaaggcttca gccgccagtt tacagtgtct   420
gccgagtcaa aggtgggtgt ttctgccggt atatttggct gcgaaacgtc gctcgaagta   480
acgacgggtt tcagctactc cgaagatatt aatgaggaga caacagaaac gtggaagaaa   540
acgctgacag gtccacagga ttattggacg ttccaaccgg tgctgctcta cgcttggaaa   600
gttaatgcaa atgcgcttag ttacatgtcg ccgaaacctt cactttacta tacaagcggc   660
aaaacaacat atatctttag tcccgtattt cgtaacagtc cttctacaat tgacaaagat   720
attggttatc tttcgctgca aacagtcata gaatacatgt gcaatgaagc ttggtcacga   780
tggtga                                                              786
```

SEQ ID NO: 228          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 228
```
atgaacaacg aatcacaggc caaagactct agtctgcgga tggaaccgtt ggagaaagaa   60
aaaggcgctg cgggccaggg ggcgctgtca cagattcccc ccgaaagtta tcgcactaag   120
tcaccggcag aacttctggg ggcaggaaaa acgcgcgctg accttaactt ccccgatgtc   180
aaaaatgact acgaactgga taatgctctg attggccaga cggtaacgag taatggctgc   240
gttgttaaag ctccctgggt gcgtaaggat tttaataccc ccggttactg gagtgaaggc   300
tatataaagc cgtgcgcagc atatttatct tatattaaaa aagatacaat cccgtcgggc   360
acttctatcg aatatagctt gacaaaaaag aagggtttta gcagacaatt taccgtgtcg   420
gcagaggtaa cggttggggt cagtgcgggt attttcggtt gcgaaaccag tcttgaagtt   480
actactggtt tcagctatag cgaagacatc aacgaagaaa ccactgaaac ctggaaaaaa   540
accttaacgg gcccgcaaga ttattggact ttccagcctg ttttgttata tgcctggaaa   600
gtgaatgcca atgcattgag ttatatgagc cctaaacctt ctctgtatta tacatcggga   660
aagaccacct atatcttctc tccggtgttt cgtaactcgc cctctactat cgacaaagat   720
ataggctatc tgagtctgca gacggtaatt gagtatatgt gtaatgaagc gtggtcacga   780
tggtaa                                                              786
```

SEQ ID NO: 229          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 229
```
atgaataacg aaagccaggc caaggatagt tccctgcgca tggagccttt ggaaaaagag   60
aaaggcgccg ctggccaggg cgctctttca cagataccac ctgaatcgta ccgcaccaaa   120
tctccagctg agctgctggg agcgggcaaa acgcgagcgg atctgaattt cccagatgtc   180
aagaatgatt atgaacttga caatgcgttg atcggtcaga cagtgacaag taacggctgc   240
gttgtcaaag cgccgtgggt ccgcaaagat ttcaacaccc ctggttattg gtccgaggga   300
tatattaaac cctgtgccgc gtacctgtca tacataaaga aagacaccat acccagcggt   360
accagtatag aatactcctt aaccaaaaag aaagggttta gccgtcagtt tactgtttct   420
gcagaggtga agttggggt gtctgctgga attttttggct gtgaagcctc cttagaagta   480
actactggct tttcttacag cgaagatata aatgaggaga ccactgagac ctggaagaaa   540
acattaacgg gtcctcagga ttattggacg tttcaacctg tgctgttata taccagtggc   600
gtcaatgcca atgcacttag ctatatgagc ccaaagcctt cactgtatta taccagtggc   660
aaaacgacct atatctttag ccccgtattt cgtaatagcc catctaccat agataaagat   720
ataggttatc tgtcattaca aacagtcata gaatacatgt gcaatgaggc gtggtctcgc   780
tggtaa                                                              786
```

```
SEQ ID NO: 230           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 230
atgaataatg aatcacaggc aaaagactca agcctccgca tggaacctct tgagaaagaa    60
aagggagcgg ctggtcaagg agcactgtcg caaatcccgc ccgagtcata ccgcacaaag   120
agcccagccg aattactggg cgccggcaag acacgcgcag atctgaactt ccccgatgta   180
aagaacgatt acgaattaga taatgcactg ataggccaga ccgtaacaag caatgggtgt   240
gtggtaaagg caccgtgggt ccgcaaggac tttaacacac ccggctactg gagtgagggt   300
tatatcaaac cttgcgctgc atacttatcg tatattaaaa aagacacgat cccttcaggc   360
acgtcgattg aatacagttt gaccaaaaaa aaagggttca gcagacagtt tacagtatcc   420
gctgaggtta aagtgggtgt ttcggctggc atatttggtt gtgaaactag tctgtgaagtt   480
acgacggggt ttagctactc cgaggatata aatgaggaga ccacggagac ctggaaacgc   540
acattaacag gacctcaaga ctactggacc ttccagcctg tgttgctgta cgcatggaaa   600
gtcaacgcta atgccctgag ttacatgagc cccaaaccga gcttatatta tacgagcggt   660
aaaacaacgt atatcttttc cccagtattt cggaatagcc cgtctactat cgacaaggat   720
atcggttacc tgagcttaca gactgtgatc gaatatatgt gcaatgaggc gtggtcacgc   780
tggtaa                                                               786

SEQ ID NO: 231           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 231
atgaacaacg aatcgcaggc aaaagactcc tcccttcgga tggaaccgct tgagaaagag    60
aaaggtgcag caggtcaggg ggccttgagt caaatcccgc ctgaatccta ccgtacaaaa   120
tcgccggctg aacttcttgg ggcgggcaaa acacgaccg atcttaactt ccccgacgtt   180
aaaaatgact acgaattgga caacgcactg attggtcaga ccgttactag caatgggtgt   240
gtcgtaaagg cgccgtgggt ccgaaaagat ttcaacacac caggttactg gtccgaaggt   300
tacattaaac catgtgcagc atatctgtcg tatattaaaa aagacacgat accatcgggc   360
gtgcaggaag gctacacctt acgcaaaaag aagggcttct ctcgtcaatt tacggtatca   420
gccgaagtca aaagttcagt cacagcgggg tttctggcct gtgaagctac attggaggtt   480
acgacaagct tcagttatag cgaagacatt gaagaagaat ttgaggaaac atggactaaa   540
accttgactg gcccacaaga ctattggacc tttcaaccgg tcctgctgta tgcgtggaaa   600
gttaatgcga acgcactgtc ctatatgtcc ccaaaaccat cgctgtatta cacctcaggt   660
aagacgacct acatttttttc acctgttttt cgcaatagcc catccaccat tgataaagat   720
atcggttatc ttagtcttca gaccgtgata gaatacatgt gcaatgaagc ttggtcacgc   780
tggtag                                                               786

SEQ ID NO: 232           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 232
atgaataacg aatcgcaagc aaaggattcc tcactgcgta tggaacctct ggaaaaagaa    60
aagggcgcag ccggacaggg agctttaagt cagatccctc ccgaaagtta tcggacaaag   120
tctccggccg aactgctggg tgcgggtaag acaagagctg atttaaactt cccggatgtg   180
aaaaacgatt acgaactgga taatgccctg attggccaga cagtaacatc gaacggatgc   240
gtagttaaag cgccatgggt gcgtaaggac tttaatacac caggttactg gtcagaaggc   300
tatattaagc cttgtgtgag gtatctttcg tatattaaga aagacaccgt gccatcgggc   360
gtccaggaag gttatactct gcgtaaaaag aaagggtttt cgcgtcaatt tacgacgtcg   420
acagaagtaa aatcttcagt gactgctggt ttccttgcgt gcgaagctac gttagaagta   480
acgacgtcat tttcgtatgg ccaggatatt gaagaggaat cgaagaaac ttggaccaaa   540
accttaacag gcccgcaaga ttactggaca tttcaaccag tgttgttata tgcatgaaa   600
gtgaacgcaa atgcattatc gtacatgtct ccgaaacctt cgctgtatta taccagcgga   660
aaaactacgt acatatttag ccctgtattc agaaattcgc catcgactat cgataaggac   720
attgggtatc tttcattgca gactgtaatt gagtacatgt gcaatgaagc atggagtcgt   780
tggtga                                                               786

SEQ ID NO: 233           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 233
atgaacaatg aatcacaggc aaaggatagc tcgcttcgca tggaacctct ggaaaaagaa    60
aaaggtgcag ctggccaggg cgcactgtcg cagatcccac ctgagtctta ccgaacgaaa   120
```

-continued

```
tcacccgcgg agttattagg ggcgggtaaa actcgcgccg acctcaactt tcctgatgtt    180
aagaatgact atgaactgga taatgcatta attggtcaga cggtgacatc taacggctgt    240
gtggtaaagg cccctgggt  tcggaaagat ttcaatacgc cgggctattg gagcgagggc    300
tatataaac  cgtgcgccgc ctatttgagc tatattaaaa aagatacagt accatcgggt    360
gttcaggaag gttatacgct ccgtaagaaa aaagggtttt ctcgacaatt tactactagc    420
acggaagtta aaagcagtgt tacagccgga ttccttgcct gtgaagcaac tttagaggtg    480
accacaagct tcagttactc tgaaacaatt gaagaagagt ttgaggagac ttggaccaaa    540
acggtggcgg gtcctcaaga ctattggaca tttcagcctg ttctgctgta cgcgtggaaa    600
gtgaatgcga acgcgctgtc atacatgagt cctaaaccga gcttatacta tacgagcgga    660
aaaactacat atattttttc accggttttc cgtaattctc cctctacgat tgataaggat    720
attggttatc tgagcctcca gaccgtcatc gaatacatgt gcaatgaggc ttggagtcgc    780
tggtga                                                               786

SEQ ID NO: 234          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 234
atgaataatg agagtcaggc aaaagattcc agtcttagaa tggaaccgct ggaaaaagag    60
aaaggcgcag cgggccaggg tgcgttgagc caaataccac ctgaatctta tcgtacaaaa    120
tcacccgcgg aactgcttgg tgcagggaaa acccgcgcgg atttgaattt cccagatgtt    180
aaaaatgatt acgaactgga caatgcgctg ataggccaga cagtgacgtc taacggctgt    240
gttgttaaag cgccttgggt tcgtaaagat tttaacaccc caggctactg gtcggaaggc    300
tatataaagc cttgcgcagc ttacctcagt tacatcaaga aagacacgat tccgtctggc    360
gttcaggaag gctatacatt gcgcaaaaaa aagggctta  gtcgacagtt tacggtatct    420
gcagaagtga aaagctcagt tactgccggc tttctcgcgt gcgaagctac ccttgaggta    480
acaacaagct tctcatatgg acaggatatt gaggaggagt ttgaagagac ttggacgaaa    540
acgcttactg ggccgcaaga ctattggaca ttccaacctg tgttgctcta tgcgtggaag    600
gttaatgcaa atgcactgag ctacatgagt cctaaacctt ctttatatta tacgtcaggg    660
aaaactacct acatattttc cccagtcttt cgtaactcgc cgagcactat agacaaggat    720
atcgggtatc tctctcttca gaccgtcatt gaatacatgt gcaacgaagc ctggtcgcgg    780
tggtga                                                               786

SEQ ID NO: 235          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 235
atgaataacg aaagtcaggc caaagattcg tccctgcgta tggagccact ggaaaaagag    60
aaaggtgctg cagggcaggg tgccttatca caaataccgc cggaatccta ccgcaccaaa    120
tctccagcgg aattgctggg agctggcaaa acgcgcgcag atttaaattt ccctgacgtt    180
aaaaacgact atgagttaga taacgcactg ataggacaga cggtgacaag taatggatgt    240
gtggtgaaag caccgtgggt tcggaaggac ttcaatacgc cggggtactg gtcagaaggc    300
tatattaaac cgtgtgcggc atatctctca tatatcaaaa aggatactat ccctagcggc    360
gttcaggaag ggtatacgct gcgtaaaaaa aaaggattca gtcgccaatt taccgtttct    420
gcagaagtaa agtcaagcgt gactgctgga tttttagcat gcgaagctac actggaagtg    480
actacgagtt tctcatatag cgaagatatt gaagaagaat ttgaagagac gtggacaaag    540
acggtcgctg gccctcaaga ttactggaca ttccaaccag tcttattata cgcgtggaaa    600
gtgaatgcaa atgcactgtc ttatatgagc cctaaacctt cctatatta  tacaagcggc    660
aaaacaacat acattttcag cccggtgttt cgtaacagtc catctaccat tgataaagat    720
attggatacc tttctctgca gaccgtcatc gaatacatgt gcaatgaagc atggtctcgc    780
tggtaa                                                               786

SEQ ID NO: 236          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 236
atgaacaatg agtctcaggc aaaagattct tctctccgta tggaaccttt agaaaaagag    60
aaaggcgccg ccggccaggg tgctcttagt caaatcccac ctgaaagtta ccgtactaag    120
tccctgcag  aactgttagg cgcaggtaaa acacgcgccg acctgaactt ccgggacgtg    180
aaaaacgatt atgaactgga caacgcttta ataggccaaa ccgtgacgtc aaatggctgc    240
gtggttaaag cccctggt   tcgcaaggat tttaatactc cgggatattg gagtgaagga    300
tacattaaac cgtgtgctgc atacctttcc tacattaaaa aggatacagt gccgtctggg    360
gtgcaagaag ggtacacctt acgaaagaaa aaaggcttta gtcgccagtt cactacatct    420
accgaagtca gtcatctcgt caccgcgggc tttctcgcat gcgaagcaac gcttgaagtg    480
acaacgtcat tctcatacgg ccaagatatt gaagaagaat cgaagagac  atggaccaaa    540
actgtcgctg gcctcagga  ttattggacg ttccaaccgg tcttattgta tgcatggaaa    600
gtgaacgcga atgcccttc  ctatatgtca ccgaaaccga gtttgtatta tacgtctggg    660
aagactacct acatttttag cccggtgttt cgtaactctc ctagcaccat tgataaagat    720
```

-continued

```
atcggttacc tgagcttgca gactgttata gaatatatgt gtaacgaagc atggtctcgc   780
tggtaa                                                              786

SEQ ID NO: 237          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 237
atgaacaacg aaagccaggc caaagacagt tcgttgcgta tggagccgtt agaaaaggaa   60
aaaggtgccg caggccaggg cgcgcttagc cagataccac cagaatcgta tcgaaccaaa   120
tcaccggccg agcttctggg agcaggtaaa actcgtgcgg atctgaattt cccagatgtt   180
aaaaacgatt acgaactcga taacgctctg atcggccaga cggttacgag caacggctgt   240
gtcgtaaaag ccccgtgggt ccgaaaagat ttcaacacac cggggtattg gtcagagggc   300
tatatcaaac catgtgccgc ctatttaagc tatatcaaaa aggacaccat acccagcgga   360
gtgcaggaag gctacaccct ccgtaagaaa aagggttct ctcgtcaatt tacagtgtca    420
gcagaagtta aatctagcgt aactgctggc ttcctggcct gtgaagctac attagaagta   480
accacctcat tttcatacgg ccaggatatt gaagaagaat ttgaagaaac ttggaccaaa   540
accgttgctg ggccccagga ttattggacc ttccagccgg ttttattgta cgcctggaaa   600
gtaaatgcaa acgccttatc atatatgagt cccaaaccgt cactttatta cacctcaggc   660
aagactacct acattttag ccctgtgttc cgcaatagcc cttcaaccat tgacaaagat    720
atcgggtatc tttccttaca gaccgtcatt gagtatatgt gtaatgaagc atggtcgcgc   780
tggtaa                                                              786

SEQ ID NO: 238          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 238
atgaacaatg agtcacaggc caaagacagc tcattacgaa tggaacctct cgaaaaggaa   60
aagggcgccg cgggtcaggg tgctctctct cagataccgc ccgagtccta ccgtacaaaa   120
tctcctgcgg agttgctggg ggcgggcaag acccgtgctg acttaaattt ccctgatgtt   180
aaaaatgatt atgaactgga taatgcgtta attggtcaaa cggtgacaag taacggctgt   240
gtcgtgaaag caccgtgggt tcgaaaagat ttcaacacgc ctgggtattg gtccgagggt   300
tatataaaac cgtgcgcggc ctatctcagt tatataaaaa aggataccat accatctggc   360
gttcaggaat cttatagcct ctctaaaaaa aaaggcttta ctcgtcagtt taccgtcagt   420
gccagcgtaa cgagttccgt tagtgcgggt attttcggtt gtgaggccag ccttgaagtt   480
acgacaggct ttagttactc cgaggatatc aatgaagaaa ctaccgaaac ctggactcgt   540
acgttaacgg gtcctcagga ttattggacg tttcaaccag tacttttgta tgcatggaag   600
gttaatgcca acgcactgtc ctacatgtcc ccgaaaccaa gtttgtatta cacaagtggg   660
aaaacgacct atatcttctc accggttttt cgaaattccc cgtcaacgat cgacaaagac   720
ataggctacc tttcattaca gactgtaatc gaatatatgt gtaatgaagc gtggagccgt   780
tggtga                                                              786

SEQ ID NO: 239          moltype = DNA  length = 786
FEATURE                 Location/Qualifiers
misc_feature            1..786
                        note = Synthetic
source                  1..786
                        mol_type = other DNA
                        organism = synthetic construct
SEQUENCE: 239
atgaataacg aaagtcaagc caaagatagt tctctgcgta tggagcccct tgaaaaagaa   60
aaaggagccg ctggacaggg tgctttatca cagatcccac cagaatcata tcgcaccaaa   120
tccccagcgg aattgctggg agcagggaag actcgtgcag atttaaattt ccctgatgtg   180
aaaaatgatt atgagctgga taatgccctg attggacaga ccgttacatc taacggttgt   240
gtagtaaaag cccctgggt gagaaaagat ttcaatacac caggctattg gtctgagggg   300
tacattaaac catgcgcggc ttacctctca tatattaaga aagatacggt ccccagcgga   360
gtacaggagt catattcact gagtaaaaag aaaggttta cccggcagtt tacgacgagt   420
gccagcgtga cctcttcggt ttcagcgggt attttttggtt gtgaggcctc actggaagtg   480
acaacgggtt tctcttacgg acaagacatc aacgaagaa cgaccgaaac ctggactcgt   540
acgttgacgg ggccccagga ttactggacc tttcaacccg tgctgcttta cgcatggaaa   600
gttaatgcaa acgccctgtc atacatgtca cctaaaccga gcttgtatta tacaagcggt   660
aaaaccactt atattttcag tccggtattt cgcaactctc cgagtaccat cgataaagat   720
atcggttacc tttctttaca gacagtaatt gagtatatgt gcaacgaggc gtgggagtcgc  780
tggtaa                                                              786

SEQ ID NO: 240          moltype = DNA  length = 786
FEATURE                 Location/Qualifiers
misc_feature            1..786
                        note = Synthetic
source                  1..786
                        mol_type = other DNA
                        organism = synthetic construct
```

```
SEQUENCE: 240
atgaataatg aaagtcaggc caaagattcg tcgctgcgta tggagccatt agaaaaggag   60
aaaggcgccg cagggcaagg tgcattgtct caaataccac cagaatccta tcgcacgaaa  120
tctccagccg aactcttagg agcaggaaaa acaagagctg atctgaattt tccggacgtc  180
aaaaatgatt atgaactcga taacgctttg attggtcaga ccgtcacctc gaatggttgt  240
gtggtaaaag cgccgtgggt gagaaaagat tttaatacac cgggctattg gagcgagggc  300
tatataaaac cgtgtgctgc ctacttgtca tacattaaaa aagacacggt gccgagtggt  360
gtccaagaat cttacagctt gtctaaaaag aaaggattca cccgacagtt tacgacaagt  420
gcctcggtga cctcgagcgt ttcagcaggg atctttgggt gtgaagcgag ccttgaggtc  480
accaccggtt ttagctacag cgaaacgatc aatgaagaaa cgaccgaaac atggacgcgc  540
gtcgcaaccg gcccacagga ttattggact ttccagccag tgctcctttta cgcctggaaa  600
gtgaacgcga atgcattgag ttatatgagt ccgaaacctt ccctctacta tacatctggt  660
aagacgacgt atatatttag tccggtgttt cgcaactccc ctagtacgat tgataaagat  720
attggttatt tgtccctgca gaccgtaatt gaatatatgt gtaacgaggc atggagtcgc  780
tggtaa                                                            786

SEQ ID NO: 241       moltype = DNA   length = 786
FEATURE              Location/Qualifiers
misc_feature        1..786
                    note = Synthetic
source              1..786
                    mol_type = other DNA
                    organism = synthetic construct
SEQUENCE: 241
atgaacaatg aatctcaagc taaagatagt tcgttacgta tggaaccgtt agaaaaggag   60
aaaggtgctg ctggccaggg tgctttatcc caaatacctc cagaatcata ccgcactaaa  120
tctccagccg aacttcttgg tgcaggtaaa acccgtgccg atttgaactt tccagatgtt  180
aagaatgatt atgaattgga taacgcactc attggacaaa ccgttacaag caatggttgc  240
gtcgtgaaag cgccctgggt gcgcaaggat ttcaacacac cgggatattg gtccgaagga  300
tacatcaaac cgtgtgcagc atacctgagc tacattaaaa aggatacgat tccgtcaggt  360
gtgcaggagt catactcact gagtaagaaa aaaggcttca cgcgccagtt tactgtgtct  420
gctagcgtca caagttcagt aagcgccggg atatttgggt gcgaggcatc cctggaagtg  480
actacaggct tttcgtatgg tcaggatata aatgaagaga ccacggaaac gtggacccgt  540
acccttacag gtcctcaaga ctattggact tttcaaccgg tgttactcta cgcctggaaa  600
gttaacgcaa atgctctttc gtatatgtct ccaaaaccat ctctgtatta taccagcggt  660
aagaccacct acatttttc cccggtattc cgtaactcac cgagcacaat tgataaggat  720
attggttatc tgtctttaca gaccgtaatt gagtatatgt gcaatgaggc ctggagccgt  780
tggtag                                                            786

SEQ ID NO: 242       moltype = DNA   length = 786
FEATURE              Location/Qualifiers
misc_feature        1..786
                    note = Synthetic
source              1..786
                    mol_type = other DNA
                    organism = synthetic construct
SEQUENCE: 242
atgaataatg agagtcaggc caaagactcc agtttgcgca tggaacctct ggaaaaagaa   60
aaaggggccg caggtcaggg agcgttatct cagatccccc ctgagtctta ccgtacaaaa  120
tcacccgcag agctgcttgg tgcagggaaa accagagctg acctgaattt tcccgatgtc  180
aaaaacgatt acgaactgga taacgctctg attggccaga cggtaacatc caacggctgt  240
gtggtaaaag caccatgggt tagaaaaagat tttaacactc caggctattg gtcagaggga  300
tatattaaac cttgcgcggc atatctttct tatattaaga aagacaccat tccgtctggc  360
gttcaggaat catattcgct gtcgaaaaaa aaaggtttta cccgtcagtt tacggtgagt  420
gcttccgtga cgagtagtgt tagcgcaggt attttcggat gtgaagcaag cctggaagtt  480
accaccggtt tcagctattc ggaagatatt aacgaagaaa caaccgaaac ctggaccaga  540
acagtagcag gtccgcagga ttactggacc ttccaaccgg ttttactgta tgcatggaag  600
gttaacgcca acgcactgag ctacatgtcc ccgaagccgt cattatacta tactagtggt  660
aaaacaacct atatattttc tccagttttt cgcaattctc cgagtacaat cgacaaagac  720
ataggttatc tgagtctcca gacggtgatt gaatatatgt gtaatgaggc gtggtccaga  780
tggtga                                                            786

SEQ ID NO: 243       moltype = DNA   length = 786
FEATURE              Location/Qualifiers
misc_feature        1..786
                    note = Synthetic
source              1..786
                    mol_type = other DNA
                    organism = synthetic construct
SEQUENCE: 243
atgaataatg agagccaggc caaagactca tcccttcgaa tggaaccgct ggagaaggaa   60
aaaggagcgg cgggacaggg cgccttgtca cagattccac cggaatcata tcggacaaaa  120
tccccggcgg agcttttagg cgccggtaaa acgcgtgcgg acttgaactt cccggacgtg  180
aaaaatgatt acgaactgga taatgccctg ataggacaga cagtaaccag caatggttgc  240
gttgtaaaag ccccatgggt gcgtaaagac tttaatactc ccggttattg gtccgagggc  300
tatatcaaac cgtgtgcagc ctatctgagc tatattaaaa aagatactgt gccttccggt  360
gtgcaggaat cttacagttt gagtaagaag aaaggtttta cccgtcagtt taccacgagc  420
gcttctgtga catcctccgt gagcgccggt atttttggct gtgaagcctc tctggaagtt  480
acaaccggtt ttagttatgg gcaggatata aacgaggaaa caaccgaaac gtggaccgt  540
```

```
accgttgcag ggccgcaaga ttactggacc ttccagccgg ttctgttgta tgcgtggaaa    600
gtgaacgcca acgccctgtc ttatatgtca ccaaaaccgt ccttgtatta tacatccggc    660
aagactactt atatttttag cccagtgttc cgtaacagtc cctcgactat agacaaagac    720
attggatatc tgagcctcca aaccgttatc gagtacatgt gcaatgaggc gtggtcacgg    780
tggtaa                                                               786
```

```
SEQ ID NO: 244           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 244
atgaataacg aaagtcaggc aaaagacagt tctctgcgta tggaaccgct ggagaaagag    60
aaaggcgcag ctggacaagg cgcactgtcc cagataccgc ccgaatcata tcggacaaaa    120
tcgccggcgg aattattagg tgcagggaaa acccgcgctg atcttaactt tccggatgtg    180
aaaaatgact acgagctgga taacgcgctg attggtcaga cggtgacgtc taatggctgt    240
gtggttaaag cgccttgggt gcgcaaagat tttaacacac ctggatattg gagcgaaggg    300
tacatcaaac cgtgcgccgc atacctctcc tacattaaaa aagatacaat accttctggc    360
gtacaggaat cctactctct cagcaaaaag aagggtttta ccagacaatt taccgtgtct    420
gcgtcagtca cttcgagtgt gtcagcgggg attttggct gtgaggccag tttggaagtg     480
actaccgggt tctcatacgg acaagatatc aatgaagaga ccaccgaaac ctggacgcgt    540
actgttgcag gcccacagga ctattggact tttcagcccg tgctcctgta tgcctggaag    600
gtgaacgcga acgctttatc ctatatgtcc ccgaaaccct ccctgtacta cacctctggt    660
aaaactactt acatattctc gccagtgttt cgcaactctc cttcgaccat tgacaaggat    720
ataggctact taagtcttca aaccgtgatt gaatatatgt gcaatgaagc ctggagtcgc    780
tggtaa                                                               786
```

```
SEQ ID NO: 245           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 245
atgaataatg agtcccaggc gaaagattct tcattgcgta tggaacccct ggagaaagag    60
aagggggccg cgggtcaggg ggcgctgtcc cagattccac cggagagcta tcggaccaag    120
agcccggctg agcttttggg tgccggtaaa acccgtgctg atttaaattt tcctgatgtt    180
aaaaacgatt atgagttgga caatgcttta attgggcaga ctgtgacctc gaacggatgc    240
gttgtgaagg ccccatgggt acggaaagac tttaacacgc ccggctattg gtcagaggga    300
tatataaac catgtgccgc gtacttatca tatattaaaa aagacacagt tccatcggcc    360
acctcgattg aacacacact gacaaaaaaa aaaggattta cgtcccagtt tactgcctcc    420
accgaggtaa aggtgggcgt ctccgcgggg atatttggct gcgaaaccag tctggaagtg    480
accaccggat tctcttatag tgaaactata aatgaagaga ctaccgagac ctggaagaaa    540
acagtggcag gtccgcagga ctattggacg tttcaacctg ttttgttgta tgcgtggaaa    600
gtgaacgcga atgcgttgtc ctatatgtcc ccaaagcctt ctttatacta cacgtcagga    660
aaaacgacgt acatattttc tcctgttttc cgcaactcgc cctcaaccat cgacaaggat    720
ataggctatt tatcgctcca gaccgtcatt gaatatatgt gtaacgaggc ctggtctcgc    780
tggtaa                                                               786
```

```
SEQ ID NO: 246           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 246
atgaataatg aaagccaagc taaagatagt tcgttacgca tggaacctct ggaaaaggaa    60
aaaggcgctg caggtcaagg cgcgctttcc cagatccccc ctgagtcata tcgtactaaa    120
agtccagccg aactgctggg cgcgggtaaa actcgagccg atttgaattt tccggatgta    180
aaaaatgatt atgaattaga caatgctctg atcggacaga ctgttacctc taatggttgt    240
gtagttaaag cgccctgggt ccgcaaagac tttaacaccc ctggttactg gagtgaaggt    300
tatataaaac cgtgtgccgc ctatctgtca tatattaaaa aggatacggt accgtccggt    360
acatcaatag agcatacgct gacgaagaag aaaggtttca cctcccagtt tacagcgtcc    420
gcggaggtca aagtgggagt ttcagcaggc atctttgggt gcgaagcaag tctggaagtc    480
acaacaggat ttagttatgg tcaagatata aatgaagaga cgactgagac atggaaaaaa    540
acggtggccg ggccgcagga ttattggacg ttccaaccag tactcttgta cgcatggaaa    600
gtaaacgcat acgcgttatc atatatgtcg ccgaaaccat cctatatta cacatcgggc    660
aaaaccacat atattttttc cccggtgttc cgtaatagtc cttccaccat tgataaagat    720
attgggtacc tctccctgca gactgtaatt gagtatatgt gtaatgaggc atggtcgcgc    780
tggtga                                                               786
```

```
SEQ ID NO: 247           moltype = DNA   length = 786
FEATURE                  Location/Qualifiers
misc_feature             1..786
                         note = Synthetic
```

-continued

```
source                1..786
                      mol_type = other DNA
                      organism = synthetic construct
SEQUENCE: 247
atgaacaatg agagtcaggc caaagattcg tcacttagaa tggagccact tgaaaaggaa   60
aagggggccg ctggtcaggg agcactgtcg cagattcccc cggaatctta tcgcaccaaa   120
tctccggcgg aacttctggg cgcaggaaaa actcgagccg atctgaattt tcccgatgtg   180
aaaaacgatt atgaacttga taacgcgctg attggtcaga ctgttacgag caacggatgt   240
gttgtgaaag ccccatgggt gcgcaaagac tttaataccc cgggctactg gtctgagggt   300
tacattaaac catgtgccgc atatctgtcc tacataaaaa aggatacagt accgtctgta   360
acatcgattg aacatacatt aacaaaaaaa aagggattta cgtcccagtt tacggcgtcc   420
gctgaagtta aagttggcgc gagcgcaggg gtatttgcct gcgaagcgtc cctcgaagtg   480
acaactggct tctcttacgg ccaggatatt aacgaggaaa cgacggagac ctggaagaag   540
acagtcgccg gtcctcagga ctattggact tttcagcccg ttcttttgta cgcgtggaaa   600
gtgaatgcta atgccttatc atacatgtcc ccgaaaccgt ctctttatta cacctcgggg   660
aaaacgacat acattttttc tccggtgttc cgcaactccc catcaacaat cgacaaagat   720
attggttacc tgtcattgca gactgtaatt gaatatatgt gcaacgaagc atggtcacgc   780
tggtga                                                              786

SEQ ID NO: 248         moltype = DNA  length = 786
FEATURE                Location/Qualifiers
misc_feature          1..786
                      note = Synthetic
source                1..786
                      mol_type = other DNA
                      organism = synthetic construct
SEQUENCE: 248
atgaataacg agagccaggc gaaagattca agcctgcgta tggaacccct ggaaaaagaa   60
aaaggagccg caggtcaggg agcactgagt cagataccgc cagagtcgta tcgaacaaaa   120
tctccagcag aacttttagg cgctggaaag actagagccg atctcaattt tcctgatgtg   180
aagaatgact atgaactgga taacgccctg attggccaaa cggtgacaag caatggatgc   240
gttgtgaaag cccctggt gcgaaaagat tttaataccc caggatactg gagcgaggga   300
tacatataaac cgtgcgcggc atacttatcc tatattaaaa aggacaccat tccgtctgtg   360
acggtatcg aacatacctt gacaaaaaag aaagggttca ccagccagtt taccgtctcg   420
gcagaggtga aggcaggcgc ctcggctggc gtgtttgctt gtgaagccag tctggaagtt   480
acaaccggtt ttagctacgg tcaagatatc aacgaagaaa caacggagac ttggaaaaaa   540
accgttgccg gcccgcagga ttattggacc tttcaaccgg tcctgctgta tgcgtggaag   600
gttaacgcga atgcactctc ttatatgtca ccgaaaccgt ccctgtatta tacgagcgga   660
aaaaccactt acatattctc gcccgtcttc cgtaactcgc cgtctactat tgataaggat   720
atcggatatc ttagcctgca gactgtgata gagtacatgt gcaacgaagc atggtcgcgt   780
tggtga                                                              786

SEQ ID NO: 249         moltype = DNA  length = 786
FEATURE                Location/Qualifiers
misc_feature          1..786
                      note = Synthetic
source                1..786
                      mol_type = other DNA
                      organism = synthetic construct
SEQUENCE: 249
atgaacaacg aaagtcaagc aaaagattct tctctccgca tggagccact ggagaaagaa   60
aaaggagccg ctggtcaagg cgccctctcg cagataccac cggaatccta tcgtacaaag   120
tccccagccg agttactggg tgctggaaaa acccgtgccg atttgaattt cccggacgtc   180
aaaaacgatt acgaactgga taacgctctg attggtcaaa cagttaccag taatggttgt   240
gtggtaaaag cccccttggg gcgtaaagac tttaacaccc cgggctattg gtcagagggc   300
tatattaagc cctgcgcgctg catatcttagc tacattaaaa aggatacaat accatcgggt   360
actagcgagg aacacaccct gaccaagaaa aaggggttta cgtcccagtt cacagtgtcc   420
gcagaggtaa aagctggtgc atctgcaggt gtcttcgctt gtgaagcgag tctggaagta   480
accactggct tctcttacgg tcaagatatt aatgaagaaa cggaagaaac ttggaaaaag   540
actgttgcag gtccacagga ttattggacc ttccaaccgg tcctgctgta tgcttggaag   600
gtcaatgcga acgctttgtc ttatatgagt cctaaaccga gtctgtatta tacgtcaggt   660
aaaaccacct acatatttag tcctgttttt cggaactcgc cgtcaacaat tgataaggat   720
attggttatc tgagtttgca aaccgttatc gaatatatgt gcaatgaggc ttggagccgt   780
tggtga                                                              786

SEQ ID NO: 250         moltype = DNA  length = 786
FEATURE                Location/Qualifiers
misc_feature          1..786
                      note = Synthetic
source                1..786
                      mol_type = other DNA
                      organism = synthetic construct
SEQUENCE: 250
atgaataacg aaagccaggc aaaagattcc tccttacgca tggaacccct cgaaaaggaa   60
aaaggtgcgg caggtcaggg tgccctgagt caaattcctc ctgaaagcta tcgtactaaa   120
tcacccgctg agctcttagg tgctggcaag actcgtgctg acctgaattt tccggatgtt   180
aaaaacgatt acgagctgga caatgcgctg attggtcaaa ccgttacatc gaatggatgt   240
gttgtgaaag ccccgtgggt acgtaaggac tttaacacac cgggctattg gtcagagggc   300
tatattaagc cctgcgcggc gtatttaagt tatattaaaa aagacaccat ccctagtggc   360
```

```
acttctgaag agcacacgtt aaccaaaaag aagggctttt cgcgacagtt tacagtttcg   420
gccgaagtga aggctggcgc cagtgcaggt gtcttcgcct gcgaaacctc gctggaggtg   480
acgaccggtt tcagctacgg gcaggatatt aacgaggaaa cagaggagac cgataccaag   540
accgtgacgg ggccacagga ttattggaca ttccaacctg tgttattata cgcgtggaaa   600
gtgaatgcca atgctctgtc ctatatgagt cccaaaccgt ctttgtatta tacctcaggg   660
aaaaccacgt atattttctc acctgtgttc cgcaactcac catccaccat tgataaggat   720
attggttacc tgtcattaca aacggtaatc gagtacatgt gcaatgaagc atggtcacgc   780
tggtga                                                             786
```

```
SEQ ID NO: 251          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 251
atgaacaatg aaagccaagc aaaggactcc agtttgcgca tggaacccct cgaaaaagaa   60
aagggcgccg ccggtcaggg ggctttatca cagatccccc cggaatccta tagaactaag   120
tctccggctg aattgttagg ggcgggcaaa actcgcgcag atctgaactt tccggacgtc   180
aaaaatgatt atgaacttga caatgccctg ataggccaga cggttacgtc taatggatgc   240
gttgtgaagg cgccctgggt acggaaagat tttaacacac ccggctactg gtctgagggt   300
tatatcaaac cgtgcgcagc atacctctcg tatataaaaa aagacacgat accctcgggc   360
acaagtattg aatatagtct gacgaagaaa aaggggtttt cacgacagtt caccgtatca   420
gcggaggtta aagttggggt tagcgccggg atctttggat gcgaaacgtc acttgaggtt   480
actacaggtt ttagctactc cgaggatatc aatgaagaaa ccaccgaaac cgacacaaag   540
acattagcgg gcccgcaaga ttattggacg tttcagccag tcctgcttta tgcttggaaa   600
gtgaatgcca atgcgctgag ctatatgtcg cccaaaccat ctctgtatta tacctcgggg   660
aaaacgacct acatttttc tccagtattt agaaatagcc caagtacgat tgacaaagat   720
attggatacc tgagtctgca aactgttatc gaatatatgt gtaacgaggc gtggtcgcgc   780
tggtaa                                                             786
```

```
SEQ ID NO: 252          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 252
atgaacaatg aatcacaggc gaaagattct tcactgagaa tggaacccct ggagaaggaa   60
aaaggggctg ccggtcaggg ggcgctgtca cagatacccc ctgaaagtta ccgtacgaag   120
tctcccgcgg aattactggg tgcgggcaaa actagagccg atcttaattt ccccgatgtg   180
aagaacgact atgaactgga caacgctctg atcggtcaaa ccgttacttc caatgggtgc   240
gtagttaaag cgccctgggt ccgtaaagac ttcaatacac cgggttactg gagcgaagga   300
tacattaagc cgtgcgcggc gtaccttagt tacattaaga aagacactat tccatcagga   360
acttcaatag agtattctct gacgaaaaaa aaaggatttt cacgccaatt taccgttagt   420
gcggaggtga aggttggaat atcggctggt gtttttggat gtgaaacgtc cttagaggtc   480
accaccggtt tcagttattc tgaagacatt aacgaggaga caacagagac cgataccaaa   540
acgctggcgg gaccgcaaga ttattggact tttcagccag tacttttata tgcatggaaa   600
gtaaatgcca atgcactgtc atacatgagc caaaaccat ccctgtatta tacctcgggc   660
aaaactactt acatctttc tccggttttt cgtaactcac cttccacgat agataaggat   720
attggttatc tgtcgttaca gacggtcata gaatacatgt gtaacgaggc gtggagtaga   780
tggtga                                                             786
```

```
SEQ ID NO: 253          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 253
atgaacaatg aatcgcaggc taaagatagt tccctccgca tggagccgtt agaaaaagaa   60
aagggtgccg ccggtcaggg cgcactgtct cagattccgc ctgagtcgta ccgtactaaa   120
agccccgcag aactgctcgg tgcaggcaag actcgcgctg atctgaattt ccctgacgtg   180
aaaaatgatt atgaattaga caatgctctg attggtcaaa ctgtcacgag taacggctgt   240
gtcgtaaaag ccccttgggt cagaaaagat ttcaacacac cggggtattg gtcggaaggt   300
tatataaaac catgcgcagc ctatttgagc tacatcaaaa aagacaccat cccacagaat   360
gtaactacga ccttaagtta tcaaaaaact aaaggacaca cccgtcagtt tacaacatca   420
gtaaatgcta agtacagcgt cggcgccaac atcgatatag taaatgttgg tagcgaaatc   480
acgaccggct tcacgcgaag cgagtcatgg tcaacgacgc agagcttcac cgataccaag   540
gagatgaagg ggccgcaaga ctactggact tttcaacccg tgttgttata tgcttggaag   600
gtcaatgcga atgcgctcag ctatatgtct ccgaagccta gtctgtacta tacaagcggc   660
aaaaccacat atattttctc cccggtgttt cggaatagcc catcaacaat tgataaggac   720
attggatatc tgtcattgca gacagtgatt gagtatatgt gcaatgaagc ctggagccgt   780
tggtga                                                             786
```

```
SEQ ID NO: 254          moltype = DNA   length = 786
```

```
FEATURE              Location/Qualifiers
misc_feature         1..786
                     note = Synthetic
source               1..786
                     mol_type = other DNA
                     organism = synthetic construct
SEQUENCE: 254
atgaataatg agagtcaagc aaaagatagt tcattgcgaa tggaaccatt agaaaaagaa   60
aaaggcgcag ctgggcaagg tgccctgtct caaattcctc cagagagcta ccgcacgaaa  120
tccccagccg agttgctggg cgccgggaaa acccgtgcgg atttgaactt tcccgatgtt  180
aaaaatgatt atgagcttga taatgcgctt atcggtcaga ctgttactag caacggttgc  240
gttgtaaaag ctccgtgggt gcgtaaagat tttaataccc cgggctattg gagcgagggt  300
tatattaaac cttgtgccgc ttatttatca tatattaaaa aagatacgat ccctaaccaa  360
gttgatcttc agcaccaggt gacgaagaaa tctggtctga cctcccaatt caccacagag  420
gtgaaatcta gctattcagt gggtgcaaaa atcgacatag tgaatgtggg atccgagatc  480
acgcacaggat tctctcaaac tcagtcatgg agtcaagaga gagatgaatc ctggacaaag  540
acattgcacg gccctcagga ttactggacg tttcagccgg ttttgctgta tgcctggaaa  600
gttaatgcga atgccttaag ttatatgtca ccaaagccat cactttatta cacatcagga  660
aaaacgacct atattttttc cccagtgttc cgtaattcac cttccacaat tgacaaagat  720
attgggtatc tgtcactcca gaccgttata gaatacatgt gtaatgaggc gtggtcccgg  780
tggtaa                                                             786

SEQ ID NO: 255        moltype = DNA   length = 786
FEATURE              Location/Qualifiers
misc_feature         1..786
                     note = Synthetic
source               1..786
                     mol_type = other DNA
                     organism = synthetic construct
SEQUENCE: 255
atgaataatg aatcacaagc taaggattcc agcctccgga tggaacccct ggagaaagag   60
aaaggggcgg caggtcaggg cgcgcttagc cagattcctc ccgagtcata tagaaccaaa  120
tctcccgccg agctgcttgg tgcaggcaag acccgtgcgg atctgaattt tcctgatgta  180
aaaaatgact atgaactcga caacgcctta atcggacaaa cagtaacttc caacggatgc  240
gtggttaaag caccctgggt gcgcaaagat tttaacactc cgggttattg gagtgaagga  300
tacataaaac cttgcgcggc ctacctgagc tatatcaaaa aagatacctta tcccagcggt  360
gccacgcagc attacactac gactaagact gtgggcctga ccgagcagtt tacgaaagaa  420
gtgaaagcga gctattccgt cggtgccaat attgacattg ttaatgttgg tagcgaaatt  480
acgactggat tctcacgctc aagttcctgg agccaacaaa caattcagag ctggacgaaa  540
acattgcaag ggccacaaga ctactggact ttccaacctg tactgctgta tgcctggaaa  600
gtgaatgcca atgctctcag ctatatgagc ccaaagccta gtctgtacta cacatcgggt  660
aagaccacct atatttttag tcctgtattt cgcaattcac cgtcgacaat tgataaagat  720
attggttatc ttagcttaca aacggtgatc gaatacatgt gtaacgaagc atggtcccgt  780
tggtga                                                             786

SEQ ID NO: 256        moltype = DNA   length = 777
FEATURE              Location/Qualifiers
misc_feature         1..777
                     note = Synthetic
source               1..777
                     mol_type = other DNA
                     organism = synthetic construct
SEQUENCE: 256
atgaataacg aaagtcaggc aaaagatagt tccctgagaa tggaacccct cgaaaaagaa   60
aaaggggcgg caggccaggg ggctctttcc cagattccgc ccgagtcgta tcgcactaaa  120
tctcctgcgg aacttcttgg tgcggggaaa acccgagccg atcttaactt tcccgacgtc  180
aaaaatgact atgaactcga caacgcgctt attggtcaaa cggttacatc aaatggctgt  240
gtggttaaag ctccatgggt tcgcaaggat ttcaataccc cgggatattg gagtgagggt  300
tacataaaac cgtgcgcagc atatttatcc tatataaaaa aagatacaat acctggtgac  360
gaaactcata ccttccggaa atttaaaggc tttactactc agtttacgac cagtatttca  420
ataacagccg gtgtttcagg gggtgtcttt ggatgcaatg catctttgga agtaaccacg  480
gaattctctt atggacaaga aataacgaaa caaacggagg aaacttggac gaagacgatt  540
tatgcacaag attattggac gttccagccc gtactgttat acgcttggaa ggtaacgcg  600
aatgctctgt cttatatgtc tccaaagccg tctctgtatt ataccagtgg taaaaccact  660
tatatttta gtccggtttt tagaaattct ccgagcacta tcgataagga tattggctac  720
ttatcactgc agacagtcat tgagtatatg tgtaatgagg cttggagtcg ttggtga      777

SEQ ID NO: 257        moltype = DNA   length = 783
FEATURE              Location/Qualifiers
misc_feature         1..783
                     note = Synthetic
source               1..783
                     mol_type = other DNA
                     organism = synthetic construct
SEQUENCE: 257
atgaataatg agagtcaagc taaagacagt tccctgcgca tggaaccgct ggaaaaagaa   60
aaaggggccg ctgccagggt gcactgtcg cagattccac cagaatcata ccgcacaaaa  120
tctccggcag aactgctggg tgccggtaag acgcgcgcgg atctgaattt cccggacgtg  180
aaaaacgatt atgaacttga taatgcactg atcggacaga ccgttacctc aaatgggtgc  240
```

-continued

```
gttgtgaaag ctccttgggt ccgtaaggat ttcaataccc ctggctattg gagcgaggt      300
tacattaaac cgtgcgccgc ttatctgtct tatataaaga aagacacggt tcccgggact      360
atggagaaaa cgttagaaaa aaaaaacggt tacagtagtc agtttacaac tagtgtggag      420
atcaaggcag gcttgtcagc cggcatcttt ggatgtaatg cctctttgga agtaacgact      480
gggttcacgt atgaacagac tatcactagc gaaacaacgg agacttggaa aaaaacactg      540
acgtccggtc cccaggatta ttggacgttt caaccggttt tattgtatgc atggaaagta      600
aatgcaaatg ctctctcgta tatgtctccg aagccttctc tgtattacac cagcggcaaa      660
accacatata tcttctcacc tgtttttccgc aactctcctt ccaccatcga caaagatata      720
ggctatttat cgctgcagac cgttattgag tatatgtgca atgaagcctg gtcacgctgg      780
tga                                                                    783

SEQ ID NO: 258           moltype = DNA   length = 777
FEATURE                  Location/Qualifiers
misc_feature             1..777
                         note = Synthetic
source                   1..777
                         mol_type = other DNA
                         organism = synthetic construct
SEQUENCE: 258
atgaataacg agtcccaagc caaagatagt tcacttcgca tggaaccgtt ggaaaaagaa      60
aaaggggcag ccgggcaggg cgccttaagt cagattcctc cggagtcata tcgtactaag     120
agcccagctg aactccttgg tgcgggaaaa actcgtcgag acctgaattt tccggacgta     180
aagaacgatt acgaacttga taacgcactt atcggccaga cagtgacatc taacggttgc     240
gttgtcaaag cgccttgggt tcgcaaggat tttaatacgc cgggctattg gagtgaaggc     300
tatatcaagc cttgtgcagc atatctcagc tatataaaaa aagatacct cgcggggacc      360
gaggacgaca cgctgcgtaa attcaaggca tatacttctc agtttacagc tagcgttgaa     420
gtgaaagcct ccgcctctgc aggaatattt ggttgcgaag cgagtttgga agtgactact     480
ggcttttcct atggagaaga aataaccgaa gaaaaagagg agacatggaa gaaaacggtg     540
gctccgcagg actactggac gttccaacct gttctccttt atgcttggaa ggttaatgcc     600
aatgcactga gctatatgtc tcctaaaccg agcttatact atacatcagg aaaaaccacg     660
tacatcttttt ctccggtatt tagaaactcg ccaagcacta ttgacaaaga cataggatat     720
ctgagtttac agactgtgat agagtatatg tgcaatgagg cctggagcag atggtga       777

SEQ ID NO: 259           moltype = DNA   length = 777
FEATURE                  Location/Qualifiers
misc_feature             1..777
                         note = Synthetic
source                   1..777
                         mol_type = other DNA
                         organism = synthetic construct
SEQUENCE: 259
atgaataacg agtcacaggc caaagacagc tcgttacgga tggaacctct ggagaaagaa      60
aaaggtgcag ccggtcaggg tgcattgtca cagataccgc cagaatcata tagaacaaaa     120
agtcctgccg aattgctggg agctggcaag acccgtgctg acctcaattt tccggacgta     180
aaaaatgatt atgaattaga taatgcgttg atcggcacga cggttacatc gaatgggtgc      240
gttgtcaaag ccccatgggt ccggaaagat tttaacacgc cgggttattg gagtgaaggg     300
tatataaaac catgcgcggc ctatttatcc tatattaaaa aagatactt aagtgggaca      360
tccgaacata ctttacgcaa attaaaagga tacaccagtc gcttcaccgt ctctgcggaa     420
ttgaaagcag ggatcaaggc gggaatcttc ggttgcgaag caagcttaga agttactacc     480
gggtttagct atggcgagga tataagtcaa gaaacggaag agacgtggaa aaagacagtt     540
gcaccgcagg attattggac atttcaaccg gtttttactgt agcatggaa agtaaatgcc     600
aacgcattga gctatatgag ccctaagcca tcccttttatt atactagtgg taagaccacc     660
tatatttttt cacccgtgtt cagaaattct ccctccacaa tcgataaaga cattggttat     720
ctgtcattac agacagttat cgagtacatg tgtaatgaag cctggagtcg ttggtga       777

SEQ ID NO: 260           moltype = DNA   length = 786
FEATURE                  Location/Qualifiers
misc_feature             1..786
                         note = Synthetic
source                   1..786
                         mol_type = other DNA
                         organism = synthetic construct
SEQUENCE: 260
atgaacaacg aatcccaggc gaaagatagc tcactgcgca tggagcctct ggaaaaagaa      60
aaaggtgcag cagggcaagg tgcactgtcc caaatccctc cggagtcata tcgcacaaag     120
tcacctgcgg agctgctcgg tgccgggaaa acacgcgcag atttaaactt tcctgatgtt     180
aaaaatgact atgaactgga caacgccctg atcggacaga ccgtaacctc taatggatgc     240
gttgtcaaag caccgtgggt ccgcaaggat tttaatacgc caggatattg gagtgagggc     300
tatattaaac cttgcgcagc ctacttatct tacattaaaa aagacactat ccctcagaat     360
gcaactcagc attatacaac aacaaaaaccc gttggcctga ctgaacagtt tacgaaagag     420
gtgaaagcgt catacagtgt aggcgcgaat attgatattg tgaatgtggg cagcgaaata     480
accacaggct ttagtcgtag ctcctcttgg tctcaacaga cgattcagtc gtggactaaa     540
actttgcaag gtcctcaaga ttactggaca tttcaacccg ttcttctgta tgcctggaaa     600
gtgaatgcca acgctctgtc atatatgtcg cctaagccgt ctttatacta tacctcgggc     660
aaaactacat atatttttc ccccgttttt cgcaatagtc cgagtacgat cgataaagat     720
atcggctatc ttagtcttca aactgtgata gaatacatgt gtaatgaggc ttggtcccgc     780
tggtga                                                                 786

SEQ ID NO: 261           moltype = DNA   length = 786
```

-continued

```
FEATURE               Location/Qualifiers
misc_feature          1..786
                      note = Synthetic
source                1..786
                      mol_type = other DNA
                      organism = synthetic construct
SEQUENCE: 261
atgaacaatg aatcacaggc taaggactcc agtttacgta tggaaccact ggagaaagag   60
aaaggtgctg cgggtcaggg tgccctgtcg cagatccccc ctgagagtta cagaaccaaa  120
tcccccgcag aactcttggg ggctggtaaa acgcgggccg acctgaattt cccggacgtg  180
aaaaacgatt acgagcttga taacgcctta attggacaga ctgtgacgtc aaacggttgt  240
gttgtgaaag caccgtgggt tagaaaggat ttcaatacgc ccggttactg gagtgaaggt  300
tacataaagc cttgcgcagc ttatctctcc tacatcaaaa aagatactat acccgatgga  360
accagctctt ctcatacctt cgagaaaaaa aaagggtata gttcccagac caccgtgtct  420
acagaagtga aggcaagcgt gggcgttaat attctggggt gtgacgctag catggaagtg  480
accactgggt tcacgtatac tcagggcata tcgtctgaaa ccacggagtc ctggaccaaa  540
acggtaactg gacctcagga ctactggact ttccagcctg tactgttata cgcatggaaa  600
gtcaatgcca acgccttgtc gtacatgagc cctaagccat ccctttatta tacctccgga  660
aaaactacat atatctttag tccagtgttt agaaattcgc cctccactat cgacaaaagat  720
atcggatatt tgtctctgca gactgtgatt gagtatatgt gtaacgaggc atggtcacgg  780
tggtaa                                                             786

SEQ ID NO: 262       moltype = DNA  length = 777
FEATURE               Location/Qualifiers
misc_feature          1..777
                      note = Synthetic
source                1..777
                      mol_type = other DNA
                      organism = synthetic construct
SEQUENCE: 262
atgaacaatg agagtcaggc gaaagacagt tctttacgta tggaaccttt ggagaaggaa   60
aagggtgctg caggccaggg tgcgctgtct cagattccgc cggaatcgta ccgtactaaa  120
agtcccgcag agcttctcgg ggcaggcaag acgcgtgctg acctgaattt tcctgatgtt  180
aaaaacgatt acgagctcga taacgcactg attggtcaga cagttacctc caatgggtgc  240
gtggtgaaag cgccatgggt tcgtaaagac tttaatacac cgggttattg gagtgaaggg  300
tatattaaac cctgtgccgc atatctttcg tatattaaaa aagatacgtt atcaggtact  360
gaagaacata cgttacgcaa atttaaagga tatacatctc agttcactgc gtcagtcgaa  420
gtgaaagcat ccgccagtgc tggcattttt ggctgtgaaa cgtctcttga agtaacgaca  480
ggcttttcct atggacaaga aatcaccgac gaaaaagaag agacatggaa aaaaaccgta  540
gcaccgcaag attactggac cttttcagccc gtgttacttt atgcatggaa agttaacgca  600
aacgcgctgt cctatatgag cccgaaacct agtctgtatt acactagcgg gaaaactaca  660
tacatattct cccctgtctt tcgtaattcc ccgtcgacta tagacaaaga tatcggctat  720
ttatctctcc aaacggtaat agagtatatg tgtaacgaag cttggtctcg atggtaa     777

SEQ ID NO: 263       moltype = DNA  length = 786
FEATURE               Location/Qualifiers
misc_feature          1..786
                      note = Synthetic
source                1..786
                      mol_type = other DNA
                      organism = synthetic construct
SEQUENCE: 263
atgaataatg aaagtcaggc gaaagacagc agtcttcgga tggagccgct ggagaaagaa   60
aaaggtgctg caggtcaagg agcgctttca cagattccac ctgagtccta tcgaacgaaa  120
tcgccggcgg aattactggg tgcaggcaaa acgcggggcg accttaattt ccctgacgtc  180
aaaaatgact atgaactcga taatgctttg atcggacaga cagttacgtc caatggctgc  240
gtggtcaaag cgccctgggt gcgcaaagac ttcaacactc caggatactg gtctgagggt  300
tatatcaagc cctgtgcggc ctatttaagc tatataaaaa aggacacaat cccacaacag  360
gttacacaga cccgttcata tcaaaaaact aaaggtcaca cgcagcaatt cacaacaagt  420
gtatctgcaa agtactccgt aggagcgaaa atcgacattg ttaatatcgg atcagaaatt  480
acaacaggct ttagtcagac cgaatcgtgg tctactaccc agacttttac tgaaagcaag  540
caactcacag gcccgcagga ttattggaca tttcagccag tattgttata tgcgtggaaa  600
gttaatgcta atgctttgag ttatatgtcg cctaaaccta gtctgtacta cacgtcgggt  660
aaaacaactt atatttttc cccggttttc cggaattctc cgtcgaccat tgataaagat  720
atcggatatc tgtcactgca gactgtgatt gaatatatgt gtaatgaagc ctggagtcgc  780
tggtaa                                                             786

SEQ ID NO: 264       moltype = DNA  length = 777
FEATURE               Location/Qualifiers
misc_feature          1..777
                      note = Synthetic
source                1..777
                      mol_type = other DNA
                      organism = synthetic construct
SEQUENCE: 264
atgaataacg agagccaggc caaagactcc agcctgcgca tggagccgct ggaaaaagaa   60
aaaggggctg cgggtcaggg agcactgtct cagattccgc cagaatcgta ccgcacgaag  120
agcccggcag aacttctggg ggctggaaaa acacgtgcgg acttgaattt tccggacgtt  180
aagaatgact atgagctgga taatgcctta attggtcaaa ctgttaccag taatggctgt  240
```

```
gttgttaagg ctccgtgggt tcgtaaggat tttaacaccc ccggctactg gtcggaaggc   300
tacataaaac cgtgcgcagc ttatctgtca tatataaaaa aggatacact ggccgggaca   360
tcagaacata cactgcggaa actgcgcggt tatactagcc agttcaacgt tagtgcagaa   420
gttaaagctg gggtaaaagg cggcattttg ggttgcgaag catcattgga agttactacg   480
ggttttagct atggacagga aataacccag gaggcagaag agaccggaaa aaagaccgta   540
agcccacaag attattggac gtttcagccg gttttgttat atgcatggaa agtaaacgcg   600
aatgcactta gttacatgag tccgaaacct tcactttatt acacgtcagg caagacgacc   660
tacatttttca gccctgtttt ccggaactca ccgtcaacta ttgataagga cataggatat   720
ctgtctctcc aaacggtaat cgaatatatg tgcaatgagg catggagcag atggtga      777
```

```
SEQ ID NO: 265          moltype = DNA   length = 777
FEATURE                 Location/Qualifiers
misc_feature            1..777
                        note = Synthetic
source                  1..777
                        mol_type = other DNA
                        organism = synthetic construct
SEQUENCE: 265
atgaataatg aatcgcaagc aaaagatagc tcactgcgca tggagccatt ggagaaagaa   60
aaaggtgcag ccggccaagg tgcattgagt cagataccgc cggaatccta ccgaacaaaa   120
agtcctgccg agcttttggg cgcaggtaaa acgcgggcag atttgaattt tcccgacgtg   180
aagaatgact atgaactgga caatgcactt atcggtcagtc cggttacgtc taatggctgt   240
gttgttaaag cgccgtgggt gcgcaaagat tttaatacac ctgggtactg gagcgagggc   300
tatattaaac cgtgtgcagc atatttaagc tatattaaaa aagacactgt agtgggcact   360
gttgagcaga cgatggaaaa gaaaaaaggc tttacaagtc agtttacagc tagcacggaa   420
ataaaagcct ctgcgtccgc cggctttttc ggctgtgaag cttcattgga agttacgacg   480
ggcttcgaat atgaagagac tgtcacatct gagacaaccc acacgtggaa aaaaacactt   540
acagaacagg attattggac attccaacca gtactgctct atgcgtggaa ggttaatgca   600
aatgctcttt catatatgtc gcccaaacct agtctgtatt atactagtgg caagaccaca   660
tatattttta gtcccgtctt ccgcaattcc ccttcaacca ttgacaaaga tattggatac   720
ctgtcactgc aaacggtgat cgaatatatg tgtaacgaag catggagcag atggtaa      777
```

```
SEQ ID NO: 266          moltype = DNA   length = 774
FEATURE                 Location/Qualifiers
misc_feature            1..774
                        note = Synthetic
source                  1..774
                        mol_type = other DNA
                        organism = synthetic construct
SEQUENCE: 266
atgaataatg aaagtcaggc aaaagatagt agcttacgga tggaacccct ggaaaaagag   60
aaaggtgcag ccggtcaggg tgcgttatca cagataccgc cggaatcgta ccgtactaag   120
agcccgcggg agttgttagg ggctggcaaa acgcgcgcaa acctgaactt tccggatgta   180
aaaaacgatt atgaattaga caatgccctg attggtcaga ctgttacttc taatggctgc   240
gtagttaaag ccccgtgggt gcgcaaggat tttaataccc cgggctactg gtcagaaggt   300
tatattaaac cttgtgccgc ttatctttcg tatataaaga aagatacatt gggtactgaa   360
gagcataccc tgcggaagtt caaaggtttt acatcacagt ttacccgtc gatggaagtg   420
aaagcagggg ttaaggctgg aatttttggg tgtgaggctt cgctggaggt cacgacagga   480
tattcctatg gcgaagacat tacggaagag aaggaagaaa tctggaagaa gaccgtttcc   540
cctcaagatt attggacctt tcaacctgta ctgttgtacg cttggaaagt gaatgcgaat   600
gcgctgagtt atatgtcccc gaaaccatct ctgtattata ctagtgggaa aacgacttat   660
attttagtc cgttttcg caactcacca tctaccattg acaaagacat aggttatctt   720
tccctgcaga ccgtgatcga atatatgtgt aacgaggcat ggtcccgatg gtga         774
```

```
SEQ ID NO: 267          moltype = DNA   length = 780
FEATURE                 Location/Qualifiers
misc_feature            1..780
                        note = Synthetic
source                  1..780
                        mol_type = other DNA
                        organism = synthetic construct
SEQUENCE: 267
atgaacaacg aaagtcaagc caaagattct tctctgcgta tggaaccttt ggaaaaagaa   60
aaaggtgcag cagggcaggg tgccttatca cagattccgc ccgagagtta tagaacgaag   120
agccctgcag aacttctggg tgcaggtaaa acgcgggcag atcttaattt cccagacgtt   180
aagaatgatt acgagctgga taatgcgctc attgggcaga cagttactag taatggatgc   240
gtggtaaaag ccccttgggt gcgtaaagat tttaacactc caggctactg gtctgaaggc   300
tatattaaac cctgtgcagc atacttatcc tatataaaaa aagatactgt cgttggcacg   360
caggaacatg agttaactaa aaaaaaagga tatagcacgc agtttacggc gagtacatct   420
ttaaaaagct ctatctctgg tgggattggc gagtgcgaag catcgtttga agttacgacg   480
gagttctcgt actcccagaa ctcttatgaa gaaaaaagcg aaacatggac caagacccttt   540
accggtcccc aggactactg gacctttcag cctgtgctcc tgtacgcgtg gaaggtgaat   600
gccaatgcgt atcctatat gtcacccaag ccgagtttgt attatacttc tggcaaaact   660
acttacattt tttcaccggt ctttcgaaat tcccccttcaa ctattgacaa agacattgga   720
tacttatcat tacaaacggt tattgaatat atgtgtaatg aagcttggtc acgctggtaa   780
```

```
SEQ ID NO: 268          moltype = DNA   length = 804
FEATURE                 Location/Qualifiers
misc_feature            1..804
```

```
                            note = Synthetic
source                      1..804
                            mol_type = other DNA
                            organism = synthetic construct
SEQUENCE: 268
atgaacaatg aatcacaagc caaagacagt agcctccgca tggagcctct ggagaaagag    60
aaaggtgccg caggtcaggg cgctttatca cagatccccc cggaaagtta cagaacgaag   120
agtccggcag aattacttgg tgcgggtaaa acacgtgcgg atttaaattt cccagatgtg   180
aagaacgatt atgagttaga caacgctctg atcggacaga ctgtgacatc gaatggctgc   240
gtggtcaagg caccatgggg acgtaaagac tttaatacac cgggctattg gtccgaaggt   300
tacataaagc cctgtgcggc gtatctgtcg tatatcaaga aagatacctt agacgtggcc   360
gatacggtag gccaggttct gaacaaacgt aaaggtttct caaatcagtt taccgcatct   420
aaagcactga aagcattaat cagtgagggt gttgcaggct gcgacagctg ccacgaagtt   480
acgactaaat tcgattacat cctggaaacc attaaagacg agtcgaaaca gccttttagt   540
aaacccgttt cagttgttcc ttctcagctg tgtcaggact attggacctt tcagcctgtc   600
ctgttgtacg catggaaagt taacgccaat gcgctgagtt atatgagccc taaaccgtct   660
ctgtattaca catcaggcaa aacaacgtat attttctcgc ctgtttttcg caatagtccg   720
agtaccatcg ataaagatat tggctacttg agtctgcaga cagtaataga atacatgtgt   780
aatgaggcgt ggagtagatg gtaa                                          804

SEQ ID NO: 269           moltype = DNA  length = 786
FEATURE                  Location/Qualifiers
misc_feature             1..786
                         note = Synthetic
source                   1..786
                         mol_type = other DNA
                         organism = synthetic construct
SEQUENCE: 269
atgaacaacg aatcccaggc caaagattcg tcgctgcgta tggaacctct ggaaaaggaa    60
aagggagcag ccgggcaggg tgcattgagt caaattcccc ccgaaagtta ccgaactaaa   120
tccccggcgg aactgctggg cgccggtaaa acgcgtgcgg atcttaactt tccagatgta   180
aaaaacgatt atgaactgga taacgcactt ataggacaaa cggttacaag caacggttgc   240
gtggtgaagg caccctgggt acgcaaggat tttaacactc cgggctattg gagcgaaggt   300
tatataaagc cctgcgctgc ttatctgtct tatattaaaa aagataccgt accgagcggc   360
acgtctattg aatacagctt aaccgcgaaa aaaggttttt cgcgacaatt tacagcatcc   420
acggaagtga aggtaggggt ttccgcaggg atcttcggtt gcgagacgag cctgaagtg    480
actacgggtt tttcgtactc cgaaaccata aatgaagaaa ctactgaaac ttggaagaag   540
actcttaccg gtccccaaga ttattggacc tttcagcctg ttttgctgta tgcctggaaa   600
gtcaatgcaa atgccctgtc ttatatgagc cctaaaccct cactttacta tacctctggc   660
aagaccacct atatctttag tccagttttt cgtaatagcc cgagcactat tgacaaagat   720
atcggctatt taagcttaca gaccgtcatc gagtatatgt gtaatgaagc gtggtctaga   780
tggtaa                                                              786

SEQ ID NO: 270           moltype = DNA  length = 786
FEATURE                  Location/Qualifiers
misc_feature             1..786
                         note = Synthetic
source                   1..786
                         mol_type = other DNA
                         organism = synthetic construct
SEQUENCE: 270
atgaataacg agagtcaagc caaagactca tctttacgca tggagccatt agaaaaagaa    60
aaaggagctg ctggacaggg tgcgctgagc caaattcccc ctgagtctta tcgtacaaaa   120
agtccggccg aattattagg cgctggtaaa acccgtgctg atcttaactt tccagatgtg   180
aaaaacgact acgagctgga caatgcgctc atcggccaaa cggtgaccag caatggctgc   240
gtagtgaaag caccctgggt ccgcaaagac tttaacacgc ctggctactg gtcagaaggc   300
tacatcaagc cttgcgcagc ctatctgagc tatatcaaga aagatactgt tccatcgggc   360
acaagtattg aatacagtct taccaaaaaa aagggtttta gtcgtgcgtt tacagcctca   420
acagaggtga agtaggtgt aagcgcaggt atttttgggt gcgagacatc attggaggta    480
acgacaggat tttcatattc tgagacaatt aatgaagaaa ctacagagac ctggaagaag   540
accttaaccg gcccacaaga ctactggacg tttcaaccgg ttcttttata tgcctggaag   600
gtgaatgcca atgccttatc ttatatgagt ccaaagccga gcttatatta tacttcaggc   660
aaaacgacct acattttcag cccagttttc cgcaattctc catcaaccat cgataaagac   720
attggatact tatcgctgca gacagttatt gagtatatgt gtaacgaagc ctggtcgcga   780
tggtga                                                              786

SEQ ID NO: 271           moltype = DNA  length = 786
FEATURE                  Location/Qualifiers
misc_feature             1..786
                         note = Synthetic
source                   1..786
                         mol_type = other DNA
                         organism = synthetic construct
SEQUENCE: 271
atgaataatg aatcccaggc caaagattcc agcctccgta tggaaccact ggagaaagaa    60
aaaggagctg ccggccaggg tgccctgagc caaatccctc cagagtcata tcgcacaaaa   120
tcgccagctg agctgttggg tgcagggaaa acacgtgctg acttgaattt cccagacgtc   180
aaaaacgatt atgaactgga caacgccctg attgggcaaa ccgtaacgtc gaacggctgt   240
gttgttaaag ctccttgggt acggaaagat tttaacaccc ctggctactg gtcagagggc   300
```

-continued

```
tatataaaac cctgtgcggc ttacctgtcg tatatcaaaa aggacacagt accttcaggg   360
acatcgatcg agtactccct gacaaaaaaa aaaggatttt caagacagtt tgctgcaagc   420
accgaggtca aagtaggtgt gtctgccggt atttttgggt gcgagacaag cctggaagta   480
acaaccggtt ttagctatag cgaaactatt aacgaggaaa ccacggagac atggaagaaa   540
actctgactg ggccgcaaga ttactggacg tttcagcccg tactgttata cgcatggaag   600
gttaatgcca atgcattgtc ttatatgtct cctaaaccgt ccttatacta tacatcaggt   660
aaaacaacgt acattttcag cccggtcttt cggaattccc ctagcacgat cgataaagat   720
attggttact tgtcgctgca gacggtcatt gaatacatgt gtaatgaagc gtggtcccgt   780
tggtag                                                              786

SEQ ID NO: 272          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 272
atgaataatg aatctcaagc gaaagattct tccctgcgta tggagccact ggagaaggaa   60
aaaggtgcag cgggacaggg cgccctgtca cagatcccac cagagagtta ccgaaccaag   120
agtccagcag agcttctcgg cgctggcaaa acccgtgcag acctgaattt tccagacgtt   180
aagaatgact atgaactgga taatgccctc attggtcaaa cggttacatc aaatggatgc   240
gtggttaaag ccccgtgggt gcgtaaagat tttaatacac ctgggtattg gtctgaaggt   300
tatatcaaac cgtgtgctgc ctacctgtct tatatcaaaa aagacacggt accgagcggt   360
acctctattg agtattcatt aacgaaaaaa aagggtttct ctcggcaatt tactgcgagc   420
actgaagtca aagttggcgt tagtgctggg atctttggtt gtgaaacctc gcttgccgtg   480
acgactgggt tctcctacag cgaaacaatc aacgaggaaa ctacggaaac ctggaagaaa   540
acgctgactg gtccgcagga ttattggacc tttcagccgg ttctcttata cgcctggaaa   600
gttaatgcca atgccctttc atacatgtca cccaaacctt cattgtacta cacatccggg   660
aaaacaacgt acatatttag cccggtattt cgcaacagtc cgagcacgat tgataaagac   720
atagggtatc tgtcattgca gaccgtgatt gaatatatgt gtaacgaagc ctggtcccgt   780
tggtga                                                              786

SEQ ID NO: 273          moltype = DNA   length = 786
FEATURE                 Location/Qualifiers
misc_feature            1..786
                        note = Synthetic
source                  1..786
                        mol_type = other DNA
                        organism = synthetic construct
SEQUENCE: 273
atgaataatg aaagccaggc aaaagattca tctctgcgta tggaaccgct ggaaaaagag   60
aaaggtgcgg ctggtcaggg ggcattatcc caaataccgc cagaaagtta cggaccaaaa   120
tccccagctg aattactggg cgcagggaaa acccgcgcag atctgaactt cccggatgtg   180
aagaatgact acgagctgga taacgcactg attgggcaga ccgttaccag caacggttgc   240
gttgtaaaag cgccttgggt cagaaaggac ttcaacactc caggctactg gtccgaaggg   300
tatatcaaag catgtgctgc ttacctgtcc tatataaaga aggatacggt tccgagtgga   360
acatcgatcg agtactctct gaccaaaaaa aaaggctttt ctcgtcaatt tactgcgagc   420
accgaagtaa aagtcggcgt ttcagccggg attttcggct gcgagaccag ccttgaggtc   480
gcaacggggt ttagctacag tgaaactatc aacgaagaga caacagaaac gtggaagaaa   540
accttaaccg ggcctcagga ttactggacg tttcagccgg ttcttctgta tgcttggaaa   600
gtaaacgcaa atgccttaag ctatatgagc ccaaaaccta gcttatatta cacctctggt   660
aaaaccactt atatcttttc tccagtattc cggaatagtc ccagcactat tgacaaagat   720
atcggttatc tgagcctgca gacagttata gagtatatgt gcaacgaggc ctggtcacgt   780
tggtaa                                                              786
```

INSECTICIDAL PROTEINS COMPOSITIONS AND METHODS OF USE

CROSS-REFERENCE TO RELATED APPLICATIONS

This application claims priority to U.S. Provisional Patent Application No. 63/644,183, filed on May 8, 2024, which is incorporated by reference herein in its entirety.

REFERENCE TO SEQUENCE LISTING

This application was filed with a Sequence Listing XML in ST.26 XML format accordance with 37 C.F.R. § 1.831 and PCT Rule 13ter. The Sequence Listing XML file submitted in the USPTO Patent Center, "218903-0036-WO01_GEN00015WOPCT_Sequence Listing.xml," was created on Apr. 9, 2025, contains 273 sequences, has a file size of 448 Kbytes (458,752 bytes), and is incorporated by reference in its entirety into the specification.

FIELD

This disclosure relates to the field of molecular biology, specifically, novel genes and engineered variants that encode pesticidal proteins useful for controlling pathogens and pests, particularly plant pests. These pesticidal proteins and the nucleic acid sequences that encode them are useful in preparing pesticidal compositions and in the production of transgenic pest-resistant plants. The disclosure also relates generally to compositions and methods for controlling pathogens and pests, particularly plant pests.

INTRODUCTION

Across the world, crops are subjected to multiple threats e.g., pests, plant diseases, and weeds. Losses due to pests and diseases are greatly threatening global food supply, hence the necessity to develop solutions to avoid partial or complete destruction of cultures. The main solutions are chemicals, biocontrols, or genetically modified organisms.

Current strategies use genes expressing pesticidal proteins to produce transgenic crops. These pesticidal proteins are generally derived from *Bacillus thuringiensis* ("Bt"), a Gram-positive spore forming soil bacterium. Current commercial pesticidal proteins include Bt Cry (crystal protein), or VIP (Vegetative Insecticidal Protein). Transgenic crops expressing insecticidal proteins are used to combat crop damage from insects.

The wide adoption of pesticidal protein-based technologies by farmers for controlling insects in the fields gave rise to resistance to these pesticidal proteins in some target pests in many parts of the world. One way of solving this problem is stacking pesticidal protein genes with different modes of action against insects in transformed plants. In order to find new pesticidal proteins with new modes of action, possible strategies involve discovering new pesticidal proteins from new sources or protein engineering. Thus, there is a need for novel insecticidal proteins for controlling plant pests.

SUMMARY

In one aspect, the disclosure relates to a method of protecting a plant from infection by a plant pathogen or pest, the method comprising: transforming the plant with a nucleic acid molecule encoding a polypeptide having at least 80% sequence identity to any one of SEQ ID NOs: 1-184 to generate a transformed plant expressing the polypeptide, wherein said polypeptide has pesticidal activity against the plant pathogen or pest; and regenerating the transformed plant expressing the polypeptide. In an embodiment, the polypeptide has at least 95% sequence identity to any one of SEQ ID NOs: 1-184. In another embodiment, the polypeptide is any one of SEQ ID NOs: 1-184. In another embodiment, the plant pathogen or pest is selected from the group consisting of fall armyworm (*Spodoptera frugiperda*), corn earworm (*Helicoverpa zea*), European corn borer (*Ostrinia nubilalis*), cotton boll worm (*Helicoverpa armigera*), black cutworm (*Agrotis ipsilon*), lesser cornstalk borer (*Elasmopalpus lignosellus*), Asian corn borer (*Ostinia furnacalis*), southwestern corn borer (*Diatraea grandiosella*), sugarcane borer (*Diatraea saccharalis*), western bean cutworm (*Striacosta albicosta*), velvetbean caterpillar (*Anticarsia gemmatalis*), western corn rootworm (*Diabrotica virgifera virgifera*), and combinations thereof.

In a further aspect, the disclosure relates to a transformed plant, seed, or plant part comprising a recombinant nucleic acid molecule encoding a polypeptide having at least 80% sequence identity to any one of SEQ ID NOs: 1-184 stably incorporated into a genome of the transformed plant, seed, or plant part, wherein the transformed plant, seed, or plant part stably expresses the polypeptide, and wherein the polypeptide has pesticidal activity against a plant pathogen or pest. In an embodiment, the polypeptide has at least 95% sequence identity to any one of SEQ ID NOs: 1-184. In another embodiment, the polypeptide is any one of SEQ ID NOs: 1-184. In another embodiment, the transformed plant, seed, or plant part is selected from the group consisting of rice, barley, sorghum, soybean, cotton, maize, rapeseed, sugar cane, tobacco, sunflower, and wheat.

Another aspect of the disclosure provides a recombinant nucleic acid molecule comprising a polynucleotide sequence encoding a polypeptide having at least 80% sequence identity to any one of SEQ ID NOs: 1-184, wherein the polypeptide has pesticidal activity against a plant pathogen or pest. In an embodiment, the polypeptide has at least 95% sequence identity to any one of SEQ ID NOs: 1-184. In another embodiment, the polypeptide is any one of SEQ ID NOs: 1-184. In another embodiment, the polynucleotide sequence encoding the polypeptide is operably linked to one or more promoter sequences.

Another aspect of the disclosure provides a vector comprising a recombinant nucleic acid molecule comprising a polynucleotide sequence encoding a polypeptide having at least 80% sequence identity to any one of SEQ ID NOs: 1-184, wherein the polypeptide has pesticidal activity against a plant pathogen or pest. In an embodiment, the polypeptide has at least 95% sequence identity to any one of SEQ ID NOs: 1-184. In another embodiment, the polypeptide is any one of SEQ ID NOs: 1-184.

Another aspect of the disclosure provides a transformed host cell comprising a recombinant nucleic acid molecule comprising a polynucleotide sequence encoding a polypeptide having at least 80% sequence identity to any one of SEQ ID NOs: 1-184, wherein the polypeptide has pesticidal activity against a plant pathogen or pest. In an embodiment, the polypeptide has at least 95% sequence identity to any one of SEQ ID NOs: 1-184. In another embodiment, the polypeptide is any one of SEQ ID NOs: 1-184.

Another aspect of the disclosure provides a method of treating a plant or plant part against a plant pathogen or pest, the method comprising: applying to the plant or plant part an effective amount of at least one polypeptide having at least 80% sequence identity to any one of SEQ ID NOs: 1-184, wherein the polypeptide has pesticidal activity against the plant pathogen or pest. In an embodiment, the polypeptide has at least 95% sequence identity to any one of SEQ ID NOs: 1-184. In another embodiment, the polypeptide is any one of SEQ ID NOs: 1-184.

Another aspect of the disclosure provides a composition having insecticidal activity against a plant pathogen or pest, the composition comprising an effective amount of at least one polypeptide having at least 80% sequence identity to any one of SEQ ID NOs: 1-184. In an embodiment, the polypeptide has at least 95% sequence identity to any one of SEQ ID NOs: 1-184. In another embodiment, the polypeptide is any one of SEQ ID NOs: 1-184.

Another aspect of the disclosure provides polynucleotides comprising a polynucleotide sequence encoding any of the insecticidal polypeptides described herein operably linked to a heterologous regulatory element.

Another aspect of the disclosure provides cells comprising any of the polynucleotides described herein. In an embodiment, the cell is a plant cell or a bacteria cell.

Another aspect of the disclosure provides modified plants comprising any of the polynucleotides or cells described herein.

Another aspect of the disclosure provides compositions and methods for modifying bacteria, plants, plant cells, tissues, and seeds to provide insect resistance. In some embodiments, nucleic acid molecules encode sequences for pesticidal and insecticidal polypeptides, vectors comprise those nucleic acid molecules, and host cells comprise the vectors. Compositions may also include the pesticidal polypeptide sequences and antibodies to those polypeptides. Compositions may also comprise modified bacteria, plants, plant cells, tissues, and seeds.

This disclosure provides for other aspects and embodiments that will be apparent considering the following detailed description and accompanying figures.

BRIEF DESCRIPTION OF THE DRAWINGS

FIG. 1 is a table of descriptions for SEQ ID NOs: 1-273.

FIG. 3A is a homology table showing amino acid sequence identity for the disclosed insecticidal proteins of SEQ ID NOs: 1, 12, 19, 20, 24, 30, 42, 45, 46, 50, 55, and 57. FIG. 3B is a homology table showing amino acid sequence identity for the disclosed insecticidal proteins of SEQ ID NOs: 1 and 174-184.

Figure 2:
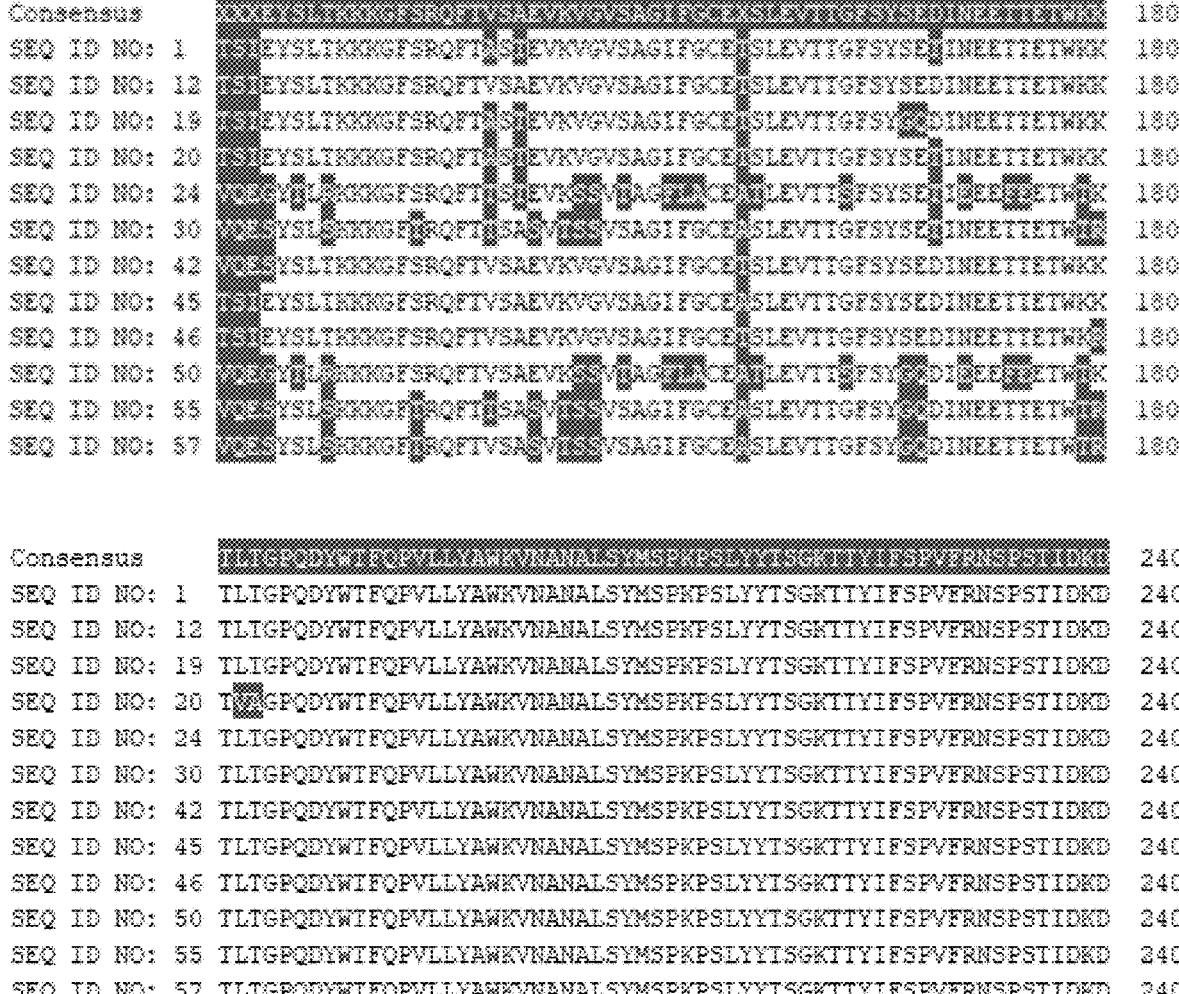
FIG. 2 is a depiction of a sequence alignment between the disclosed insecticidal proteins of SEQ ID NOs: 1, 12, 19, 20, 24, 30, 42, 45, 46, 50, 55, and 57.

Before any embodiments of this disclosure are explained in detail, it is to be understood that the disclosure is not limited in its application to the details of construction and the arrangement of components set forth in the following description or illustrated in the accompanying figures. Also, it is to be understood that the phraseology and terminology used herein is for the purpose of description and should not be regarded as limiting.

DETAILED DESCRIPTION

Described herein are compositions and methods comprising insecticidal proteins useful for conferring pesticidal activity. Disclosed compositions and methods may include isolated, recombinant, engineered, and purified polypeptides having pesticidal activity. In some embodiments, recombinant nucleic acid molecules including DNA constructs and vectors that encode polypeptides having pesticidal activity are described herein. In some embodiments, nucleic acid molecules and polypeptides may be described as DNA constructs and expression cassettes for transforming plants, plant tissues, plant parts, plant cells, and plant seeds, as well as microorganisms. Polypeptides having pesticidal activity as described herein may provide useful alternatives to those currently deployed in commercial transgenic plants.

Unless otherwise defined herein, all technical and scientific terms used in connection with the present disclosure shall have the same meanings that are commonly understood by those of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting. Further, unless otherwise required by context, singular terms shall include pluralities and plural terms shall include the singular.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, such as the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, preferably within 5-fold, and more preferably within 2-fold, of a value.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an organism to which the nucleic acid is administered. The coding sequence may be codon optimized.

"Complement" or "complementary" as used herein can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

The terms "control," "reference level," and "reference" are used herein interchangeably. The reference level may be a predetermined value or range, which is employed as a benchmark against which to assess the measured result. "Control group" as used herein refers to a group of control organisms. The predetermined level may be a cutoff value from a control group. The predetermined level may be an average from a control group. The normal levels or ranges for a target or for a protein activity may be defined in accordance with standard practice. A control may be an organism or cell without a vector as detailed herein. A control may be an organism, or a sample therefrom, whose condition is known. The organism, or sample therefrom, may be healthy, exposed to a toxin, exposed to a toxin prior to treatment, exposed to a toxin during treatment, or exposed to a toxin after treatment, or a combination thereof.

"Derived" and "derived from" as used herein refers to a DNA or amino acid sequence or a part of a DNA or amino acid sequence that has part or all of the sequence found in a native gene or protein.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes or gene fragments that originally coded for separate polypeptides. The translation of the fusion gene results in a single polypeptide with functional properties derived from each of the original polypeptides. A "chimeric protein" as used herein refers to a polypeptide comprising at least one polypeptide segment from two heterologous genes or two heterologous polypeptides.

"Genetic construct" or "construct" as used herein refers to the DNA or RNA nucleic acid molecules that comprise a polynucleotide that encodes a protein. The coding sequence includes initiation and termination signals operably linked to regulatory elements including a promoter and polyadenylation signal capable of directing expression in the cells of the organism to which the nucleic acid molecule is administered. As used herein, the term "expressible form" refers to gene constructs that contain the necessary regulatory elements operable linked to a coding sequence that encodes a protein such that when present in the cell of the organism, the coding sequence will be expressed.

The term "heterologous" as used herein refers to nucleic acid comprising two or more subsequences that are not found in the same relationship to each other in nature. For instance, a nucleic acid that is recombinantly produced typically has two or more sequences from unrelated genes synthetically arranged to make a new functional nucleic acid, for example, a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. Similarly, a heterologous protein indicates that the protein comprises two or more subsequences that are not found in the same relationship to each other in nature (for example, a "fusion protein," where the two subsequences are encoded by a single nucleic acid sequence). A heterologous polynucleotide may be created using any gene editing or molecular biological technique. As used herein, a "heterologous domain" refers to a protein domain region that is combined with one or more naturally occurring domain regions to form a non-native (non-naturally occurring) engineered fusion protein, where the heterologous domain and the one or more naturally occurring domain regions are not found in the same relationship to each other in nature.

"Identical" or "identity" as used herein in the context of two or more polynucleotide or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of a single sequence are included in the denominator but not the numerator of the calculation. When comparing DNA and RNA, thymine (T) and uracil (U) may be considered equivalent. Determining the percent sequence identity between any two or more nucleic acid or amino acid sequences can be accomplished using one or more mathematical algorithms. For example, identity may be performed manually or by using a computer sequence algorithm such as BLAST or BLAST 2.0.

"Natural gene" as used herein refers to a gene that has not undergone a change, such as a loss, gain, or exchange of genetic material. The natural gene undergoes normal gene transmission and gene expression. For example, a natural gene may be a wild-type (i.e., native) gene.

"Nucleic acid" or "oligonucleotide" or "polynucleotide" as used herein means at least two nucleotides covalently linked together. The depiction of a single strand also defines the sequence of the complementary strand. Thus, a polynucleotide also encompasses the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a target sequence under stringent hybridization conditions. Thus, a polynucleotide also encompasses a probe that hybridizes under stringent hybridization conditions. Polynucleotides may be single stranded or double stranded or may contain portions of both double stranded and single stranded sequence. The polynucleotide can be nucleic acid, natural or synthetic, DNA, genomic DNA, cDNA, RNA, or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

"Open reading frame" refers to a stretch of codons that begins with a start codon and ends at a stop codon. In eukaryotic genes with multiple exons, introns are removed, and exons are then joined together after transcription to yield the final mRNA for protein translation. An open reading frame may be a continuous stretch of codons. In some embodiments, the open reading frame only applies to spliced mRNAs, not genomic DNA, for expression of a protein.

"Operably linked" as used herein means that expression of a gene is under the control of a or influenced by a regulatory element (e.g., promoter) with which it is spatially connected. A regulatory element may be positioned 5' (upstream) or 3' (downstream) of a gene. The distance between a regulatory element and a gene may be approximately the same as the distance between that regulatory element and the gene it controls in the gene from which the regulatory element is derived. Variation in this distance may be accommodated without loss of regulatory function. Nucleic acid or amino acid sequences are "operably linked" (or "operatively linked") when placed into a functional relationship with one another. For instance, a regulatory element is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain. With respect to fusion polypeptides, the terms "operatively linked" and "operably linked" can refer to the fact that each of the components performs the same function in linkage to the other component as it would if it were not so linked.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and transport proteins. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, for example, enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units. A "motif" is a portion of a polypeptide sequence and includes at least two amino acids. A motif may be 2 to 20, 2 to 15, or 2 to 10 amino acids in length. A domain may be comprised of a series of the same type of motif.

"Pest" includes, but is not limited to, insects, fungi, bacteria, nematodes, mites, ticks, and the like. Insect pests may include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, and Trichoptera.

In certain embodiments described herein, insect pests may include larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (*Diaprepes* root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exclamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

In other embodiments, insect pests may include immatures and adults of the order Diptera, including leafminers *Agromyza parvicornis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other Nematocera.

Lepidoptera insects may include, but are not limited to, armyworms, cutworms, loopers, and heliothines in the family Noctuidae: *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hubner (cotton leaf worm); *Anticarsia gemmatalis* Hubner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (Xylomyges) *curialis* Grote (citrus cutworm); *Euxoa messoria* Harris (darksided cutworm); *Helicoverpa armigera* Hubner (American bollworm); *H. zea* Boddie (corn earworm or cotton bollworm); *Heliothis virescens* Fabricius (tobacco budworm); *Hypena scabra* Fabricius (green cloverworm); *Mamestra configurata* Walker (bertha armyworm); *M. brassicae* Linnaeus (cabbage moth); *Melanchra picta* Harris (zebra caterpillar); *Pseudaletia unipuncta* Haworth (armyworm); *Pseudoplusia includens* Walker (soybean looper); *Richia albicosta* Smith (Western bean cutworm); *Spodoptera frugiperda* JE Smith (fall armyworm); *S. exigua* Hubner (beet armyworm); *S. litura* Fabricius (tobacco cutworm, cluster caterpillar); *Trichoplusia ni* Hubner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); Corcyra cephalonica Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hubner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hubner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hubner (European corn borer); *Plodia interpunctella* Hubner (Indian meal moth); *Scirpophaga incertulas* Walker (yellow stem borer); *Udea rubigalis* Guenee (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rosslerstamm (summer fruit *tortrix* moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hubner (vine moth); *Grapholita molesta* Busck (oriental fruit moth); *Lobesia botrana* Denis & Schiffermüller (European grape vine moth); *Platynota flavedana* Clemens (variegated leafroller); *P. stultana* Walsingham (omnivorous leafroller); *Spilonota ocellana* Denis & Schiffermüller (eyespotted bud moth); and *Suleima helianthana* Riley (sunflower bud moth).

Additional Lepidoptera agronomic pests may include, but are not limited to, *Alsophila pometaria* Harris (fall cankerworm); *Anarsia lineatella* Zeller (peach twig borer); *Anisota senatoria* J. E. Smith (orange striped oakworm); Antheraea pernyi Guérin-Méneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hubner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Méneville (grapeleaf skeletonizer); *Heliothis subflexa* Guenee; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia calfornica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer) and *Yponomeuta padella* Linnaeus (ermine moth).

In certain embodiments, insect pests may include those of the order Hemiptera including, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Non-limiting examples of agronomically important insect pests from the order Hemiptera include: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear *psylla*); *Calocoris norvegicus* Gmelin (potato capsid bug); *Chaetosiphon fragaefolii* Cockerell (strawberry aphid); *Cimicidae* spp.; *Coreidae* spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schaffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan *phylloxera*); *Planococcus citri* Risso (citrus mealybug); *Plesiocoris rugicolfis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); Pyrrhocoridae spp.; *Quadraspidiotus perniciosus* Comstock (San Jose scale); Reduviidae spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); Tinidae spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon *psylla*); and *Typhlocyba pomaria* McAtee (white apple leafhopper).

In other embodiments, insect pests may also include adults and larvae of the order Acari (mites) including, but not limited to, *Aceria tosichella* Keifer (wheat curl mite); *Panonychus ulmi* Koch (European red mite); *Petrobia latens* Muller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

In addition, insect pests may also include those of the order Thysanura, such as *Lepisma saccharina* Linnaeus (silverfish) and *Thermobia domestica* Packard (firebrat).

Insect pests may also include those of the order Isoptera, including those of the termitidae family, such as, but not limited to, *Cylindrotermes nordenskioeldi* Holmgren and *Pseudacanthotermes militaris* Hagen (sugarcane termite).

Insect pests may also include those of the order Thysanoptera, including but not limited to *thrips*, such as *Stenchaetothrips minutus* van Deventer (sugarcane *thrips*).

In other embodiments, arthropod pests may include: spiders in the order Araneae such as *Loxosceles reclusa* Gertsch & Mulaik (brown recluse spider); and the *Latrodectus*

*mactans* Fabricius (black widow spider); and centipedes in the order Scutigeromorpha such as *Scutigera coleoptrata* Linnaeus (house centipede).

As used herein, "pesticidal activity," "insecticidal," "pesticidal," or "insecticidal activity" means that the proteins, polypeptides, or toxins of the present disclosure, including proteins that have homology to such proteins, polypeptides, or toxins, are able to induce the stunting (sub-lethal effect) and/or killing (lethal effect) of insect pathogens or pests, including but not limited to, members of the Lepidoptera, Diptera, Hemiptera, and Coleoptera orders or the Nematoda phylum.

In certain embodiments described herein, the compositions, plants, cells, and methods may further comprise at least one additional pesticidal protein as a pesticidal stacking partner to help, for example, in reducing the likelihood of resistance development or in expanding the spectrum of insect inhibition. These additional pesticidal proteins can be isolated from organisms including, for example, *Bacillus* sp., *Pseudomonas* sp., *Photorhabdus* sp., *Xenorhabdus* sp., *Clostridium bifermentans*, and *Paenibacillus popilliae*. In some embodiments, transgenic or modified plants expressing insecticidal proteins as described herein may also be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Additional pesticidal proteins may include, but are not limited to: insecticidal proteins from *Pseudomonas* sp. such as PSEEN3174 (Monalysin; (2011) PLoS Pathogens 7: 1-13); from *Pseudomonas protegens* strain CHAO and Pf-5 (previously *fluorescens*) (Pechy-Tarr, (2008) Environmental Microbiology 10:2368-2386; GenBank Accession No. EU400157); from *Pseudomonas taiwanensis* (Liu, et al., (2010) J. Agric. Food Chem., 58: 12343-12349) and from *Pseudomonas pseudoalcaligenes* (Zhang, et al., (2009) Annals of Microbiology 59:45-50 and Li, et al., (2007) Plant Cell Tiss. Organ Cult. 89: 159-168); insecticidal proteins from *Photorhabdus* sp. and *Xenorhabdus* sp. (Hinchliffe, et al., (2010) The Open Toxicology Journal, 3: 101-1 18 and Morgan, et al., (2001) Applied and Envir. Micro. 67:2062-2069); U.S. Pat. Nos. 6,048,838, and 6,379,946; a PIP-1 polypeptide of U.S. Pat. No. 9,688,730; an AflP-1A and/or AflP-1 B polypeptide of U.S. Pat. No. 9,475,847; a PIP-47 polypeptide of U.S. Pub. Number US20160186204; an IPD045 polypeptide, an IPD064 polypeptide, an IPD074 polypeptide, an IPD075 polypeptide, and an IPD077 polypeptide of PCT Pub. No. WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of U.S. Pat. Pub. No. US20160366891; a PtIP-50 polypeptide and a PtIP-65 polypeptide of U.S. Pub. Number US20170166921; an IPD098 polypeptide, an IPD059 polypeptide, an IPD108 polypeptide, an IPD109 polypeptide of U.S. Ser. No. 62/521,084; an IPD110 polypeptide, an IPD113 polypeptide, a PtIP-83 polypeptide of U.S. Pub. Number US20160347799; a PtIP-96 polypeptide of U.S. Pub. Number US20170233440; an IPD079 polypeptide of PCT Pub. No. WO2017/23486; an IPD082 polypeptide of PCT Pub. No. WO 2017/105987, an IPD090 polypeptide of Serial Number PCT/US 17/30602, an IPD093 polypeptide of U.S. Ser. No. 62/434,020; an IPD103 polypeptide of Serial Number PCT/US 17/39376; an IPD101 polypeptide of U.S. Ser. No. 62/438,179; an IPD121 polypeptide of U.S. Serial Number U.S. 62/508,514; and delta (d)-endotoxins including, but not limited to a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry72 classes of d-endotoxin polypeptides and the *B. thuringiensis* cytolytic cyt1 and cyt2 genes. Members of these classes of *B. thuringiensis* insecticidal proteins (see Crickmore et al., "*Bacillus thuringiensis* toxin nomenclature" (2011), at bpprc.org).

Examples of d-endotoxins also include, but are not limited to: Cry1A proteins of U.S. Pat. Nos. 5,880,275, 7,858, 849, and 8,878,007; a Cry1Ac mutant of U.S. Pat. No. 9,512,187; a DIG-3 or DIG-11 toxin (N-terminal deletion of a-helix 1 and/or a-helix 2 variants of cry proteins such as Cry1A, Cry3A) of U.S. Pat. Nos. 8,304,604, 8,304,605 and 8,476,226; Cry1B of U.S. patent application Ser. No. 10/525,318, U.S. Pat. App. Pub. No. US20160194364, and U.S. Pat. Nos. 9,404,121 and 8,772,577; Cry1B variants of PCT Pub. No. WO2016/61197 and Serial Number PCT/US17/27160; Cry1C of U.S. Pat. No. 6,033,874; Cry1D protein of US20170233759; a Cry1E protein of PCT Serial Number PCT/US17/53178; a Cry1F protein of U.S. Pat. Nos. 5,188,960 and 6,218,188; Cry1A/F chimeras of U.S. Pat. Nos. 7,070,982; 6,962,705 and 6,713,063; a Cry1L protein of PCT Pub. No. WO 2017/0233759; an engineered Cry1G as set forth in WO2018111553A1; a CryU variant of U.S. Pub. US20170240603; a Cry2 protein such as Cry2Ab protein of U.S. Pat. No. 7,064,249 and Cry2A.127 protein of U.S. Pat. No. 7,208,474; a Cry3A protein including but not limited to an engineered hybrid insecticidal protein (eHIP) created by fusing unique combinations of variable regions and conserved blocks of at least two different Cry proteins (U.S. Pat. App. Pub. No. 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,339,092, 7,378,499, 7,462,760, and 9,593,345; a Cry9 protein such as such as members of the Cry9A, Cry9B, Cry9C, Cry9D, Cry9E and Cry9F families including the Cry9 protein of U.S. Pat. Nos. 9,000,261 and 8,802,933, and WO 2017/132188; a Cry15 protein of Naimov, et al., (2008) Applied and Environmental Microbiology, 74:7145-7151; a Cry14 protein of U.S. Pat. No. 8,933,299; a Cry22, a Cry34Abl protein of U.S. Pat. Nos. 6,127,180, 6,624,145, and 6,340,593; a truncated Cry34 protein of U.S. Pat. No. 8,816,157; a CryET33 and cryET34 protein of U.S. Pat. Nos. 6,248,535, 6,326,351, 6,399,330, 6,949,626, 7,385,107 and 7,504,229; a CryET33 and CryET34 homologs of U.S. Pat. Pub. No. 2006/0191034, 2012/0278954, and PCT Pub. No. WO 2012/139004; a Cry35Abl protein of U.S. Pat. No. 6,083,499, 6,548,291 and 6,340,593; a Cry46 protein of U.S. Pat. No. 9,403,881, a Cry51 protein, a Cry binary toxin; a TIC901 or related toxin; TIC807 of U.S. Pat. App. Pub. No. 2008/0295207; TIC853 of U.S. Pat. No. 8,513,493; ET29, ET37, TIC809, TIC810, TIC812, TIC127, TIC128 of PCT US2006/033867; engineered Hemipteran toxic proteins of U.S. Pat. App. Pub. No. US20160150795, AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of U.S. Pat. App. Pub. No. 2004/0250311; AXMI-006 of U.S. Pat. App. Pub. No. 2004/0216186; AXMI-007 of U.S. Pat. App. Pub. No. 2004/0210965; AXMI-009 of U.S. Pat. Application Number 2004/0210964; AXMI-014 of U.S. Pat. App. Pub. No. 2004/0197917; AXMI-004 of U.S. Pat. App. Pub. No. 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of U.S. Pat. App. Pub. No. 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of U.S. Pat. App. Pub. No. 2011/0263488; AXMI046, AXMI048, AXMI050, AXMI051, AXMI052, AXMI053, AXMI054, AXMI055, AXMI056, AXMI057, AXMI058, AXMI059, AXMI060, AXMI061, AXMI067, AXMI069, AXMI071, AXMI072, AXMI073, AXMI074, AXMI075, AXMI087, AXMI088, AXMI093, AXMI070, AXMI080, AXMI081, AXMI082, AXMI091, AXMI092, AXMI096, AXMI097, AXMI098, AXMI099, AXMI 100, AXMI 101, AXMI 102, AXMI 103, AXMI 104, AXMI 107, AXMI 108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI125, AXMI126, AXMI127, AXMI129, AXMI151, AXMI161, AXMI164, AXMI183, AXMI132, AXMI137, AXMI138 of U.S. Pat. Nos. 8,461,421 and 8,461,422; AXMI-R1 and related proteins of U.S. Pat. App. Pub. No. 2010/0197592; AXMI221Z, AXMI222z, AXMI223z, AXMI224z and AXMI225Z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of U.S. Pat. App. Pub. No. 2010/0298211; AXMI-066 and AXMI-076 of U.S. Pat. App. Pub. No. 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, dsAXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of U.S. Pat. No. 8,461,421; AXMI192 of U.S. Pat. No. 8,461,415; AXMI281 of U.S. Pat. App. Pub. No. US20160177332; AXMI422 of U.S. Pat. No. 8,252,872; cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of U.S. Pat. App. Pub. No. 2011/0064710; and the Cry proteins MP032, MP049, MP051, MP066, MP068, MP070, MP091S, MP109S, MP114, MP121, MP134S, MP183S, MP185S, MP186S, MP195S, MP197S, MP208S, MP209S, MP212S, MP214S, MP217S, MP222S, MP234S, MP235S, MP237S, MP242S, MP243, MP248, MP249S, MP251M, MP252S, MP253, MP259S, MP287S, MP288S, MP295S, MP296S, MP297S, MP300S, MP304S, MP306S, MP310S, MP312S, MP314S, MP319S, MP325S, MP326S, MP327S, MP328S, MP334S, MP337S, MP342S, MP349S, MP356S, MP359S, MP360S, MP437S, MP451S, MP452S, MP466S, MP468S, MP476S, MP482S, MP522S, MP529S, MP548S, MP552S, MP562S, MP564S, MP566S, MP567S, MP569S, MP573S, MP574S, MP575S, MP581 S, MP590, MP594S, MP596S, MP597, MP599S, MP600S, MP601 S, MP602S, MP604S, MP626S, MP629S, MP630S, MP631S, MP632S, MP633S, MP634S, MP635S, MP639S, MP640S, MP644S, MP649S, MP651S, MP652S, MP653S, MP661 S, MP666S, MP672S, MP696S, MP704S, MP724S, MP729S, MP739S, MP755S, MP773S, MP799S, MP800S, MP801S, MP802S, MP803S, MP805S, MP809S, MP815S, MP828S, MP831 S, MP844S, MP852, MP865S, MP879S, MP887S, MP891S, MP896S, MP898S, MP935S, MP968, MP989, MP993, MP997, MP1049, MP1066, MP1067, MP1080, MP1081, MP1200, MP1206, MP1233, and MP1311 of U.S. Ser. No. 62/607,372.

Other exemplary additional pesticidal proteins for the control of Lepidopteran pests may include an insect inhibitory protein such as, but not limited to, Cry1A (U.S. Pat. No. 5,880,275), Cry1Ab, Cry1Ac, Cry1A.105, Cry1Ae, Cry1B (U.S. Pat. Pub. Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AXMI-045 (U.S. Pat. Pub. 2013-0117884 A1), AXMI-52, AXMI-58, AXMI-88, AXMI-97, AXMI-102, AXMI-112, AXMI-117, AXMI-100 (U.S. Pat. Pub. 2013-0310543 A1), AXMI-115, AXMI-113, AXMI-005 (U.S. Pat. Pub. 2013-0104259 A1), AXMI-134 (U.S. Pat. Pub. 2013-0167264 A1), AXMI-150 (U.S. Pat. Pub. 2010-0160231 A1), AXMI-184 (U.S. Pat. Pub. 2010-0004176 A1), AXMI-196, AXMI-204, AXMI-207, AXMI-209 (U.S. Pat. Pub. 2011-0030096 A1), AXMI-218, AXMI-220 (U.S. Pat. Pub. 2014-0245491 A1), AXMI-221z, AXMI-222z, AXMI-223z, AXMI-224z, AXMI-225z (U.S. Pat. Pub. 2014-0196175 A1), AXMI-238 (U.S. Pat. Pub. 2014-0033363 A1), AXMI-270 (U.S. Pat. Pub. 2014-0223598 A1), AXMI-345 (U.S. Pat. Pub. 2014-0373195 A1), DIG-3 (U.S. Pat. Pub. 2013-0219570 A1), DIG-5 (U.S. Pat. Pub. 2010-0317569 A1), DIG-11 (U.S. Pat. Pub. 2010-0319093 A1), AflP-1A and derivatives thereof (U.S. Pat. Pub. 2014-0033361 A1), AflP-1B and derivatives thereof (U.S. Pat. Pub. 2014-0033361 A1), PIP-1APIP-1B (U.S. Pat. Pub. 2014-0007292 A1), PSEEN3174 (U.S. Pat. Pub. 2014-0007292 A1), AECFG-592740 (U.S. Pat. Pub. 2014-0007292 A1), Pput_1063 (U.S. Pat. Pub. 2014-0007292 A1), Pput_1064 (U.S. Pat. Pub. 2014-0007292 A1), GS-135 and derivatives thereof (U.S. Pat. Pub. 2012-0233726 A1), GS153 and derivatives thereof (U.S. Pat. Pub. 2012-0192310 A1), GS154 and derivatives thereof (U.S. Pat. Pub. 2012-0192310 A1), GS155 and derivatives thereof (U.S. Pat. Pub. 2012-0192310 A1), SEQ ID NO: 2 and derivatives thereof as described in U.S. Pat. Pub. 2012-0167259 A1, SEQ ID NO: 2 and derivatives thereof as described in U.S. Pat. Pub. 2012-0047606 A1, SEQ ID NO: 2 and derivatives thereof as described in U.S. Pat. Pub. 2011-0154536 A1, SEQ ID NO: 2 and derivatives thereof as described in U.S. Pat. Pub. 2011-0112013 A1, SEQ ID NO:

2 and 4 and derivatives thereof as described in U.S. Pat. Pub. 2010-0192256 A1, SEQ ID NO: 2 and derivatives thereof as described in U.S. Pat. Pub. 2010-0077507 A1, SEQ ID NO: 2 and derivatives thereof as described in U.S. Pat. Pub. 2010-0077508 A1, SEQ ID NO: 2 and derivatives thereof as described in U.S. Pat. Pub. 2009-0313721 A1, SEQ ID NO: 2 or 4 and derivatives thereof as described in U.S. Pat. Pub. 2010-0269221 A1, SEQ ID NO: 2 and derivatives thereof as described in U.S. Pat. No. 7,772,465 B2, CF161_0085 and derivatives thereof as described in WO2014/008054 A2, Lepidopteran toxic proteins and their derivatives as described in U.S. Pat. Pub. 2008-0172762 A1, 2011-0055968 A1, and 2012-0117690 A1; SEQ ID NO: 2 and derivatives thereof as described in U.S. Pat. No. 7,510,878 B2, SEQ ID NO: 2 and derivatives thereof as described in U.S. Pat. No. 7,812,129 B1; and the like.

In other embodiments, exemplary additional pesticidal proteins for the control of Coleopteran pests may include an insect inhibitory protein such as, but not limited to, Cry3Bb (U.S. Pat. No. 6,501,009), Cry1C variants, Cry3A variants, Cry3, Cry3B, Cry34/35, 5307, AXMI-134 (U.S. Pat. Pub. 2013-0167264 A1) AXMI-184 (U.S. Pat. Pub. 2010-0004176 A1), AXMI-205 (U.S. Pat. Pub. 2014-0298538 A1), AXMI-207 (U.S. Pat. Pub. 2013-0303440 A1), AXMI-218, AXMI-220 (U.S. Pat. Pub. 20140245491A1), AXMI-221z, AXMI-223z (U.S. Pat. Pub. 2014-0196175 A1), AXMI-279 (U.S. Pat. Pub. 2014-0223599 A1), AXMI-R1 and variants thereof (U.S. Pat. Pub. 2010-0197592 A1), TIC407, TIC417, TIC431, TIC807, TIC853, TIC901, TIC1201, TIC3131, DIG-10 (U.S. Pat. Pub. 2010-0319092 A1), eHIPs (U.S. Pat. Pub. 2010/0017914), IP3 and variants thereof (U.S. Pat. Pub. 2012-0210462 A1), and ω-Hexatoxin-Hv1a (U.S. Pat. Pub. 2014-0366227 A1).

In other embodiments, exemplary additional pesticidal proteins for the control of Hemipteran pests may include Hemipteran-active proteins such as, but not limited to, TIC1415 (U.S. Pat. Pub. 2013-0097735 A1), TIC807 (U.S. Pat. No. 8,609,936), TIC834 (U.S. Pat. Pub. 2013-0269060 A1), AXMI-036 (U.S. Pat. Pub. 2010-0137216 A1), and AXMI-171 (U.S. Pat. Pub. 2013-0055469 A1).

Additional pesticidal proteins for the control of Coleopteran, Lepidopteran, and Hemipteran insect pests can be found on the *Bacillus thuringiensis* toxin nomenclature website (btnomenclature.info).

As used herein, "plant cell" or "plant cells" means a cell obtained from or found in seeds, suspension cultures, embryos, meristematic regions, callus tissue, leaves, roots, shoots, gametophytes, sporophytes, pollen, protoplasts, and microspores. Plant cell also includes modified cells, such as protoplasts, obtained from the aforementioned tissues, as well as plant cell tissue cultures from which plants can be regenerated, plant calli and plant clumps. As used herein, "plant part" or "plant parts" means organs such as embryos, pollen, ovules, seeds, flowers, kernels, ears, cobs, leaves, husks, stalks, stems, roots, root tips, anthers, silk and the like. As used herein, "plant" or "plants" means whole plants and their progeny. Progeny, variants, and mutants of the regenerated plants are also included, provided that they comprise the introduced nucleic acid molecule as described herein.

"Promoter" as used herein means a synthetic or naturally derived molecule which is capable of conferring, activating, or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organelle in which expression occurs or, with respect to the developmental stage at which expression occurs, or in response to external stimuli such as physiological stresses, pathogens or pests, pesticides, metal ions, or inducing agents. Representative examples of promoters include the promoter of the 35S gene from the cauliflower mosaic virus, the promoter from the cassava vein mosaic virus, the promoter of the rice actin1 gene, the promoter of the subterranean clover virus gene 4, the promoter region of the ubiquitin 4 gene, and the promoter region of the maize polyubiquitin 1 gene. A "regulatory element" is a polynucleotide sequence that has an effect upon transcription of a gene. A regulatory element may include, but is not limited to, a promoter, enhancer, terminator, or other sequences that affect transcription of a gene.

The term "recombinant" when used with reference to, for example, a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed, or not expressed at all.

"Sample" or "test sample" as used herein can mean any sample in which the presence and/or level of a target is to be detected or determined or any sample comprising a vector as detailed herein. The sample may be a biological sample. Samples may include liquids, solutions, emulsions, or suspensions. Samples can be obtained by any means known in the art. The sample can be used directly as obtained from an organism or can be pre-treated, such as by filtration, distillation, extraction, concentration, centrifugation, inactivation of interfering components, addition of reagents, and the like, to modify the character of the sample in some manner as discussed herein or otherwise as is known in the art.

"Subject" and "organism" as used herein interchangeably refer to any plant, seed, plant part, or plant material including, but not limited to, a plant in need of the herein described compositions or methods. The plant may be, for example but not limited to, rice, barley, sorghum, soybean, cotton, maize, rapeseed, sugar cane, tobacco, sunflower, or wheat. The subject may be at any stage of development, such as, for example, seed, sprout, vegetative, budding, flowering, or ripening stages. The subject may be hermaphrodite or dioecious. In some embodiments, the subject may have a specific genetic marker. In some embodiments, the subject may be undergoing other forms of treatment.

"Substantially identical" can mean that a first and second amino acid or polynucleotide sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or greater amino acids or nucleotides, respectively.

As used herein, "introducing" means presenting to the plant cell, plant part, or plant, a nucleic acid molecule or construct in such a manner that it gains access to the interior of a cell of the plant. Methods of the present disclosure include introducing and expressing in a plant cell, plant part, or plant a nucleic acid sequence or construct as described herein. The methods described herein do not depend on the particular method for introducing the nucleic acid molecule or nucleic acid construct into the plant cell, plant part, or plant, only that it gains access to the interior of at least one cell of the plant or plant part. Methods of introducing nucleotide sequence, selecting transformation event, and regenerating whole plants, which may require routine modification in respect of a particular plant species, are known in the art. The methods may include, but are not limited to, stable transformation methods, transient transformation methods, virus-mediated methods, and sexual breeding. As such, the nucleic acid molecule or construct can be carried episomally or integrated into the genome of the host cell.

"Transformed plant cells" as used herein refer to plant cells that have been transformed that can be grown into plants by methods known in the art. These plants can then be grown, and either pollinated with the same transformed strain or different strains, where the resulting progeny have the desired phenotypic characteristic identified. Two or more generations can be grown to ensure that expression of the desired phenotypic characteristic is stably maintained and inherited, and then seeds harvested to ensure expression of the desired phenotypic characteristic has been achieved.

"Transformation event" means a product of organism or cell transformation with a heterologous DNA construct, the regeneration of a population of organisms resulting from the insertion of the recombinant DNA into the genome of the organism, and selection of a particular organism characterized by insertion of the gene construct into a particular genome location resulting in a transgenic cell of organism.

"Transformed organisms" or "transformed plants" refers to organisms or plants having integrated into their genome a nucleic acid molecule heterologous to the organisms or plants. All cells of the transformed organisms or plants may have a genetic construct integrated into their genome. A transformed plant may be a fertile plant and more particularly a plant which agronomic properties (yield, grain quality, drought tolerance, etc.) are not impaired compared to the same plant not transformed. In some embodiments, organisms or plants are transformed using *agrobacterium*-mediated transformation. Other suitable transformation methods may include, for example, particle bombardment or silicon carbide whiskers, CRISPR, TALENs, or other genome modification techniques. Genome modification techniques may alter the genome of a plant through insertion or other alteration of the plant genome. In some embodiments, a modified plant comprising a nucleic acid encoding a polypeptide as disclosed herein is contemplated.

In some embodiments, the disclosed polynucleotides encoding a polypeptide may be introduced into the genome of a plant using genome editing technologies, or previously introduced polynucleotides in the genome of a plant may be edited using genome editing technologies. For example, the disclosed polynucleotides can be introduced into a desired location in the genome of a plant through the use of double-stranded break technologies including, but not limited to, TALENS, meganucleases, zinc finger nucleases, CRISPR-Cas, and the like. The disclosed polynucleotides may be introduced into a desired location in a plant genome using a CRISPR-Cas system for the purpose of site-specific insertion. The desired location in a plant genome may be any desired target site for insertion, such as a genomic region optimized for breeding, or may be a target site located in a genomic region with an existing trait of interest. Existing traits of interest could be either an endogenous trait or a previously introduced trait.

In some embodiments, where the disclosed polynucleotide encoding the insecticidal polypeptide has previously been introduced into a genome, genome editing technologies may be used to alter or modify the introduced polynucleotide encoding the insecticidal polypeptide sequence. Alternatively, double-stranded break technologies can be used to add additional nucleotide sequences to the introduced polynucleotide. Additional sequences that may be added include additional expression elements, such as enhancer and promoter sequences. In another embodiment, genome editing technologies may be used to position additional nucleotide sequences encoding additional insecticidally-active proteins in close proximity to the disclosed polynucleotide encoding the insecticidal polypeptide disclosed herein within the genome of a plant, in order to generate molecular stacks of insecticidally-active proteins.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Treatment" or "treating" when referring to protection of a subject from a toxin, means suppressing, repressing, reversing, alleviating, ameliorating, or inhibiting the progress of damage or death due to exposure to a toxin, or completely eliminating a damage or death due to exposure to a toxin. A treatment may be either performed in an acute or chronic way. Preventing damage or death due to exposure to a toxin involves administering a composition of the present disclosure to a subject prior to exposure to a toxin. Suppressing damage or death due to exposure to a toxin involves administering a composition of the present disclosure to a subject exposure to a toxin but before the appearance of damage. Repressing or ameliorating damage or death due to exposure to a toxin involves administering a composition of the present disclosure to a subject after the appearance of damage. Treatment may be from the expression of a transgene or topical application of a polypeptide of the disclosure to a plant.

"Variant," with respect to a nucleotide or polynucleotide, means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant," with respect to a peptide, polypeptide, or protein, means differing in amino acid sequence by the insertion, deletion, or conservative substitution of amino acids, but retaining at least one biological activity. Variant may also mean a protein with an amino acid sequence that is substantially identical to a referenced protein with an amino acid sequence that retains at least one biological activity. Representative examples of "biological activity" include the ability to be bound by a specific polypeptide or to promote a specific response such as resistance or activity. Biological activity can also mean pesticidal or insecticidal activity. Variant can mean a functional fragment thereof, including functional truncated fragments and variants. Variant can also mean multiple copies of a polypeptide. The multiple copies can be in tandem or separated by a linker. A conservative substitution of an amino acid, for example, replacing an amino acid with a different amino acid of similar properties (for example, hydrophilicity, degree and distribution of charged regions) is recognized in the art as typically involving a minor change. These minor changes may be identified, in part, by considering the hydropathic index of amino acids, as understood in the art. The hydropathic index of an amino acid is based on a consideration of its hydrophobicity and charge. It is known in the art that amino acids of similar hydropathic indexes may be substituted and still retain protein function. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

In some embodiments, variant pesticidal proteins may be engineered by methods known in the art such that their sequence differs from a natural (i.e., native) or "wild-type" sequence. Protein engineering methods may be used to achieve, for example, improved pesticidal activities against specific pests (i.e., optimization) or altered target spectrum. As disclosed herein, suitable engineering methods for the generation of variant pesticidal proteins may include, but are not limited to, domain swapping, DNA shuffling, saturation mutagenesis, site-directed mutagenesis, oligonucleotide-mediated mutagenesis, cassette mutagenesis, and error-prone PCR techniques.

Variant nucleotide sequences and proteins disclosed herein encompass sequences and proteins derived from a mutagenic or recombinogenic procedure such as DNA shuffling. With such a procedure, one or more different coding sequences can be manipulated to create an engineered pesticidal protein possessing one or more desired properties. In this manner, libraries of recombinant polynucleotides can be generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence may be shuffled between nucleotide sequences encoding the pesticidal proteins described herein and other known pesticidal nucleotide sequences to obtain a new gene coding for an engineered protein having an improved property of interest, such as an increased insecticidal activity. Properties of interest may include, but are not limited to, pesticidal activity per unit of pesticidal protein, protein stability, and non-toxicity to non-target species, particularly humans, livestock, and plants and microbes that express the disclosed pesticidal proteins. DNA shuffling methods may involve only nucleotide sequences disclosed herein or may additionally involve shuffling of other nucleotide sequences known in the art. Strategies for such shuffling methods are known in the art. See, for example, Stemmer (1994) *Proc. Nat. Acad. Sci. USA* 91:10747-10751; Stemmer (1994) *Nature* 370:389-391; Crameri et al. (1997) *Nature Biotech.* 15:436-

438; Moore et al. (1997) *J. Mol. Biol.* 272:336-347; Zhang et al. (1997) *Proc. Nat. Acad. Sci. USA* 94:4504-4509; Crameri et al. (1998) *Nature* 391:288-291; and U.S. Pat. Nos. 5,605,793 and 5,837,458.

Domain swapping is another known engineering mechanism for generating variant pesticidal proteins. For example, domains may be swapped between different pesticidal polypeptides, resulting in hybrid or chimeric fusion protein toxins having altered insecticidal activity or target spectrum. Methods for generating recombinant engineered proteins and testing them for pesticidal activity are known in the art. See, for example, Naimov, et al., (2001) *Appl. Environ. Microbiol.* 67:5328-5330; de Maagd, et al., (1996) *Appl. Environ. Microbiol.* 62:1537-1543; Ge, et al., (1991) *J. Biol. Chem.* 266:17954-17958; Schnepf, et al., (1990) *J. Biol. Chem.* 265:20923-20930; and Rang, et al., 91999) *Appl. Environ. Microbiol.* 65:2918-2925.

Alternatively, variant nucleic acid sequences can be made by introducing mutations randomly along all or part of a nucleotide coding sequence, such as by saturation mutagenesis, and the resultant mutants can be screened for the ability to confer pesticidal activity to identify mutants that retain activity or have improved activity. Following mutagenesis, the encoded pesticidal protein can be expressed recombinantly, and the activity of the variant protein can be determined using standard assay techniques known in the art.

A protein of the present disclosure may be engineered to produce a different physical property, such as increased resistance or insecticidal activity to insects, altered insecticidal or resistance spectrum, or reduced plant phytotoxicity. An engineered protein may be a variant, mutant, fragment, or chimeric protein from a starting polypeptide sequence.

"Vector" as used herein means a nucleic acid sequence containing an origin of replication. A vector may be a bacterial plasmid, viral vector, bacteriophage, bacterial artificial chromosome, plant expression vector, animal expression vector, archaeal vector, or yeast artificial chromosome. A vector may be a DNA or RNA vector. A vector may be a self-replicating extrachromosomal vector, and may be a DNA plasmid. For example, the vector may encode a pesticidal protein.

Provided herein are nucleic acid molecules. A nucleic acid molecule may include a pesticidal gene polynucleotide such as that encoding any one of SEQ ID NOs: 1-184, a selectable marker gene to allow transgenic plant selection, and/or a visual reporter marker such as GFP. The nucleic acid molecule may also comprise a nucleic acid that encodes a fusion protein.

Nucleic acid molecules described herein may include, for example, polynucleotides such as vectors and plasmids. The vector may be an expression vector or system to produce protein by routine techniques and readily available starting materials. The polynucleotide may be recombinant. The polynucleotide may comprise regulatory elements for gene expression of the coding sequences of the nucleic acid. Coding sequences in the polynucleotide may be optimized for stability and high levels of expression. Regulatory elements may include a promoter, an enhancer, an initiation codon, a stop codon, and/or a polyadenylation signal.

In one aspect, the polynucleotide may encode a polypeptide having at least 70% sequence identity to any one of SEQ ID NOs: 1-184, and having pesticidal activity; the nucleic acid molecule may encode a polypeptide having at least 75% sequence identity to any one of SEQ ID NOs: 1-184, and having pesticidal activity; the nucleic acid molecule may encode a polypeptide having at least 80% sequence identity to any one of SEQ ID NOs: 1-184, and having pesticidal activity; the nucleic acid molecule may encode a polypeptide having at least 85% sequence identity to any one of SEQ ID NOs: 1-184, and having pesticidal activity; the nucleic acid molecule may encode a polypeptide having at least 90% sequence identity to any one of SEQ ID NOs: 1-184, and having pesticidal activity; the nucleic acid molecule may encode a polypeptide having at least 91% sequence identity to any one of SEQ ID NOs: 1-184, and having pesticidal activity; the nucleic acid molecule may encode a polypeptide having at least 92% sequence identity to any one of SEQ ID NOs: 1-184, and having pesticidal activity; the nucleic acid molecule may encode a polypeptide having at least 93% sequence identity to any one of SEQ ID NOs: 1-184, and having pesticidal activity; the nucleic acid molecule may encode a polypeptide having at least 94% sequence identity to any one of SEQ ID NOs: 1-184, and having pesticidal activity; the nucleic acid molecule may encode a polypeptide having at least 95% sequence identity to any one of SEQ ID NOs: 1-184, and having pesticidal activity; the nucleic acid molecule may encode a polypeptide having at least 96% sequence identity to any one of SEQ ID NOs: 1-184, and having pesticidal activity; the nucleic acid molecule may encode a polypeptide having at least 97% sequence identity to any one of SEQ ID NOs: 1-184, and having pesticidal activity; the nucleic acid molecule may encode a polypeptide having at least 98% sequence identity to any one of SEQ ID NOs: 1-184, and having pesticidal activity; the nucleic acid molecule may encode a polypeptide having at least 99% sequence identity to any one of SEQ ID NOs: 1-184, and having pesticidal activity; the nucleic acid molecule may encode a polypeptide having at least 99.2% sequence identity to any one of SEQ ID NOs: 1-184, and having pesticidal activity; the nucleic acid molecule may encode a polypeptide having at least 99.5% sequence identity to any one of SEQ ID NOs: 1-184, and having pesticidal activity; the nucleic acid molecule may encode a polypeptide having at least 99.8% sequence identity to any one of SEQ ID NOs: 1-184, and having pesticidal activity; the nucleic acid molecule may encode a polypeptide having at least 99.9% sequence identity to any one of SEQ ID NOs: 1-184, and having pesticidal activity; or, the nucleic acid molecule may encode a polypeptide having the amino acid sequence of any one of SEQ ID NOs: 1-184, and having pesticidal activity.

In one embodiment, the present disclosure is directed to an isolated polynucleotide encoding a polypeptide amino acid sequence having at least 80% or at least 95% sequence identity to any one of SEQ ID NOs: 1-184, and having pesticidal activity. The pesticidal polypeptides and polynucleotides encoding the pesticidal polypeptides of the present disclosure are particularly useful in agricultural crops for controlling and killing pests.

In one aspect, the present disclosure is directed to a method for producing a transgenic plant having pesticidal activity. The method may include transforming a plant cell with a nucleic acid molecule described herein, selecting a plant cell comprising the nucleic acid described herein, and regenerating a transgenic plant from the plant cell comprising the nucleic acid molecule described herein, wherein the transgenic plant expresses the nucleic acid molecule described herein and wherein the transgenic plant has pesticidal activity.

In one aspect, the present disclosure is directed to a method of protecting a plant from pest infestation related damage. The method may include introducing to the plant a nucleic acid molecule described herein, wherein the plant expresses the nucleic acid molecule and wherein the resulting polypeptide has pesticidal activity.

The plants or transgenic plants described herein may be protected from infection by plant pests including, but not limited to, fall armyworm (*Spodoptera frugiperda*) (FAW), corn earworm (*Helicoverpa zea*) (CEW), European corn borer (*Ostrinia nubilalis*), cotton boll worm (*Helicoverpa armigera*), black cutworm (*Agrotis ipsilon*), lesser cornstalk borer (*Elasmopalpus lignosellus*), Asian corn borer (*Ostinia furnacalis*), southwestern corn borer (*Diatraea grandiosella*), sugarcane borer (*Diatraea saccharalis*), western bean cutworm (*Striacosta albicosta*), velvetbean caterpillar (*Anticarsia gemmatalis*), western corn rootworm (*Diabrotica virgifera virgifera*), coleopteran species, lepidopteran species, hemipteran species, and combinations thereof.

In one aspect, the present disclosure is directed to a host cell comprising a nucleic acid molecule described herein. Suitable host cells may include prokaryote host cells and eukaryote host cells.

Particularly suitable prokaryote host cells may include archaea and bacteria cells. Particularly suitable eukaryote host cells may include plants and fungi. Suitable host cells may also include microbial cells such as *Trichoderma, Aspergillus, Neurospora, Humicola, Penicillium, Fusarium, Thermomonospora, Bacillus, Pseudomonas, Escherichia, Clostridium, Cellulomonas, Streptomyces, Yarrowia, Pichia* and *Saccharomyces*, and microalgal cells belonging to cyanobacterial species. Suitable plant host cells may include dicotyledons and monocotyledons. Suitable dicotyledons may include dicotyledons such as tobacco, cotton, soybean, sunflower, rapeseed, and monocotyledons such as wheat, rice, barley, sorghum, and maize.

In one aspect, the present disclosure is directed to a transgenic plant, a transgenic plant tissue, a transgenic plant cell, or a transgenic plant seed comprising a nucleic acid molecule described herein, and having pesticidal activity.

As described herein, the transformed plant cells, plant parts, or plants may have at least one nucleic acid molecule, nucleic acid construct, expression cassette or vector that encodes a polypeptide having at least 70% sequence identity to any one of SEQ ID NOs: 1-184, at least 75% sequence identity to any one of SEQ ID NOs: 1-184, at least 80% sequence identity to any one of SEQ ID NOs: 1-184, at least 85% sequence identity to any one of SEQ ID NOs: 1-184, at least 90% sequence identity to any one of SEQ ID NOs: 1-184, at least 91% sequence identity to any one of SEQ ID NOs: 1-184, at least 92% sequence identity to any one of SEQ ID NOs: 1-184, at least 93% sequence identity to any one of SEQ ID NOs: 1-184, at least 94% sequence identity to any one of SEQ ID NOs: 1-184, at least 95% sequence identity to any one of SEQ ID NOs: 1-184, at least 96% sequence identity to any one of SEQ ID NOs: 1-184, at least 97% sequence identity to any one of SEQ ID NOs: 1-184, at least 98% sequence identity to any one of SEQ ID NOs: 1-184, at least 99% sequence identity to any one of SEQ ID NOs: 1-184, at least 99.2% sequence identity to any one of SEQ ID NOs: 1-184, at least 99.5% sequence identity to any one of SEQ ID NOs: 1-184, at least 99.8% sequence identity to any one of SEQ ID NOs: 1-184, at least 99.9% sequence identity to any one of SEQ ID NOs: 1-184, or the at least one nucleic acid molecule, nucleic acid construct, expression cassette or vector may encode a polypeptide having the amino acid sequence of any one of SEQ ID NOs: 1-184, wherein the transformed plant cells, transformed plant parts, or transformed plants have pesticidal activity.

The present disclosure also relates to homologs of any of the described insecticidal proteins (e.g., SEQ ID NOs: 1-184), provided that the homologs retain insecticidal or pesticidal activity. Homolog sequences can be isolated from public or private collections and can also be prepared by various conventional methods, such as random mutagenesis, site-directed mutagenesis, gene synthesis, gene engineering, gene editing, or gene shuffling, based on all or a part of the peptide sequences presented in the present disclosure, or using all or part of their coding nucleotide sequences. Such homologs include, for example, deletions, insertions, or substitutions of one or more residues in the amino acid sequence of the protein, or a combination thereof. In some embodiments, a homolog may include a protein having at least 70% sequence identity, at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, at least 99% sequence identity, at least 99.2% sequence identity, at least 99.5% sequence identity, at least 99.8% sequence identity, or at least 99.9% sequence identity to any one of SEQ ID NOs: 1-184.

In some aspects of the present disclosure, a polynucleotide sequence encoding a shuffled insecticidal toxin polypeptide including amino acid substitutions, deletions, insertions, and fragments thereof is disclosed. An insecticidal toxin may have one or more of several domains swapped or shuffled to alter a physical property of the toxin, such as increased efficacy, altered spectrum, reduced plant phytotoxicity, etc.

Pesticidal proteins may be derived from *Bacillus thuringiensis* ("Bt"), a Gram-positive spore forming soil bacterium. Current commercial pesticidal proteins include Bt Cry (crystal protein), as well as many active insecticidal proteins that lack commercial efficacy, spectrum, or stability. The disclosed embodiments solve some efficacy, spectrum, and/or stability issues in pesticidal protein families of Bt derived insecticidal proteins (see Crickmore, et al., "*Bacillus thuringiensis* toxin nomenclature" (2011) and Crickmore et al., "A structure-based nomenclature for *Bacillus thuringiensis* and other bacteria-derived pesticidal proteins" (2021), at bpprc.org).

In addition to the full-length nucleotide sequence of a nucleic acid molecule encoding a polypeptide of any one of SEQ ID NOs: 1-184, the nucleic acid molecule encoding any one of SEQ ID NOs: 1-184 may include a fragment or variant thereof that encodes a polypeptide capable of pesticidal activity. For nucleotide sequences, "fragment" as used herein means a portion of a nucleotide sequence of a nucleic acid molecule, for example, a portion of the nucleotide sequence encoding any one of SEQ ID NOs: 1-184. Fragments of a nucleotide sequence may retain the biological activity of the reference nucleic acid molecule. For example, a nucleic acid molecule encoding less than the entire amino acid sequence disclosed in any one of SEQ ID NOs: 1-184 may be used to encode a protein that retains its pesticidal activity. In other embodiments, fragments of any one of SEQ ID NOs: 1-184 may be used to alter biologically activity of another insecticidal polypeptide sequence or non-insecticidal polypeptide sequence through addition, swapping, or mutating the other insecticidal or non-insecticidal polypeptide with fragments of any one of SEQ ID NOs: 1-184. Alternatively, fragments of a nucleotide sequence can be used as hybridization probes or as an amplification primer. Fragments used as hybridization probes or primers generally do not need to retain biological activity. Thus, fragments of the nucleic acid molecules can be at least about 10, 15, 20, 25, 50, 75, 100, 125, 150, 175, 200, 250, 300, 350, 400, 450, 500, 550, 600, 650, 700, 750, 800, 850 or 900 nucleotides, or up to the number of nucleotides present in a full-length nucleic acid molecule. A biologically active portion (fragment or variant) of the nucleic acid molecule can be prepared by isolating part of the sequence of the nucleic acid molecule, operably linking that fragment to a promoter, expressing the nucleotide sequence encoding the protein, and assessing the amount or activity of the protein.

In some embodiments, the nucleotide sequence or nucleic acid molecule encoding the polypeptide of any one of SEQ ID NOs: 1-184 can also be stacked with nucleotide sequences encoding for agronomic traits such as male sterility, stalk strength, flowering time, other insecticidal proteins, RNA interference transgenes, or transformation technology traits such as cell cycle regulation or gene targeting. These stacked combinations can be created by any method including cross breeding plants by any conventional or TopCross™ methodology, zinc finger nucleases (ZFNs), transcription activator-like effector nucleases (TALENs), clustered regularly interspaced short palindromic repeats (CRISPR), and other genetic transformation or editing. If the traits are stacked by genetically transforming the plants, the nucleotide sequences of interest can be combined at any time and in any order. For example, a transformed plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate expression cassettes (trans) or contained on the same transformation cassette (cis). Expression of the sequences can be driven by the same promoter or by different promoters.

In one aspect, the present disclosure is directed to a vector that may comprise a nucleic acid molecule encoding a polypeptide having at least 70% sequence identity to any one of SEQ ID NOs: 1-184, at least 75% sequence identity to any one of SEQ ID NOs: 1-184, at least 80% sequence identity to any one of SEQ ID NOs: 1-184, at least 85% sequence identity to any one of SEQ ID NOs: 1-184, at least 90% sequence identity to any one of SEQ ID NOs: 1-184, at least 91% sequence identity to any one of SEQ ID NOs: 1-184, at least 92% sequence identity to any one of SEQ ID NOs: 1-184, at least 93% sequence identity to any one of SEQ ID NOs: 1-184, at least 94% sequence identity to any one of SEQ ID NOs: 1-184, at least 95% sequence identity to any one of SEQ ID NOs: 1-184, at least 96% sequence identity to any one of SEQ ID NOs: 1-184, at least 97% sequence identity to any one of SEQ ID NOs: 1-184, at least 98% sequence identity to any one of SEQ ID NOs: 1-184, at least 99% sequence identity to any one of SEQ ID NOs: 1-184, at least 99.2% sequence identity to any one of SEQ ID NOs: 1-184, at least 99.5% sequence identity to any one of SEQ ID NOs: 1-184, at least 99.8% sequence identity to any one of SEQ ID NOs: 1-184, or at least 99.9% sequence identity to any one of SEQ ID NOs: 1-184.

Suitable vectors are known in the art. Particularly suitable vectors include antibiotic resistance or thermostable antibiotic resistance, or coding for an enzyme that can complement an auxotrophy (natural, such as overcoming the absence of an indispensable amino acid, or engineered, such as URA3-deficient mutants where URA3 is necessary for uracil biosynthesis). Selectable markers include those conferring resistance to antibiotics such as kanamycin (nptII gene), hygromycin (aph IV) spectinomycin (aadA) and gentamycin (aac3 and aacC4) or resistance to herbicides such as glufosinate (bar or pat), dicamba (DMO) and glyphosate (aroA or EPSPS). Selectable markers that allow a direct visual identification of transformation events can also be employed, for example, genes expressing a colored or fluorescent protein such as a luciferase or green fluorescent protein (GFP) or a gene expressing a betaglucuronidase or uidA gene (GUS) for which various chromogenic substrates are known.

In one aspect, the present disclosure is directed to a formulation that may include a recombinant polypeptide having at least 70% sequence identity to any one of SEQ ID NOs: 1-184, at least 75% sequence identity to any one of SEQ ID NOs: 1-184, at least 80% sequence identity to any one of SEQ ID NOs: 1-184, at least 85% sequence identity to any one of SEQ ID NOs: 1-184, at least 90% sequence identity to any one of SEQ ID NOs: 1-184, at least 91% sequence identity to any one of SEQ ID NOs: 1-184, at least 92% sequence identity to any one of SEQ ID NOs: 1-184, at least 93% sequence identity to any one of SEQ ID NOs: 1-184, at least 94% sequence identity to any one of SEQ ID NOs: 1-184, at least 95% sequence identity to any one of SEQ ID NOs: 1-184, at least 96% sequence identity to any one of SEQ ID NOs: 1-184, at least 97% sequence identity to any one of SEQ ID NOs: 1-184, at least 98% sequence identity to any one of SEQ ID NOs: 1-184, at least 99% sequence identity to any one of SEQ ID NOs: 1-184, at least 99.2% sequence identity to any one of SEQ ID NOs: 1-184, at least 99.5% sequence identity to any one of SEQ ID NOs: 1-184, at least 99.8% sequence identity to any one of SEQ ID NOs: 1-184, or at least 99.9% sequence identity to any one of SEQ ID NOs: 1-184, and having pesticidal activity. When applied to a plant, the recombinant polypeptide exhibits pesticidal activity.

Formulations of recombinant polypeptide comprising an acceptable carrier may be in the form of a suspension, a solution, an emulsion, a dusting powder, a dispersible granule, a wettable powder, an emulsifiable concentrate, an aerosol, an impregnated granule, an adjuvant, a coatable paste, encapsulations, or combinations thereof.

Formulations of recombinant polypeptide may include surface-active agents, inert carriers, preservatives, humectants, feeding stimulants, attractants, encapsulating agents, binders, emulsifiers, dyes, UV protectants, buffers, flow agents, fertilizers, solvents, dispersants, wetting agents, tackifiers, micronutrient donors, and combinations thereof.

In one aspect, the present disclosure is directed to a formulation that may include a transformed bacteria comprising a nucleic acid molecule as described herein, and having pesticidal activity. When applied to a plant, the transformed bacteria of the formulation express the nucleic acid molecule and the polypeptide exhibits pesticidal activity.

Formulations of transformed bacteria comprising an acceptable carrier may be in the form of a suspension, a solution, an emulsion, a dusting powder, a dispersible granule, a wettable powder, an emulsifiable concentrate, an aerosol, an impregnated granule, an adjuvant, a coatable paste, encapsulations, or combinations thereof.

Formulations of transformed bacteria may include surface-active agents, inert carriers, preservatives, humectants, feeding stimulants, attractants, encapsulating agents, binders, emulsifiers, dyes, UV protectants, buffers, flow agents, fertilizers, solvents, dispersants, wetting agents, tackifiers, micronutrient donors, and combinations thereof.

Transformed bacteria comprising a nucleic acid molecule as described herein may be used in the same manner that *Bacillus thuringiensis* strains have previously been used as insecticidal sprays.

The biological activity of interest of the formulations comprising recombinant polypeptide or transformed bacteria is the control of damage-causing plant pests. Such biological activity can be assayed by applying an effective amount of either formulation to a plant having a plant pest, or at risk of being infested by a plant pest, and determining whether the formulation controls the damage-causing plant pests.

In one aspect, the present disclosure is directed to a method for protecting a plant from an insect pest. The method may include expressing in a plant, or a plant cell thereof, a nucleic acid molecule as described herein, wherein the nucleic acid molecule encoding the polypeptide is operably linked to a promoter capable of driving expression in the plant or plant cell thereof, and wherein the encoded polypeptide has pesticidal activity against the insect pest.

Some aspects described herein also encompass antibodies that specifically bind to a chimeric insecticidal protein of the present disclosure. The antibody can optionally be a monoclonal antibody or a polyclonal antisera. In some embodiments, an antibody is selective for the chimeric protein and does not bind to one or more of the parent molecules, and can be used to distinguish the chimeric protein from the parent protein. Such antibodies may be produced using standard immunological techniques for production of polyclonal antisera and, if desired, immortalizing the antibody-producing cells of the immunized host for sources of monoclonal antibody production. The present disclosure also encompasses an insecticidal protein that cross-reacts with an antibody, particularly a monoclonal antibody, raised against one or more of the chimeric insecticidal proteins disclosed herein.

The following experimental examples are offered by way of illustration and not by way of limitation.

EXAMPLES

Example 1

A novel sequence from *Myxococcus fulvus* (GUN2873.1.2; SEQ ID NO: 1 as disclosed herein) was found to have insecticidal activity against corn rootworm, *Diabrotica virgifera* (CRW). Further strategic engineering methods were used to create novel insecticidal engineered variants (SEQ ID NO: 2-184) with increased insecticidal activity, altered spectrum of insecticidal activity, or increased stability.

Example 2

To express the insecticidal polypeptides, the DNA gene coding sequence was synthesized as optimized for expression in *E. coli*. This sequence was cloned into the pHis Expression Vector (modified version of pRSF-1b (Novagen)), thus fusing an N-terminal 6×-His TAG coding sequence to the gene. The clone was transformed into *E. coli* strain BL21(DE3) and grown in an auto-induction medium (OVERNIGHT EXPRESS™ LB medium, EMD Millipore). Following induction, bacterial cells were harvested for recombinant protein purification prior to conducting insect larval activity assays. In some cases, the bacterial culture following induction was used for insect assays.

Example 3

Insecticidal toxicity bioassays were conducted with transformed bacterial whole cells expressing proteins to evaluate pesticidal efficacy against pests including armyworms, *Spodoptera* spp, corn earworm, *Helicoverpa* spp, corn borer, *Ostrinia* spp, *Diatraea* spp, *Anticarsia* spp, and *Diabrotica* spp.

Corn rootworm, *Diabrotica virgifera* (CRW), northern corn rootworm, *Diabrotica barberi* (NCR), and southern corn rootworm, *Diabrotica undecimpunctata howardi* (SCR) eggs were obtained. Bioassay methods similar to those described by Huynh et al. (2017) and Ludwick et al. (2018) were used to detect insecticidal efficacy. Following incubation, mortality, growth inhibition, and feeding inhibition were assessed (Table 1).

Fall armyworm, *Spodoptera frugiperda* (FAW), corn earworm, *Helicoverpa zea* (CEW), European corn borer, *Ostrinia nubilalis* (ECB), velvetbean caterpillar, *Anticarsia*

*gemmatalis* (VBC), southwestern corn borer, *Diatraea grandiosella* (SWCB), sugarcane borer, *Diatraea saccharalis* (SCB), soybean looper, *Chrysodeixis includens* (SBL), beet armyworm, *Spodoptera exigua* (BAW), southern armyworm, *Spodoptera eridania* (SAW), tobacco budworm, *Chloridia virescens* (TBW), western corn rootworm, *Diabrotica virgifera virgifera* (WCR), and black cutworm, *Agrotis ipsilon* (BCW) eggs were obtained from a commercial insectary (Benzon Research Inc., Carlisle, PA). Eggs were incubated under controlled temperature and humidity until eclosion. Bioassay methods similar to those described by Wang et al. (2019) were used to detect insecticidal efficacy. Following 5 days of incubation, mortality, growth inhibition, and feeding inhibition were assessed (Table 1). While some proteins did not exhibit significant insecticidal activity as tested using this specific diet-overlay bioassay format, other experimental test conditions or bioassays may result in insecticidal activity being measured for those proteins.

TABLE 1

Measured insecticidal activity of whole recombinant
E. coli culture expressing insecticidal proteins.

| Insecticidal Protein | Insecticidal Activities in Diet-Overlay Bioassay | | | | | | |
| --- | --- | --- | --- | --- | --- | --- | --- |
| | FAW | CEW | SCB | WCR | NCR | Cry34/35 R-WCR | Cry3Bb R-WCR |
| SEQ ID NO: 1 | – | – | – | + | + | + | + |
| SEQ ID NO: 2 | – | – | – | – | NT | NT | NT |
| SEQ ID NO: 3 | + | – | + | – | NT | NT | NT |
| SEQ ID NO: 4 | – | – | – | – | NT | NT | NT |
| SEQ ID NO: 5 | – | – | – | – | NT | NT | NT |
| SEQ ID NO: 6 | + | – | + | – | NT | NT | NT |
| SEQ ID NO: 7 | – | – | – | – | NT | NT | NT |
| SEQ ID NO: 8 | – | – | – | – | NT | NT | NT |
| SEQ ID NO: 9 | – | – | – | – | NT | NT | NT |
| SEQ ID NO: 10 | – | – | – | – | NT | NT | NT |
| SEQ ID NO: 11 | – | – | – | – | NT | NT | NT |
| SEQ ID NO: 12 | – | – | – | + | NT | NT | NT |
| SEQ ID NO: 13 | – | – | – | – | NT | NT | NT |
| SEQ ID NO: 14 | – | + | – | – | NT | NT | NT |
| SEQ ID NO: 15 | – | – | – | – | NT | NT | NT |
| SEQ ID NO: 16 | – | – | – | – | NT | NT | NT |
| SEQ ID NO: 17 | – | – | – | – | NT | NT | NT |
| SEQ ID NO: 18 | – | – | – | – | NT | NT | NT |
| SEQ ID NO: 19 | – | – | – | + | NT | NT | NT |
| SEQ ID NO: 20 | – | – | – | + | NT | NT | NT |
| SEQ ID NO: 21 | + | – | – | – | NT | NT | NT |
| SEQ ID NO: 22 | – | – | – | – | NT | NT | NT |
| SEQ ID NO: 23 | – | – | – | – | NT | NT | NT |
| SEQ ID NO: 24 | – | – | – | + | NT | NT | NT |
| SEQ ID NO: 25 | – | – | – | – | NT | NT | NT |
| SEQ ID NO: 26 | – | – | – | – | NT | NT | NT |
| SEQ ID NO: 27 | – | – | – | – | NT | NT | NT |
| SEQ ID NO: 28 | – | – | – | – | NT | NT | NT |
| SEQ ID NO: 29 | – | – | – | – | NT | NT | NT |
| SEQ ID NO: 30 | – | – | – | + | NT | NT | NT |
| SEQ ID NO: 31 | – | – | – | – | NT | NT | NT |
| SEQ ID NO: 32 | – | – | + | – | NT | NT | NT |
| SEQ ID NO: 33 | – | – | – | – | NT | NT | NT |
| SEQ ID NO: 34 | – | – | – | – | NT | NT | NT |
| SEQ ID NO: 35 | – | – | – | – | NT | NT | NT |
| SEQ ID NO: 36 | – | – | – | – | NT | NT | NT |
| SEQ ID NO: 37 | – | – | – | – | NT | NT | NT |
| SEQ ID NO: 38 | – | – | – | – | NT | NT | NT |
| SEQ ID NO: 39 | – | – | – | – | NT | NT | NT |
| SEQ ID NO: 40 | – | – | – | – | NT | NT | NT |
| SEQ ID NO: 41 | – | – | – | – | NT | NT | NT |
| SEQ ID NO: 42 | – | – | – | + | NT | NT | NT |
| SEQ ID NO: 43 | – | – | – | – | NT | NT | NT |
| SEQ ID NO: 44 | – | – | – | – | NT | NT | NT |
| SEQ ID NO: 45 | – | – | – | + | NT | NT | NT |
| SEQ ID NO: 46 | – | – | – | + | NT | NT | NT |

TABLE 1-continued

Measured insecticidal activity of whole recombinant
E. coli culture expressing insecticidal proteins.

| | Insecticidal Activities in Diet-Overlay Bioassay | | | | | | |
|---|---|---|---|---|---|---|---|
| Insecticidal Protein | FAW | CEW | SCB | WCR | NCR | Cry34/35 R-WCR | Cry3Bb R-WCR |
| SEQ ID NO: 47 | – | – | – | – | NT | NT | NT |
| SEQ ID NO: 48 | – | – | – | – | NT | NT | NT |
| SEQ ID NO: 49 | – | – | – | – | NT | NT | NT |
| SEQ ID NO: 50 | – | – | – | + | NT | NT | NT |
| SEQ ID NO: 51 | – | – | – | – | NT | NT | NT |
| SEQ ID NO: 52 | – | – | – | – | NT | NT | NT |
| SEQ ID NO: 53 | – | – | – | – | NT | NT | NT |
| SEQ ID NO: 54 | – | – | – | – | NT | NT | NT |
| SEQ ID NO: 55 | – | – | – | + | NT | NT | NT |
| SEQ ID NO: 56 | – | – | – | – | NT | NT | NT |
| SEQ ID NO: 57 | – | – | – | + | NT | NT | NT |
| SEQ ID NO: 58 | – | – | – | – | NT | NT | NT |
| SEQ ID NO: 59 | – | – | – | – | NT | NT | NT |
| SEQ ID NO: 60 | – | – | – | – | NT | NT | NT |
| SEQ ID NO: 61 | – | – | – | – | NT | NT | NT |
| SEQ ID NO: 62 | – | – | – | + | NT | NT | NT |
| SEQ ID NO: 63 | – | – | – | – | NT | NT | NT |
| SEQ ID NO: 64 | – | – | – | – | NT | NT | NT |
| SEQ ID NO: 65 | – | – | – | – | NT | NT | NT |
| SEQ ID NO: 66 | – | – | – | – | NT | NT | NT |
| SEQ ID NO: 67 | – | – | – | – | NT | NT | NT |
| SEQ ID NO: 68 | – | – | – | – | NT | NT | NT |
| SEQ ID NO: 69 | – | – | – | – | NT | NT | NT |
| SEQ ID NO: 70 | – | – | – | – | NT | NT | NT |
| SEQ ID NO: 71 | – | – | – | – | NT | NT | NT |
| SEQ ID NO: 72 | – | – | – | – | NT | NT | NT |
| SEQ ID NO: 73 | – | – | – | – | NT | NT | NT |
| SEQ ID NO: 74 | – | – | – | + | NT | NT | NT |
| SEQ ID NO: 75 | – | – | – | – | NT | NT | NT |
| SEQ ID NO: 76 | – | – | – | – | NT | NT | NT |
| SEQ ID NO: 77 | – | – | – | – | NT | NT | NT |
| SEQ ID NO: 78 | – | – | – | – | NT | NT | NT |
| SEQ ID NO: 79 | – | – | – | – | NT | NT | NT |
| SEQ ID NO: 80 | – | – | – | – | NT | NT | NT |
| SEQ ID NO: 81 | – | – | – | – | NT | NT | NT |
| SEQ ID NO: 82 | – | – | – | – | NT | NT | NT |
| SEQ ID NO: 83 | – | – | – | -- | NT | NT | NT |
| SEQ ID NO: 84 | – | – | – | – | NT | NT | NT |
| SEQ ID NO: 85 | – | – | – | – | NT | NT | NT |
| SEQ ID NO: 86 | – | – | – | + | NT | NT | NT |
| SEQ ID NO: 87 | – | – | – | + | NT | NT | NT |
| SEQ ID NO: 88 | – | – | – | + | NT | NT | NT |
| SEQ ID NO: 89 | – | – | – | – | NT | NT | NT |
| SEQ ID NO: 90 | – | – | – | + | NT | NT | NT |
| SEQ ID NO: 91 | – | – | – | + | NT | NT | NT |
| SEQ ID NO: 92 | – | – | – | + | NT | NT | NT |
| SEQ ID NO: 93 | – | – | – | + | NT | NT | NT |
| SEQ ID NO: 94 | – | – | – | – | NT | NT | NT |
| SEQ ID NO: 95 | – | – | – | + | NT | NT | NT |
| SEQ ID NO: 96 | – | – | – | + | NT | NT | NT |
| SEQ ID NO: 97 | – | – | – | – | NT | NT | NT |
| SEQ ID NO: 98 | – | – | – | + | NT | NT | NT |
| SEQ ID NO: 99 | – | – | – | – | NT | NT | NT |
| SEQ ID NO: 100 | – | – | – | + | NT | NT | NT |
| SEQ ID NO: 101 | – | – | – | – | NT | NT | NT |
| SEQ ID NO: 102 | – | – | – | + | NT | NT | NT |
| SEQ ID NO: 103 | – | – | – | – | NT | NT | NT |
| SEQ ID NO: 104 | – | – | – | – | NT | NT | NT |
| SEQ ID NO: 105 | – | – | – | – | NT | NT | NT |
| SEQ ID NO: 106 | – | – | – | – | NT | NT | NT |
| SEQ ID NO: 107 | – | – | – | + | NT | NT | NT |
| SEQ ID NO: 108 | – | – | – | + | NT | NT | NT |
| SEQ ID NO: 109 | – | – | – | – | NT | NT | NT |
| SEQ ID NO: 110 | – | – | – | + | NT | NT | NT |
| SEQ ID NO: 111 | – | – | – | – | NT | NT | NT |
| SEQ ID NO: 112 | – | – | – | + | NT | NT | NT |
| SEQ ID NO: 113 | – | – | – | + | NT | NT | NT |
| SEQ ID NO: 114 | – | – | – | + | NT | NT | NT |
| SEQ ID NO: 115 | – | – | – | + | NT | NT | NT |
| SEQ ID NO: 116 | – | – | – | + | NT | NT | NT |
| SEQ ID NO: 117 | – | – | – | + | NT | NT | NT |

TABLE 1-continued

Measured insecticidal activity of whole recombinant
E. coli culture expressing insecticidal proteins.

| Insecticidal Protein | Insecticidal Activities in Diet-Overlay Bioassay | | | | | | |
|---|---|---|---|---|---|---|---|
| | FAW | CEW | SCB | WCR | NCR | Cry34/35 R-WCR | Cry3Bb R-WCR |
| SEQ ID NO: 118 | – | – | – | + | NT | NT | NT |
| SEQ ID NO: 119 | – | – | – | + | NT | NT | NT |
| SEQ ID NO: 120 | – | – | – | – | NT | NT | NT |
| SEQ ID NO: 121 | – | – | – | + | NT | NT | NT |
| SEQ ID NO: 122 | – | – | – | + | NT | NT | NT |
| SEQ ID NO: 123 | – | – | – | – | NT | NT | NT |
| SEQ ID NO: 124 | – | – | – | + | NT | NT | NT |
| SEQ ID NO: 125 | – | – | – | + | NT | NT | NT |
| SEQ ID NO: 126 | – | – | – | + | NT | NT | NT |
| SEQ ID NO: 127 | – | – | – | + | NT | NT | NT |
| SEQ ID NO: 128 | – | – | – | + | NT | NT | NT |
| SEQ ID NO: 129 | – | – | – | + | NT | NT | NT |
| SEQ ID NO: 130 | – | – | – | + | NT | NT | NT |
| SEQ ID NO: 131 | – | – | – | + | NT | NT | NT |
| SEQ ID NO: 132 | – | – | – | + | NT | NT | NT |
| SEQ ID NO: 133 | – | – | – | + | NT | NT | NT |
| SEQ ID NO: 134 | – | – | – | + | NT | NT | NT |
| SEQ ID NO: 135 | – | – | – | + | NT | NT | NT |
| SEQ ID NO: 136 | – | – | – | + | NT | NT | NT |
| SEQ ID NO: 137 | – | – | – | + | NT | NT | NT |
| SEQ ID NO: 138 | – | – | – | + | NT | NT | NT |
| SEQ ID NO: 139 | – | – | – | + | NT | NT | NT |
| SEQ ID NO: 140 | – | – | – | + | NT | NT | NT |
| SEQ ID NO: 141 | – | – | – | + | NT | NT | NT |
| SEQ ID NO: 142 | – | – | – | + | NT | NT | NT |
| SEQ ID NO: 143 | – | – | – | + | NT | NT | NT |
| SEQ ID NO: 144 | – | – | – | + | NT | NT | NT |
| SEQ ID NO: 145 | – | – | – | – | NT | NT | NT |
| SEQ ID NO: 146 | – | – | – | + | NT | NT | NT |
| SEQ ID NO: 147 | – | – | – | + | NT | NT | NT |
| SEQ ID NO: 148 | – | – | – | – | NT | NT | NT |
| SEQ ID NO: 149 | – | – | – | + | NT | NT | NT |
| SEQ ID NO: 150 | – | – | – | – | NT | NT | NT |
| SEQ ID NO: 151 | – | – | – | + | NT | NT | NT |
| SEQ ID NO: 152 | – | – | – | + | NT | NT | NT |
| SEQ ID NO: 153 | – | – | – | + | NT | NT | NT |
| SEQ ID NO: 154 | – | – | – | + | NT | NT | NT |
| SEQ ID NO: 155 | – | – | – | + | NT | NT | NT |
| SEQ ID NO: 156 | – | – | – | + | NT | NT | NT |
| SEQ ID NO: 157 | – | – | – | + | NT | NT | NT |
| SEQ ID NO: 158 | – | – | – | + | NT | NT | NT |
| SEQ ID NO: 159 | – | – | – | + | NT | NT | NT |
| SEQ ID NO: 160 | – | – | – | – | NT | NT | NT |
| SEQ ID NO: 161 | – | – | – | – | NT | NT | NT |
| SEQ ID NO: 162 | – | – | + | + | NT | NT | NT |
| SEQ ID NO: 163 | – | – | – | – | NT | NT | NT |
| SEQ ID NO: 164 | – | – | – | – | NT | NT | NT |
| SEQ ID NO: 165 | – | – | – | – | NT | NT | NT |
| SEQ ID NO: 166 | – | – | + | + | NT | NT | NT |
| SEQ ID NO: 167 | – | – | – | – | NT | NT | NT |
| SEQ ID NO: 168 | – | – | – | NT | NT | NT | NT |
| SEQ ID NO: 169 | – | – | – | NT | NT | NT | NT |
| SEQ ID NO: 170 | – | – | – | NT | NT | NT | NT |
| SEQ ID NO: 171 | – | – | – | NT | NT | NT | NT |
| SEQ ID NO: 172 | – | – | – | NT | NT | NT | NT |
| SEQ ID NO: 173 | – | – | – | NT | NT | NT | NT |
| SEQ ID NO: 174 | – | – | – | NT | NT | NT | NT |
| SEQ ID NO: 175 | – | – | – | NT | NT | NT | NT |
| SEQ ID NO: 176 | – | – | – | NT | NT | NT | NT |
| SEQ ID NO: 177 | – | – | – | NT | NT | NT | NT |
| SEQ ID NO: 178 | – | – | – | NT | NT | NT | NT |
| SEQ ID NO: 179 | – | – | – | NT | NT | NT | NT |
| SEQ ID NO: 180 | – | – | – | NT | NT | NT | NT |
| SEQ ID NO: 181 | – | – | – | NT | NT | NT | NT |
| SEQ ID NO: 182 | – | – | – | NT | NT | NT | NT |
| SEQ ID NO: 183 | – | – | – | NT | NT | NT | NT |
| SEQ ID NO: 184 | – | – | – | NT | NT | NT | NT |

(+)—indicates that insecticidal activity was measured
(–)—indicates that no insecticidal activity was measured
NT—indicates a condition that was not tested

Example 4

*Agrobacterium*-mediated transient expression in *Nicotiana benthamiana* was used to identify insecticidal activity in planta (Kapila et al. 1997; Schob et al., 1997). Leaf disks constitutively expressing the gene using different expression vector constructs were assayed for reduced feeding damage against Cry1Fa-rFAW, Vip3A-rFAW, sFAW, CEW, ECB, SBL, BCW, SAW, TBW, BAW, WCRW, SCR, and cabbage looper, *Trichoplusia ni* (CL) (Table 2).

TABLE 2

Measured insecticidal activity of leaf disks expressing insecticidal proteins.

| Insecticidal Protein | Leaf Disk Protection SCR | Phytotoxicity | |
|---|---|---|---|
| | | Early Tox (after 3 days) | Late Tox (after 6 days) |
| CyclA2 | NT | Y | Y |
| Cry1Fa | NT | N | N |
| ZsGreen | – | NT | NT |
| GUN0040A | + | N | N |
| Untransformed | – | NT | NT |
| SEQ ID NO: 1 Expression Vector 1 | + | N | Y |
| SEQ ID NO: 1 | – | N | N |
| SEQ ID NO: 1 v2 | – | N | N |
| SEQ ID NO: 1 v2 Expression Vector 1 | + | N | N |
| SEQ ID NO: 1 v2 Expression Vector 2 | + | N | N |
| SEQ ID NO: 1 v2 Expression Vector 3 | – | N | N |

(+)—indicates that insecticidal activity was measured
(–)—indicates that no insecticidal activity was measured
Y—indicates that phytotoxicity was observed after 3 days (Early Tox) or 6 days (Late Tox)
N—indicates that phytotoxicity was not observed
NT—indicates a condition that was not tested
SEQ ID NO: 1 v2—alternative expression construct tested

Example 5

In this example, different plant binary nucleic acid experimental constructs are produced using various promoters, initiators, introns, enhancers, terminators, upstream regulatory constructs, downstream regulatory constructs, or other regulatory sequence elements that are operably linked to drive expression of a nucleotide sequence encoding any of the pesticidal proteins disclosed herein in a target plant, such as maize cells.

In some examples, these nucleic acid experimental constructs are operably linked to sequences encoding specific targeting peptides, such as a *Zea mays* chloroplast targeting signal peptide.

Each of the experimental constructs are individually transformed into the maize inbred B104. A minimum of 10 individual, single copy transformation events with intact T-DNAs are produced for each construct. qRT-PCR and western blot analyses are performed on TO leaf material to select transgenic plants showing pesticidal protein expression.

The selected transgenic plants and their progenies from the experimental constructs are grown in greenhouse conditions. Pesticidal activity and efficacy of the different transgenic plants are then evaluated against various pests.

Fall armyworm, *Spodoptera frugiperda* (FAW) insecticidal efficacy is tested in the greenhouse conditions using a method of artificial infestation of neonate (newly hatched larvae in the $1^{st}$ larval stage) FAW larvae onto the whorl leaves of the plant and then rating the leaves after the larvae have fed. FAW efficacy assays are deployed in a randomized complete block design of 4 replications of 3 infested plants. Negative (non-transgenic) and positive (transgenic plants expressing reference toxins) controls are utilized as comparators in the root damage assessment. Seeds are counted out and planted in 18 cell flats and placed in a greenhouse bay for germination. The greenhouse bays are set for corn growth with day temperature set to 26-29° C. at 50% RH, and night temperature set to 17-20° C. at 50% RH. The light to dark ratio is 16:8. The seedlings are transplanted into 1-gallon pots at V2 (approximately 14 days). The plants are allowed to grow to V5/V6 growth stage and then each plant is infested with 30 neonate larvae. The neonate larvae are infested in the maize whorl using an inoculator that delivers a 1 mL aliquot of 2040 corn cob grits (used as a carrier) mixed with neonate larvae. Once infested, the larvae feed on the plants for 14 days. When the plants are deemed ready to rate, the Davis Scale for FAW damage is used to select efficacious plants. Analysis of variance (JMP®) is run comparing the transgenic events to the appropriate controls.

Corn earworm, *Helicoverpa zea* (CEW) insecticidal efficacy is tested in the greenhouse conditions using a method of artificial infestation of neonate CEW (newly hatched larvae in the $1^{st}$ larval stage) at VT (a few days after each plant is hand pollinated) on the top of the ear in the pollinated silks. CEW efficacy assays are deployed in a randomized complete block design of 4 replications and 3 infested plants. Negative (non-transgenic) and positive (transgenic plants expressing reference toxins) controls are utilized as comparators in the ear damage assessment. Seeds are counted out and planted in 18 cell flats and placed in a greenhouse bay for germination. The greenhouse bays are set for corn growth with day temperature set to 26-29° C. at 50% RH, and night temperature set to 17-20° C. at 50% RH. The light to dark ratio is 16:8. The seedlings are transplanted into 3-gallon pots at V2 (approximately 14 days). After hand pollination, each ear is infested on the pollinated silks with 15 neonate larvae. Once infested, the larvae feed for 21 days. When the ears are deemed ready to rate, each ear is husked back and ear damage is measured in $cm^2$ per ear and efficacious plants are selected. Analysis of variance (JMP®) is run comparing the transgenic events to the appropriate controls.

Corn rootworm, *Diabrotica virgifera* (CRW) insecticidal efficacy is tested in the greenhouse conditions using a method of artificial infestation of eggs into the plant and then rating the roots after the eggs have hatched and the larvae have fed. CRW efficacy assays are deployed in a randomized complete block design of 4 replicates of 3 infested plants. Negative (non-transgenic) and positive (transgenic plants expressing reference toxins) controls are utilized as comparators in the root damage assessment. Seeds are counted out and planted into 32 cell flats and placed in a greenhouse bay for germination. The greenhouse bays are set for corn growth with day temperature set to 26-29° C. at 50% RH, and night temperature set to 17-20° C. at 50% RH. The light to dark ratio is 16:8. The seedlings are transplanted into 1-gallon pots at V2 (approximately 14 days). The plants are allowed to acclimate for approximately 2 days and then are infested with CRW eggs. The eggs are delivered in a 0.16% agar solution at a rate of 500 eggs per mL. Each plant receives 2 mL of egg/agar solution. The solution is delivered in a 1 mL aliquot through a syringe or repeater pipette into each of 2 holes on either side of the plant, approximately 2 inches from the base of the plant and 2 inches deep. The eggs hatch after infestation in approximately 12 days. Once hatched, the larvae feed for approximately 17-21 days. Plants are checked throughout the feeding cycle to monitor feeding progress and proper time to rate. When the plants are determined to be ready, the plants are removed from the greenhouse and washed and rated in a root processing area of the greenhouse complex. The roots are rated using the Iowa State NIS corn injury scale. Analysis of variance (JMP®) is run comparing the transgenic events to the appropriate controls.

European corn borer, *Ostrinia nubilalis* (ECB) insecticidal efficacy is tested in the greenhouse using a method of artificial infestation of neonate ECB (newly hatched larvae in the 1$^{st}$ larval stage) at VT/R1 above primary ear and below the secondary ear and then rating the internal stalk and ear shank damage after the larvae have fed. ECB efficacy assays are deployed in a randomized complete block design of 4 replications of 3 infested plants. Negative (non-transgenic) and positive (transgenic plants expressing reference toxins) controls are utilized as comparators in stalk and ear shank damage assessment. Seeds are counted out and planted in 18 cell flats and placed in a greenhouse bay for germination. The greenhouse bays are set for corn growth with day temperature set to 26-29° C. at 50% RH, and night temperature set to 17-20° C. at 50% RH. The light to dark ratio is 16:8. The seedlings are transplanted into 3-gallon pots at V2 (approximately 14 days). The plants are allowed to grow to VT/R1 growth stage and then each plant is infested one node above the primary ear and one node below the secondary ear with 50 neonate larvae (100 neonate larvae total). The neonate larvae are infested at the proper nodes where the leaf meets the stalk using an inoculator that delivers a 1 mL aliquot of 2040 corn cob grits (used as a carrier) mixed with neonate larvae. Once infested, the larvae feed for 45-60 days. When the plants are deemed ready to rate, each stalk and ear shank is split and the internal damage is measured in cm and efficacious plants are selected. Analysis of variance (JMP®) is run comparing the transgenic events to the appropriate controls.

In view of the above, it will be seen that several advantages of the disclosure are achieved, and other advantageous results attained. As various changes could be made in the above methods without departing from the scope of the disclosure, it is intended that all matter contained in the above description and shown in the accompanying drawings shall be interpreted as illustrative and not in a limiting sense.

The foregoing description of the specific aspects will so fully reveal the general nature of the inventions described herein that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the inventions described herein are set out in the following numbered clauses:

Clause 1. A method of protecting a plant from infection by a plant pathogen or pest, the method comprising:

transforming the plant with a nucleic acid molecule encoding a polypeptide having at least 80% sequence identity to any one of SEQ ID NOs: 1-184 to generate a transformed plant expressing the polypeptide, wherein said polypeptide has pesticidal activity against the plant pathogen or pest; and regenerating the transformed plant expressing the polypeptide.

Clause 2. The method of clause 1, wherein the polypeptide has at least 95% sequence identity to any one of SEQ ID NOs: 1-184.

Clause 3. The method of clause 1 or 2, wherein the polypeptide is any one of SEQ ID NOs: 1-184.

Clause 4. The method of any one of clauses 1-3, wherein the plant pathogen or pest is selected from the group consisting of fall armyworm (*Spodoptera frugiperda*), corn earworm (*Helicoverpa zea*), European corn borer (*Ostrinia nubilalis*), cotton boll worm (*Helicoverpa armigera*), black cutworm (*Agrotis ipsilon*), lesser cornstalk borer (*Elasmopalpus lignosellus*), Asian corn borer (*Ostinia furnacalis*), southwestern corn borer (*Diatraea grandiosella*), sugarcane borer (*Diatraea saccharalis*), western bean cutworm (*Striacosta albicosta*), velvetbean caterpillar (*Anticarsia gemmatalis*), western corn rootworm (*Diabrotica virgifera virgifera*), and combinations thereof.

Clause 5. A transformed plant, seed, or plant part comprising a recombinant nucleic acid molecule encoding a polypeptide having at least 80% sequence identity to any one of SEQ ID NOs: 1-184 stably incorporated into a genome of the transformed plant, seed, or plant part, wherein the transformed plant, seed, or plant part stably expresses the polypeptide, and wherein the polypeptide has pesticidal activity against a plant pathogen or pest.

Clause 6. The transformed plant, seed, or plant part of clause 5, wherein the polypeptide has at least 95% sequence identity to any one of SEQ ID NOs: 1-184.

Clause 7. The transformed plant, seed, or plant part of clause 5 or 6, wherein the polypeptide is any one of SEQ ID NOs: 1-184.

Clause 8. The transformed plant, seed, or plant part of any one of clauses 5-7, wherein the transformed plant, seed, or plant part is selected from the group consisting of rice, barley, sorghum, soybean, cotton, maize, rapeseed, sugar cane, tobacco, sunflower, and wheat.

Clause 9. A recombinant nucleic acid molecule comprising a polynucleotide sequence encoding a polypeptide having at least 80% sequence identity to any one of SEQ ID NOs: 1-184, wherein the polypeptide has pesticidal activity against a plant pathogen or pest.

Clause 10. The recombinant nucleic acid molecule of clause 9, wherein the polypeptide has at least 95% sequence identity to any one of SEQ ID NOs: 1-184.

Clause 11. The recombinant nucleic acid molecule of clause 9 or 10, wherein the polypeptide is any one of SEQ ID NOs: 1-184.

Clause 12. The recombinant nucleic acid molecule of any one of clauses 9-11, wherein the polynucleotide sequence encoding the polypeptide is operably linked to one or more promoter sequences.

Clause 13. A vector comprising a recombinant nucleic acid molecule comprising a polynucleotide sequence encoding a polypeptide having at least 80% sequence identity to any one of SEQ ID NOs: 1-184, wherein the polypeptide has pesticidal activity against a plant pathogen or pest.

Clause 14. The vector of clause 13, wherein the polypeptide has at least 95% sequence identity to any one of SEQ ID NOs: 1-184.

Clause 15. The vector of clause 13 or 14, wherein the polypeptide is any one of SEQ ID NOs: 1-184.

Clause 16. A transformed host cell comprising a recombinant nucleic acid molecule comprising a polynucleotide sequence encoding a polypeptide having at least 80% sequence identity to any one of SEQ ID NOs: 1-184, wherein the polypeptide has pesticidal activity against a plant pathogen or pest.

Clause 17. The transformed host cell of clause 16, wherein the polypeptide has at least 95% sequence identity to any one of SEQ ID NOs: 1-184.

Clause 18. The transformed host cell of clause 16 or 17, wherein the polypeptide is any one of SEQ ID NOs: 1-184.

Clause 19. A method of treating a plant or plant part against a plant pathogen or pest, the method comprising:

applying to the plant or plant part an effective amount of at least one polypeptide having at least 80% sequence identity to any one of SEQ ID NOs: 1-184, wherein the polypeptide has pesticidal activity against the plant pathogen or pest.

Clause 20. The method of clause 19, wherein the polypeptide has at least 95% sequence identity to any one of SEQ ID NOs: 1-184.

Clause 21. The method of clause 19 or 20, wherein the polypeptide is any one of SEQ ID NOs: 1-184.

Clause 22. A composition having insecticidal activity against a plant pathogen or pest, the composition comprising an effective amount of at least one polypeptide having at least 80% sequence identity to any one of SEQ ID NOs: 1-184.

Clause 23. The composition of clause 22, wherein the polypeptide has at least 95% sequence identity to any one of SEQ ID NOs: 1-184.

Clause 24. The composition of clause 22 or 23, wherein the polypeptide is any one of SEQ ID NOs: 1-184.

---

---

What is claimed is:

1. A transformed plant, seed, or plant part comprising a recombinant nucleic acid molecule encoding a polypeptide of any one of SEQ ID NOs: 1, 12, 19, 20, 24, 30, 42, 45, 46, 50, 55, or 57 stably incorporated into a genome of the transformed plant, seed, or plant part, wherein the transformed plant, seed, or plant part stably expresses the polypeptide, wherein the polypeptide has pesticidal activity against a plant pathogen or pest comprising corn rootworm (*Diabrotica virgifera*), western corn rootworm (*Diabrotica virgifera virgifera*), northern corn rootworm (*Diabrotica barberi*), southern corn rootworm (*Diabrotica undecim-punctata howardi*), or combinations thereof, and wherein the recombinant nucleic acid molecule encoding the polypeptide is operably linked to one or more heterologous promoter sequences.

2. The transformed plant, seed, or plant part of claim 1, wherein the transformed plant, seed, or plant part is selected from the group consisting of rice, barley, sorghum, soybean, cotton, maize, rapeseed, sugar cane, tobacco, sunflower, and wheat.

3. A recombinant nucleic acid molecule comprising a polynucleotide sequence encoding a polypeptide of SEQ ID NOs: 1, 12, 19, 20, 24, 30, 42, 45, 46, 50, 55, or 57, wherein the polypeptide has pesticidal activity against a plant pathogen or pest comprising corn rootworm (*Diabrotica virgifera*), western corn rootworm (*Diabrotica virgifera virgifera*), northern corn rootworm (*Diabrotica barberi*), southern corn rootworm (*Diabrotica undecimpunctata howardi*), or combinations thereof, and wherein the polynucleotide sequence encoding the polypeptide is operably linked to one or more heterologous promoter sequences.

4. A vector comprising a recombinant nucleic acid molecule comprising a polynucleotide sequence encoding a polypeptide of any one of SEQ ID NOs: 1, 12, 19, 20, 24, 30, 42, 45, 46, 50, 55, or 57, wherein the polypeptide has pesticidal activity against a plant pathogen or pest compris-
ing corn rootworm (*Diabrotica virgifera*), western corn
rootworm (*Diabrotica virgifera virgifera*), northern corn
rootworm (*Diabrotica barberi*), southern corn rootworm
(*Diabrotica undecimpunctata howardi*), or combinations
thereof, and wherein the polynucleotide sequence encoding
the polypeptide is operably linked to one or more heterolo-
gous promoter sequences.

5. A transformed host cell comprising a recombinant
nucleic acid molecule comprising a polynucleotide sequence
encoding a polypeptide of any one of SEQ ID NOs: 1, 12,
19, 20, 24, 30, 42, 45, 46, 50, 55, or 57, wherein the
polypeptide has pesticidal activity against a plant pathogen
or pest comprising corn rootworm (*Diabrotica virgifera*),
western corn rootworm (*Diabrotica virgifera virgifera*),
northern corn rootworm (*Diabrotica barberi*), southern corn
rootworm (*Diabrotica undecimpunctata howardi*), or com-
binations thereof, and wherein the polynucleotide sequence
encoding the polypeptide is operably linked to one or more
heterologous promoter sequences.

\* \* \* \* \*